US009526729B2

(12) United States Patent
Yu

(10) Patent No.: US 9,526,729 B2
(45) Date of Patent: Dec. 27, 2016

(54) MEDICAMENT FOR TREATING PERIPHERAL NEUROPATHIES

(71) Applicant: Hsiao Lily Yu, Ibaraki-ken (JP)

(72) Inventor: Hsiao Lily Yu, Ibaraki-ken (JP)

(73) Assignee: Hsiao Lily Yu, Ibaraki-Ken (JP)

( * ) Notice: Subject to any disclaimer, the term of this patent is extended or adjusted under 35 U.S.C. 154(b) by 0 days.

(21) Appl. No.: 14/606,035

(22) Filed: Jan. 27, 2015

(65) Prior Publication Data

US 2015/0238493 A1 Aug. 27, 2015

Related U.S. Application Data

(63) Continuation-in-part of application No. 13/752,403, filed on Jan. 29, 2013.

(30) Foreign Application Priority Data

Jan. 27, 2014 (TW) .............................. 103102851 A

(51) Int. Cl.
| | |
|---|---|
| *G01N 33/50* | (2006.01) |
| *G01N 33/48* | (2006.01) |
| *C12Q 1/70* | (2006.01) |
| *A61K 31/522* | (2006.01) |
| *A61K 45/06* | (2006.01) |

(52) U.S. Cl.
CPC ............ *A61K 31/522* (2013.01); *A61K 45/06* (2013.01); *C12Q 1/705* (2013.01); *G01N 33/5091* (2013.01)

(58) Field of Classification Search
CPC .... A61K 31/522; A61K 31/52; A61K 31/519; A61K 31/505; A61K 31/495; A61K 31/395; A61K 31/33; A61K 31/00; C12Q 1/705; C12Q 1/701; C12Q 1/70; G01N 33/5091; G01N 33/5055; G01N 33/50; G01N 33/48; G01N 33/00
USPC ............ 514/263.37, 263.38, 171, 169; 435/5
See application file for complete search history.

(56) References Cited

U.S. PATENT DOCUMENTS

| | | | |
|---|---|---|---|
| 2008/0160509 A1* | 7/2008 | Akridge ............... | A61K 31/522 435/5 |
| 2012/0178726 A1* | 7/2012 | Bladh .................. | C07J 71/0047 514/170 |
| 2013/0072458 A1* | 3/2013 | Painter ................. | A61K 31/675 514/81 |

OTHER PUBLICATIONS

Harrison et al, Infections of the Scalp, from the book Skin Infections: Diagnosis and Treatment by John C. Hall et al, 2009, Cambridge University Press, pp. 255, 257, 263-265.*
Kaminester, Lewis H., Sexually Transmitted Diseases: An Illustrated Guide to Differential Diagnosis, Wellcome co., 2008, pp. 1-28.*
Pointe Scientific, Inc, HSV IgG, Point Scientific, Inc., 2012, pp. 1-7.*
Otberg, Nina, Systemic treatment for alopecia areata, Dermatologic Therapy, Wiley Periodicals, Inc., vol. 24, 2011, pp. 320-325.*
STN Search Report, obtained on Nov. 2, 2015, pp. 1-239.*

* cited by examiner

*Primary Examiner* — Christine T Mui

(57) ABSTRACT

The invention provides a method for treatment of the diseases in a human by identifying the human as one suffering from a herpes simplex virus (HSV), and then administering to the human the compound anti-HSV agent or a pharmaceutically acceptable salt thereof. The diseases include dermatosis and non-dermatosis, wherein the dermatosis include acnes, impetigo, pyoderma gangrenosum, chilblains and psoriasiform, asteatotic dermatitis, ichthyosis, lichen simplex chronicus (Neurodermatitis, Prurigo), seborrhoeic dermatitis, rosacea, perioral dermatitis, epidermal cyst, wound ulcer, discoid lupus erythematosus, vitiligo, Alopecia, diagnostic criteria of some autoimmune diseases such as systemic lupus erythematosus or diabetic skin complications, wherein the non-dermatosis include glomerulonephritis, arthritis, Crohn's disease, ulcerative colitis, myelodysplasia, multiple myeloma, demyelinating disease, Parkinson's disease, anemia, cytopenia those among the diagnostic criteria.

10 Claims, 87 Drawing Sheets

MEDICAMENT FOR TREATING PERIPHERAL NEUROPATHIES

This patent application claims priority of Taiwan Patent Application No. 103102851, filed on Jan. 27, 2014 and claims the continuation-in-part (CIP) benefit of a U.S. patent application Ser. No. 13/752,403, filed Jan. 29, 2013, the entirety of which are incorporated herein by reference.

BACKGROUND OF THE INVENTION

1. Field of the Invention

The present invention relates generally to the diagnosis and treatment of the HSV (herpes simplex virus) infection of the dermal nerve fibers (DNFs) and free nerve endings (FNEs) in the skin.

2. Description of the Prior Art

Herpes simplex virus (HSV) is distributed worldwide, with humans being the only natural reservoirs. The most important biologic property of HSV is its capacity to invade and replicate in the nervous system, and this may cause life-threatening complications. HSV establishes and maintains a latent infection in the nerve ganglion proximal to the site of primary infection. In or facial HSV infection, the trigeminal ganglia are most commonly affected. In genital HSV infection, the sacral nerve root ganglia (S2-S5) are involved. Reactivation of the established latent infection can be induced by various stimuli (e.g., fever, trauma, emotional stress, sunlight, and menstruation) resulting in overt or covert recurrent infection. These unique biologic properties of latent infection and periodic reactivation, along with asymptomatic virus shedding, enable HSV endemicity to be maintained easily in most human communities.

SUMMARY OF THE INVENTION

According to one embodiment, the invention provides a method for a treatment of the diseases in a human by identifying the human as one suffering from a herpes simplex virus (HSV), and then administering to the human a compound anti-HSV agent or a pharmaceutically acceptable salt thereof.

According to one embodiment, the invention provides a method for treating acne in a human, comprising administering to said human an anti-Herpes simplex virus (HSV) agent.

According to another embodiment, the invention provides a method for treating acne in a human, comprising identifying said human as one suffering from herpes simplex viruses (HSV), and then administering to said human an anti-HSV agent or a pharmaceutically acceptable salt thereof.

According to another embodiment, the invention provides a method for treating acne in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

According to another embodiment, the invention provides a method for treating impetigo in a human, comprising administering to said human an anti-Herpes simplex virus (HSV) agent.

According to another embodiment, the invention provides a method for treating impetigo in a human, comprising identifying said human as one suffering from herpes simplex viruses (HSV), and then administering to said human an anti-HSV agent or a pharmaceutically acceptable salt thereof.

According to another embodiment, the invention provides a method for treating impetigo in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

According to another embodiment, the invention provides a method for treating pyoderma gangrenosum in a human, comprising administering to said human an anti-Herpes simplex virus (HSV) agent.

According to another embodiment, the invention provides a method for treating pyoderma gangrenosum in a human, comprising identifying said human as one suffering from herpes simplex viruses (HSV), and then administering to said human an anti-HSV agent or a pharmaceutically acceptable salt thereof.

According to another embodiment, the invention provides a method for treating pyoderma gangrenosum in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

According to another embodiment, the invention provides a method for treating chilblain in a human, comprising administering to said human an anti-Herpes simplex virus (HSV) agent.

According to another embodiment, the invention provides a method for treating chilblain in a human, comprising identifying said human as one suffering from herpes simplex viruses (HSV), and then administering to said human an anti-HSV agent or a pharmaceutically acceptable salt thereof.

According to another embodiment, the invention provides a method for treating chilblain in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

According to another embodiment, the invention provides a method for treating diabetic skin complications in a human, comprising administering to said human an anti-Herpes simplex virus (HSV) agent.

According to another embodiment, the invention provides a method for treating diabetic skin complications in a human, comprising identifying said human as one suffering from herpes simplex viruses (HSV), and then administering to said human an anti-HSV agent or a pharmaceutically acceptable salt thereof.

According to another embodiment, the invention provides a method for treating diabetic skin complications in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

According to one embodiment, the invention provides a method for treating alopecia in a human, comprising administering to said human an anti-Herpes simplex virus (HSV) agent.

According to another embodiment, the invention provides a method for treating alopecia in a human, comprising identifying said human as one suffering from herpes simplex viruses (HSV), and then administering to said human an anti-HSV agent or a pharmaceutically acceptable salt thereof.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 10-1$a$ is an image of an infected part of a 20-day-old newborn infant before treatment.

FIG. 10-1$b$ is a balloon degeneration in the spinous layer (circle), intraepithelial vesicles and a balloon cells nest (arrow) observed by a QTT of a vesiculopapule.

FIG. 10-2$a$ is an image of an infected part of a 4-month-old newborn infant before treatment.

FIG. 10-2$b$ is a balloon degeneration of the follicular epithelium (circles). A balloon cell (arrow) and a giant cell (circle) were observed by QTT.

FIG. 10-3$a$ is QTT of vesiculopapules from a newborn's cheek revealing a nerve extending from the dermis (vesicular cavity) to its overlying epidermal sheet.

FIG. 10-3$b$ is a balloon degeneration of cells near the basement membrane. A giant cell (circle) with many pleomorphic nuclei were also observed.

FIG. 10-3$c$ is an image of an infected part of a 5-month-old newborn infant after treatment.

FIG. 10-3$d$ is an image showing some light-brown crust on the periphery of the frontal area.

FIG. 11-1$a$ is an image of an infected part of a boy before treatment.

FIG. 11-1$b$ is an image of an infected part of a woman before treatment.

FIG. 11-1$c$ is a balloon degeneration of cells. There were many BCs with large nuclei and thick cell membrane.

FIG. 11-2$a$ is an image of an infected part of an 8-years-old boy before treatment.

FIG. 11-2$b$ is balloon degeneration of the epithelial cells, intraepithelial vesicle, and band-like BC nest (circle) observed in a QTT.

FIG. 11-2$c$ is an image of an infected part of the 8-years-old boy after treatment.

FIG. 12-1$a$ is an image of an infected part of a boy before treatment.

FIG. 12-1$b$ is an image of an infected part of the boy after treatment.

FIG. 12-2$a$ and FIG. 12-2$b$ are images of infected parts of an 11-year-old boy before treatment.

FIG. 12-2$c$ and FIG. 12-2$d$ are images of infected parts of the 11-year-old boy after treatment.

FIG. 13-1$a$ is an image of an infected part of a patient before treatment.

FIG. 13-1$b$ is a balloon degeneration of a group of BCs associated with the basement membrane. Some BCs were fused to form BC nests and GCs (circle).

FIG. 13-1$c$ is an image of an infected part of the patient after treatment.

FIG. 13-2$a$ is a QTT image from a vesicle revealing pleomorphic BCs and a giant cell on the right side possessing many nuclei molding together.

FIG. 13-2$b$ is an image of a patient 3 days after treatment.

DETAILED DESCRIPTION

Figure 1:
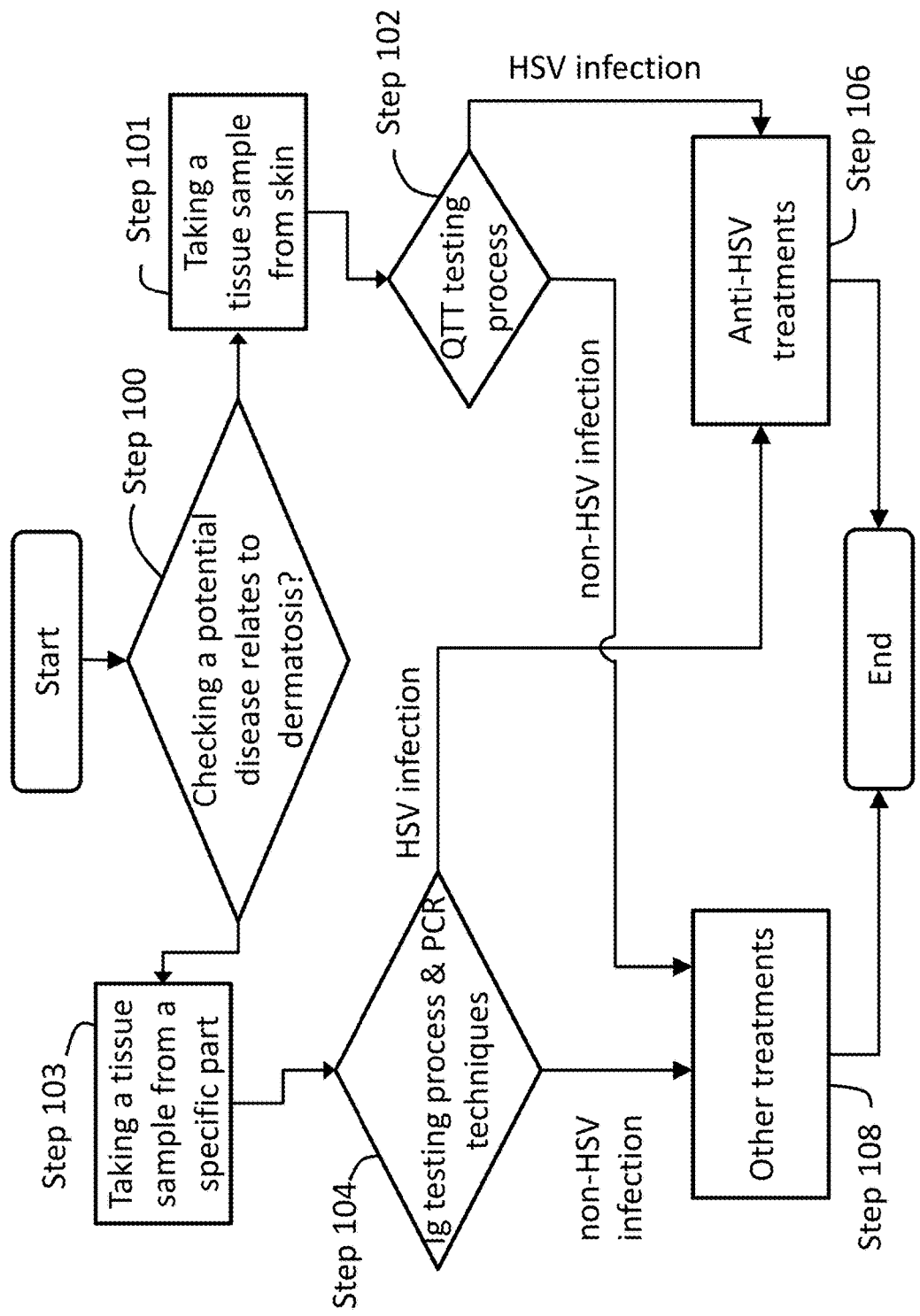
FIG. 1 is a flow chart of the detecting method in the present invention.

The invention provides a method for treatment of diseases in a human by identifying the human as one suffering from a herpes simplex virus (HSV), and then administering to the human an anti-HSV agent or the combination thereof or a pharmaceutically acceptable salt thereof.

Diseases Coming from HSV

The diseases (D) coming from HSV can be dermatosis or non-skin disease, wherein the dermatosis include acne, impetigo, pyoderma gangrenosum, chilblains and psoriasiform, asteatotic dermatitis, ichthyosis, lichen simplex chronicus (neurodermatitis, prurigo), seborrhoeic dermatitis, rosacea, perioral dermatitis, epidermal cyst, wound ulcer, discoid lupus erythematosus, vitiligo, alopecia, diagnostic criteria of some autoimmune diseases such as systemic lupus erythematosus, skin cancer and diabetic skin complications. The non-skin disease includes thyroiditis, asthma, rhinitis, sinusitis, glomerulonephritis, arthritis, Crohn's disease, ulcerative colitis, sarcoidosis, myelodysplasia, multiple myeloma, demyelinating disease, Parkinson's disease, anemia, cytopenia those among the diagnostic criteria, dementia, cancer, tumor, polyps, lung cancer, kidney cancer, breast cancer, prostate cancer, brain tumor, lymphoma, cervical cancer, oral cancer, bone cancer, pancreatic cancer, leukemia, thyroid cancer.

The following paragraphs describe a cause, a signs and a symptom of some of the diseases (D).

Acne: Acne develops as a result of blockages in the follicles. Hyperkeratinization and formation of a plug of keratin and sebum (a microcomedo) is the earliest change. Enlargement of sebaceous glands and an increase in sebum production occur with increased androgen (DHEA-S) production at adrenarche. The microcomedo may enlarge to form an open comedone (blackhead) or closed comedone (milia). Comedones are the direct result of sebaceous glands becoming clogged with sebum, a naturally occurring oil, and dead skin cells.

Impetigo: Impetigo is a highly contagious skin infection most common among pre-school children. This common form of impetigo, also called non-bullous impetigo, most often begins as a red sore near the nose or mouth which soon breaks, leaking pus or fluid, and forms a honey-colored scab followed by a red mark which heals without leaving a scar. Sores are not painful but may be itchy. Lymph nodes in the affected area may be swollen, but fever is rare. Touching or scratching the sores may easily spread the infection to other parts of the body.

Pyoderma gangrenosum: Pyoderma gangrenosum is a condition that causes tissue to become necrotic, causing deep ulcers that usually occur on the legs. When they occur, they can lead to chronic wounds. Ulcers usually initially look like small bug bites or papules, and they progress to larger ulcers. Though the etiology is not well understood, the disease is thought to be due to immune system dysfunction, and particularly improper functioning of neutrophils. At least half of all pyoderma gangrenosum patients also suffer from illnesses that affect their systemic function. For instance, ulcerative colitis, rheumatoid arthritis, and multiple myeloma sufferers have the condition.

Chilblains: Chilblain is a tissue injury that occurs when a predisposed individual is exposed to cold and humidity. The cold exposure damages capillary beds in the skin, which in turn can cause redness, itching, blisters, and inflammation. The areas most affected are the ears, earlobes, nose, and extremities; feet and toes, hands and fingers.

Psoriasiform: Psoriasiform is typically found in rheumatoid arthritis, crohn's disease, high blood pressure, psoriasis, ankylosing spondylitis. Psoriasis is a condition of the skin, which develop skin rashes and the skin at these particular areas is red, itchy and flaky. The psoriasis is not contagious. The researchers have found (so far) that psoriasis is caused by psychological factors such as too much stress.

Asteatotic dermatitis: Asteatotic dermatitis is a form of eczema that is characterized by changes that occur when skin becomes abnormally dry, itchy, and cracked. Lower legs tend to be especially affected, although it can appear in the underarm area as well. The asteatotic dermatitis is common in elderly people, though it is not uncommon for people in their 20s. It can appear in red, bumpy, pimple-like irritations.

Ichthyosis: All types of ichthyosis have dry, thickened, scaly or flaky skin. There are many types of ichthyosis and an exact diagnosis may be difficult. Types of ichthyosis are classified by their appearance and their genetic cause. Ichthyosis caused by the same gene can vary considerably in severity and symptoms.

Lichen Simplex Chronicus: Lichen simplex chronicus (also known as "Neurodermatitis") is a skin disorder characterized by chronic itching and scratching. The constant scratching causes thick, leathery, brownish skin.

Seborrhoeic dermatitis: Seborrhoeic dermatitis is an inflammatory skin disorder affecting the scalp, face, and torso. Typically, seborrheic dermatitis presents with scaly, flaky, itchy, and red skin. It particularly affects the sebaceous-gland-rich areas of skin. In adolescents and adults, seborrhoeic dermatitis usually presents as scalp scaling similar to dandruff or as mild to marked erythema of the nasolabial fold.

Rosacea: Rosacea is a chronic condition characterized by facial erythema (redness) and sometimes pimples. Rosacea affects adults and has four subtypes. Left untreated it worsens over time. Triggers that cause episodes of flushing and blushing play a part in the development of rosacea. Exposure to temperature extremes can cause the face to become flushed as well as strenuous exercise, heat from sunlight, severe sunburn, stress, anxiety, cold wind, and moving to a warm or hot environment from a cold one such as heated shops and offices during the winter.

Perioral dermatitis: Perioral dermatitis, a condition related to acne vulgaris, consists of red papules that may appear microvesicular that typically affect the nasolabial folds (around the nostrils), perioral area (around the mouth) or perioccular area (around the eyes).

Epidermal cyst: Epidermal cyst is a benign cyst usually found on the skin. The cyst develops out of ectodermal tissue. Histologically, it is made of a thin layer of squamous epithelium.

Wound ulcer: An ulcer is a sore on the skin or a mucous membrane, accompanied by the disintegration of tissue. Ulcers can result in complete loss of the epidermis and often portions of the dermis and even subcutaneous fat. Ulcers are most common on the skin of the lower extremities and in the gastrointestinal tract. An ulcer that appears on the skin is often visible as an inflamed tissue with an area of reddened skin. Ulcers often become infected, and pus forms.

Discoid lupus erythematosus (DLE): DLE is a chronic skin condition of sores with inflammation and scarring favoring the face, ears, and scalp and at times on other body areas. These lesions develop as a red, inflamed patch with a scaling and crusty appearance.

Vitiligo: Vitiligo is a condition that causes depigmentation of sections of skin. It occurs when melanocytes, the cells responsible for skin pigmentation, die or are unable to function. The cause of vitiligo is unknown, but research suggests that it may arise from autoimmune, genetic, oxidative stress, neural, or viral causes. The incidence worldwide is less than 1%. The most common form is non-segmental vitiligo, which tends to appear in symmetric patches, sometimes over large areas of the body.

Alopecia: Alopecia means loss of hair from the head or body. Alopecia can mean baldness, a term generally reserved for pattern alopecia or androgenic alopecia.

Diabetic skin complications: The diabetes patient need to be aware of potentially serious skin problems related to the disease. In most cases, skin problems in diabetes can be managed with early diagnosis and treatment. The diabetic skin complications comprising:

Scleroderma diabeticorum: While rare, this skin problem affects people with type 2 diabetes, causing a thickening of the skin on the back of the neck and upper back.

Vitiligo, a skin problem more commonly associated with type 1 diabetes than type 2 diabetes, affects skin coloration.

Acanthosis nigricans: This is a skin problem that results in the darkening and thickening of certain areas of the skin especially in the skin folds. The skin becomes tan or brown and is sometimes slightly raised and described as velvety. Acanthosis nigricans usually strikes people who are very overweight. While there is no cure for acanthosis nigricans, losing weight may improve the skin condition. Acanthosis nigricans usually precedes diabetes and is considered to be a marker for the disease.

Diabetic blisters (bullosis diabeticorum): In rare cases, people with diabetes develop skin problems, such as blisters that resemble burn blisters. These blisters can occur on the fingers, hands, toes, feet, legs, or forearms. Diabetic blisters usually are painless and heal on their own. These skin problems often occur in people who have severe diabetes and diabetic neuropathy.

Glomerulonephritis: Glomerulonephritis (GN) is a renal disease characterized by inflammation of the glomeruli, or small blood vessels in the kidneys. It may present with isolated hematuria and/or proteinuria (blood or protein in the urine); or as a nephrotic syndrome, a nephritic syndrome, acute renal failure, or chronic renal failure. They are categorized into several different pathological patterns, which are broadly grouped into non-proliferative or proliferative types. Diagnosing the pattern of GN is important because the outcome and treatment differs in different types. Primary causes are intrinsic to the kidney. Secondary causes are associated with certain infections (bacterial, viral or parasitic pathogens), drugs, systemic disorders (SLE, vasculitis), or diabetes.

Arthritis: Arthritis is a form of joint disorder that involves inflammation of one or more joints. There are over 100 different forms of arthritis. The most common form, osteoarthritis (degenerative joint disease), is a result of trauma to the joint, infection of the joint, or age. Other arthritis forms are rheumatoid arthritis, psoriatic arthritis, and related autoimmune diseases. Septic arthritis is caused by joint infection. The major complaint by individuals who have arthritis is joint pain. Pain is often a constant and may be localized to the joint affected. The pain from arthritis is due to inflammation that occurs around the joint, damage to the joint from disease, daily wear and tear of joint, muscle strains caused by forceful movements against stiff painful joints and fatigue.

Crohn's disease: Crohn's disease is a type of inflammatory bowel disease that may affect any part of the gastrointestinal tract from mouth to anus, causing a wide variety of symptoms. It primarily causes abdominal pain, diarrhea (which may be bloody if inflammation is at its worst), vomiting (can be continuous), or weight loss, but may also cause complications outside the gastrointestinal tract such as skin rashes, arthritis, inflammation of the eye, tiredness, and lack of concentration. Crohn's disease is caused by interactions between environmental, immunological and bacterial factors in genetically susceptible individuals. This result in a chronic inflammatory disorder, in which the body's immune system attacks the gastrointestinal tract possibly directed at microbial antigens. Crohn's disease has traditionally been described as an autoimmune disease, but recent investigators have described it as an immune deficiency state.

Myelodysplasia: The myelodysplastic syndromes (MDS, formerly known as preleukemia) are a diverse collection of hematological (blood-related) medical conditions that involve ineffective production (or dysplasia) of the myeloid class of blood cells. Patients with MDS often develop severe anemia and require frequent blood transfusions. In most cases, the disease worsens and the patient develops cytopenias (low blood counts) caused by progressive bone marrow failure. In about one third of patients with MDS, the disease transforms into acute myelogenous leukemia (AML), usually within months to a few years.

Multiple myeloma: Multiple myeloma is a cancer of plasma cells, a type of white blood cell normally responsible for producing antibodies. In multiple myeloma, collections of abnormal plasma cells accumulate in the bone marrow, where they interfere with the production of normal blood cells. Most cases of myeloma also feature the production of a paraprotein an abnormal antibody which can cause kidney problems. Bone lesions and hypercalcemia (high calcium levels) are also often encountered. Myeloma is generally thought to be treatable but incurable. Remissions may be induced with steroids, chemotherapy, proteasome inhibitors (e.g. bortezomib), immunomodulatory drugs (IMiDs) such as thalidomide or lenalidomide, and stem cell transplants. Radiation therapy is sometimes used to reduce pain from bone lesions.

Demyelinating disease: Demyelinating disease is any disease of the nervous system in which the myelin sheath of neurons is damaged. This impairs the conduction of signals in the affected nerves, causing impairment in sensation, movement, cognition, or other functions depending on which nerves are involved. Some demyelinating diseases are caused by genetics, some by infectious agents, some by autoimmune reactions, and some by unknown factors.

Anemia: Anemia is a decrease in number of red blood cells (RBCs) or less than the normal quantity of hemoglobin in the blood. However, it can include decreased oxygen-binding ability of each hemoglobin molecule due to deformity or lack in numerical development as in some other types of hemoglobin deficiency. Because hemoglobin normally carries oxygen from the lungs to the capillaries, anemia leads to hypoxia (lack of oxygen) in organs.

Ulcerative colitis: Ulcerative colitis (Colitis ulcerosa, UC) is a form of inflammatory bowel disease (IBD). Ulcerative colitis is a form of colitis, a disease of the colon (large intestine) that includes characteristic ulcers, or open sores. The main symptom of active disease is usually constant diarrhea mixed with blood, of gradual onset. Ulcerative colitis has similarities to Crohn's disease. Ulcerative colitis is an intermittent disease, with periods of exacerbated symptoms, and periods that are relatively symptom-free. Although the symptoms of ulcerative colitis can sometimes diminish on their own, the disease usually requires treatment to go into remission. Ulcerative colitis is treated as an autoimmune disease. Treatment is with anti-inflammatory drugs, immunosuppression, and biological therapy targeting specific components of the immune response. Colectomy (partial or total removal of the large bowel through surgery) is occasionally necessary if the disease is severe, doesn't respond to treatment or if significant complications develop. A total proctocolectomy (removal of the entirety of the large bowel) can be curative, but it may be associated with complications.

Parkinson's disease: Parkinson's disease (also known as Parkinson disease, Parkinson's, idiopathic parkinsonism, primary parkinsonism, PD, hypokinetic rigid syndrome/HRS, or paralysis agitans) is a degenerative disorder of the central nervous system. The motor symptoms of Parkinson's disease result from the death of dopamine-generating cells in the substantia nigra, a region of the midbrain; the cause of this cell death is unknown. Early in the course of the disease, the most obvious symptoms are movement-related; these include shaking, rigidity, slowness of movement and difficulty with walking and gait. Later, cognitive and behavioural problems may arise, with dementia commonly occurring in the advanced stages of the disease. Other symptoms include sensory, sleep and emotional problems.

So far, there is no literature and research showing that the above-mentioned diseases are related to HSV infection. In the present invention, the relationship between the above-mentioned diseases and HSV are provided by the inventor according to the clinical cases for years. The inventor proposes that dermatosis like symptoms of the above-mentioned diseases may be caused further by HSV infection so as to orally administer to a human infected with Herpes simplex virus (HSV) that causes the dermatosis like symptoms of the above-mentioned diseases an agent comprising:
2-[(2-amino-6-oxo-6,9-dihydro-3H-purin-9-yl)methoxy] ethyl-2-amino-3-methylbutanoate or a pharmaceutically acceptable salt thereof; and/or
2-Amino-1,9-dihydro-9-((2-hydroxyethoxy)methyl)-6H-purin-6-one or a pharmaceutically acceptable salt thereof.

The following contexts explain HSV infection, HSV inspection programs, process for treating HSV infection, drugs for treating HSV infection and new indications for clinical HSV infection cases.

Common Clinical Case of HSV Infection

The clinical course of HSV infection depends on the age and immune status of the host, the anatomic site involved, and the antigenic virus type. The clinical cases are frequently seen as below:
 (1) Acute herpetic gingivostomatitis
 (2) Acute herpetic pharyngotonsillitis
 (3) Herpes labialis
 (4) Herpetic whitlow
 (5) Genital herpes: primary, recurrent, or subclinical
 (6) HSV inspection program Diagnosis of HSV Infection Several methods that can facilitate the diagnosis of HSV infection are proposed in the present invention as below:
 (1) Tissue culture: Tissue culture that shows the characteristic cytopathic effect—ballooning cells and cell death (apoptosis)—is one preferable method to confirm HSV infection. However, the quality of tissue culture is operator-dependent, and it takes 48 hours to run the protocol. Immunofluorescent staining of tissue culture cells can quickly identify HSV and it can distinguish type 1 from type 2.
 (2) Quick Tzanck Test (QTT) process: A Tzanck preparation with a positive finding of balloon cells and multinucleated giant cells containing intranuclear eosinophilic inclusion bodies is a time-honored procedure for assisting in the diagnosis of cutaneous herpesvirus infections.
 (3) Hematoxylin-eosin (HE) stain: Hematoxylin-eosin and other special stains for staining biopsy provide more histological information when lesions are possibly superinfected with bacteria or fungi.
 (4) Polymerase chain reaction (PCR) techniques: Detection of HSV DNA in clinical specimens is possible with polymerase chain reaction (PCR) techniques. PCR is a rapid, noninvasive diagnostic technique for HSV encephalitis and meningitis. It is also useful in detecting asymptomatic viral shedding. The PCR test may be performed on cells or fluid from a sore or on blood or on other fluid, such as spinal fluid. The genetic material (DNA) of the HSV virus may be detected via the PCR techniques. This test can tell the difference between HSV-1 and HSV-2. The PCR techniques may be performed on spinal fluid, in which herpes may cause an infection in or around the brain. Alternatively, the PCR techniques may be performed on skin sores.

(5) Direct fluorescent antigen (DFA): This procedure requires 2-3 hours. It is used to distinguish HSV-1 infection from HSV-2 infection.

(6) Antibody testing: Antibody testing, e.g. HSV immunoglobulin G (IgG) testing, non-specific immunoglobulin E (IgE) testing, Cytomegalovirus (CMV) IgG testing, can demonstrate primary seroconversion, particularly for HSV-1 infection in childhood. With respect to HSV IgG testing and non-specific IgE testing, HSV IgG testing or non-specific IgE testing is used to detect the presence of the herpes simplex virus in those who have genital sores, encephalitis, and in newborns suspected of having neonatal herpes, a rare but serious condition in which herpes is contracted during birth. The HSV IgG testing or non-specific IgE testing can be used to help diagnose an acute HSV infection if acute and convalescent blood samples are collected. The convalescent blood sample is collected several weeks after the acute sample. The HSV IgG antibody levels from the acute and convalescent blood samples may be compared to see if they have risen significantly, indicating a current infection. Alternatively, the non-specific IgE antibody levels from the acute and convalescent blood samples may be compared to see if they have risen significantly, indicating a current infection. With respect to CMV IgG testing, the CMV IgG testing is used to determine whether someone with signs and symptoms has an active infection. CMV IgG antibodies are produced by the body several weeks after the initial CMV infection, such as HSV infection, and provide protection from primary infections. Levels of CMV IgG rise during the active CMV infection, then stabilize as the CMV infection resolves and finally the HSV virus become inactive. After a person has been exposed to CMV, he or she will have some measurable amount of CMV IgG antibodies in their blood for the rest of their life. CMV IgG antibody testing can be used, along with CMV IgM testing, to help confirmation of the presence of a recent or previous CMV infection.

(7) Imaging studies: Brain imaging studies in HSV encephalitis generally demonstrate focal localization in the temporal area; this is associated with edema and contrast enhancement.

HSV Inspection Program in Pregnant Women

Dealing with genital herpes during pregnancy can be extremely stressful because of the possibility of severe consequences if a child becomes infected with the herpes virus during labor or shortly after being born. Neonatal herpes can be deadly, and so women are often counseled toward very conservative management of their pregnancy and delivery options.

The risk of neonatal herpes is highest, by far, for children women who become infected with herpes during their pregnancy, especially those who get infected near the end of their pregnancy. Transmission rates are substantially lower for women who have been infected for a long period of time, even if they have an active infection during the course of their pregnancy.

Newborn infants can become infected with herpes virus via the following ways:

(1) In the uterus (congenital herpes)
(2) Passing through the birth canal (birth-acquired herpes)
(3) Kissing or contacting with someone who has herpes mouth sores right after birth (postpartum)

If the pregnant woman has an active genital herpes infection at the time of delivery, her baby is more likely to become infected with HSV during birth. Some of the pregnant woman may not be aware that they have internal (inside the vagina) herpes sores.

Some people have had herpes infections in the past, but were not aware of it. These people, not knowing that they have herpes, may pass it to their baby.

HSV-2 (genital herpes) is the most common cause of herpes infection in newborn babies, but HSV-1 (oral herpes) can also occur.

Besides, if the pregnant woman has one of the above-mentioned diseases (D) coming from HSV at the time of delivery, her baby is also likely to become infected with HSV during birth. For more elaboration, the diseases (D) coming from HSV, as mentioned above, may be dermatosis or non-skin disease, wherein the dermatosis include acne, impetigo, pyoderma gangrenosum, chilblains and psoriasiform, asteatotic dermatitis, ichthyosis, lichen simplex chronicus (neurodermatitis, prurigo), seborrhoeic dermatitis, rosacea, perioral dermatitis, epidermal cyst, wound ulcer, discoid lupus erythematosus, vitiligo, alopecia, diagnostic criteria of some autoimmune diseases such as systemic lupus erythematosus, skin cancer and diabetic skin complications. The non-skin disease includes thyroiditis, asthma, rhinitis, sinusitis, glomerulonephritis, arthritis, Crohn's disease, ulcerative colitis, sarcoidosis, myelodysplasia, multiple myeloma, demyelinating disease, Parkinson's disease, anemia, cytopenia those among the diagnostic criteria, dementia, cancer, tumor, polyps, lung cancer, kidney cancer, breast cancer, prostate cancer, brain tumor, lymphoma, cervical cancer, oral cancer, bone cancer, pancreatic cancer, leukemia, thyroid cancer.

Symptoms in Newborn Infants Infected with HSV

HSV may only appear as a skin infection. Small, fluid-filled blisters (vesicles) may appear. These blisters rupture, crust over, and finally heal, often leaving a mild scar.

HSV infection may also spread throughout the body (called disseminated herpes). In this type, the herpes virus can affect many different parts of the body.

(1) HSV infection in the brain is called herpes encephalitis
(2) The liver, lungs, and kidneys may also be involved
(3) There may or may not be blisters on the skin Newborn infants with HSV that has spread to the brain or other parts of the body are often very sick. Symptoms include:

(1) Bleeding easily
(2) Breathing difficulties
   a. Blue appearance (cyanosis)
   b. Flaring of the nostrils
   c. Grunting
   d. Rapid breathing (tachypnea)
   e. Short periods without breathing (apneic episodes)
(3) Coma
(4) Jaundice
(5) Lethargy
(6) Low body temperature (hypothermia)
(7) Poor feeding
(8) Seizures
(9) Shock

(10) Bacterial or fungal infection of skin lesions, fluid-filled blisters
(11) Eye disease, such as inflammation of the retina (chorioretinitis or keratitis)
(12) Severe brain damage, brain and nervous system (neurological) problems
(13) Death
(14) Disseminated intravascular coagulation (DIC)
(15) Gastrointestinal problems such as diarrhea
(16) Hepatitis or liver failure
(17) Lung problems such as pneumonia or pneumonitis
(18) Allergic rhinitis
(19) Atopic dermatosis Herpes that is caught in the period shortly after birth (postpartum) has symptoms similar to those of birth-acquired herpes.

Prenatal Check-Up for the Pregnant Woman with the Diseases (D)

In order to reduce the risk of transmission of the HSVs to infants, experienced inspector or a medical staff may do the diagnosis of HSV infection for the pregnant via the tissue culture, quick Tzanck test (QTT), HE stain, polymerase chain reaction (PCR) techniques, direct fluorescent antigen (DFA), antibody testing and/or imaging studies, as mentioned above, when the pregnant woman has the diseases (D) as mentioned above. If the pregnant woman is diagnosed to be infected with HSV, the infection of HSV is suggested to be cured as mentioned below before she is in labor or cesarean delivery. The pregnant woman who has an active outbreak of genital herpes in labor is suggested to have a cesarean section. The pregnant woman who have herpes lesions in any area other than the genital area may not be necessary to have a cesarean section, but the herpes lesions is suggested to be covered with an occlusive dressing before vaginal delivery.

A pregnant woman who has been diagnosed with herpes may be monitored regularly prior to delivery to identify a reactivation of her infection, which would indicate the necessity for a caesarean section to avoid infecting her infant.

Accordingly, HSV may be prevented from being vertically infected by the pregnant woman to her infant if the pregnant woman may be treated by the anti-HSV agent, mentioned in the following section of "Anti-HSV Treatment", before her infant is delivered. Thereby, her infant may avoid some widely-spread diseases, such as allergic rhinitis or atopic dermatosis, which could be caught by HSV.

Process to Diagnose Diseases (D) in HSV Infection

FIG. 1 is a flow chart of a detecting method in the present invention.

Step 100: Checking a potential disease (D) relates to a dermatosis or a non-skin disease. For example, some questions are given for the patient and the skin of the patient is checked by an experienced inspector or a medical staff to determine if a potential disease (D) had by the patent relates to a dermatosis or a non-skin disease. If the potential disease (D) relates to a dermatosis, the inspector or the medical staff will take some tissue samples from an affected part of a patient's skin, as illustrated in step 101, and the test in step 102 for testing the tissue samples from the patient's skin will continue. If the disease (D) relates to a non-skin disease, the inspector or the medical staff takes a tissue sample from a specific part, such as peripheral blood, skin, bone marrow, mucosa, saliva, cerebrospinal fluid, amniotic fluid, brain tissue, tears or skin secretions, of the patient, as illustrated in step 103, based on the method for testing the tissue sample in step 104, and then the test in step 104 for testing the tissue samples from the specific part of the patient will continue.

Step 102: Performing a Quick Tzanck Test (QTT) process. The QTT process can be applied to the tissue samples from the patient's skin so as to reveal some histopathological changes from the QTT sample, i.e. the tissue samples from the patient's skin, by using a microscope. The inspector or the medical staff can observe the histopathological changes to diagnose HSV infection. When the QTT testing's result shows "HSV infection", step 106 of "anti-HSV treatments" continues. When the result shows "Non-HSV infection", step 108 of "other treatments" continues.

Step 104: Performing an antibody testing or a PCR techniques on the tissue sample from the specific part of the patient. The antibody testing, such as the HSV IgG testing, the cytomegalovirus immunoglobulin G (CMV IgG) testing or the non-specific immunoglobulin E (IgE) testing is adapted to be performed on a peripheral blood, acting as the tissue sample, of the patient. The PCR testing is adapted to be performed on peripheral blood, skin, bone marrow, mucosa, saliva, cerebrospinal fluid, amniotic fluid, brain tissue, tears or skin secretions, acting as the tissue sample, of the patient. The antibody testing or PCR techniques may be referred to the description in the section of "Diagnosis of HSV Infection". The normal titer for CMV IgG/HSV IgG is less than 2 and the normal titer for non-specific IgE is less than 170 IU/ml. When the tissue sample from peripheral blood of the patient has a titer for CMV IgG/HSV IgG greater than 2, the process of "anti-HSV treatments" in step 106 is then carried out. Otherwise, the step 108 of "other treatments" is carried out. Alternatively, when the result of detecting the tissue sample via the PCR techniques is positive, the process of "anti-HSV treatments" in step 106 is then carried out; when the result of detecting the tissue sample via the PCR techniques is negative, the step 108 of "other treatments" is carried out.

Step 106: Treating an anti-HSV treatment of, for example, prescribing an anti-HSV medicine or an anti-HSV cream for the patient. The patient may take the anti-HSV medicine to cure the HSV infection. Alternatively, the patient may apply the anti-HSV cream onto the affected part of the patient's skin.

In this invention, the inventor intends to take the samples from the lesion through a Quick Tzanck Test (QTT) process, which is no need for washing, thus preserving nearly all the cells of the epidermis and vesicular cavity of the lesion. The QTT stain has staining characteristics similar to those of hematoxylin-eosin, and allows precise interpretation of the cytological changes in the dermal neural network and follicular epithelium. Such cytological changes are usually present and observable at an early stage in herpetic lesions.

Figure 2:
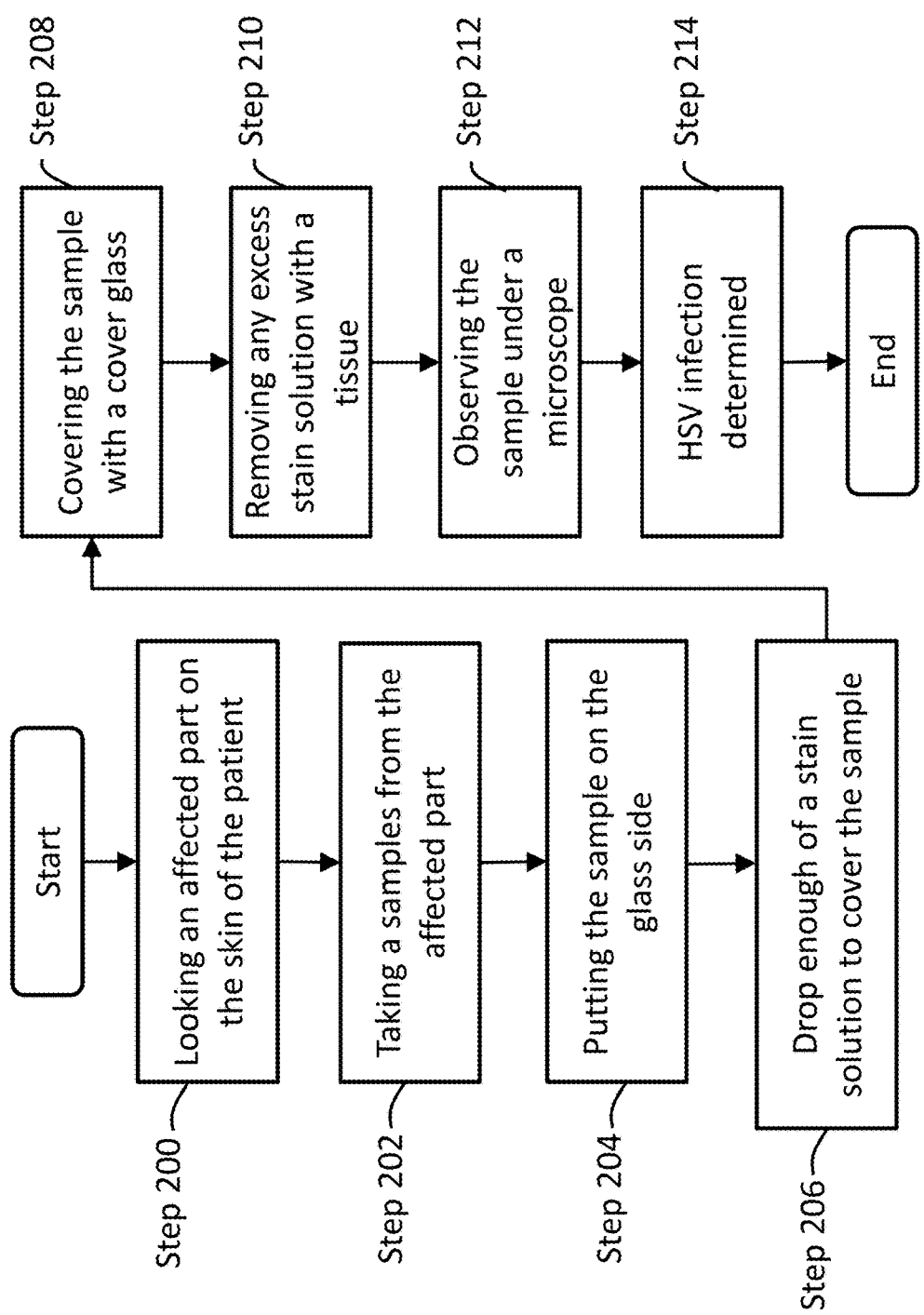
FIG. 2 is a flow chart describing smear preparation for the QTT process and diagnosis for a dermatosis.

FIG. 2 is a flow chart describing smear preparation for the QTT process and diagnosis for a dermatosis.

Step 200: Finding an affected part of the patient's skin, on the skin of the patient, for example, vesicles, pustules, vesicopapules, erosions or scales.

Step 202: Taking the tissue sample from the affected part of the patient's skin. The sample is preferably thicker than 50 μm and contains the epidermal sheet and vesicular content with a fine pincer (tip width: 1 mm, without hooks; length: 130 mm).

Step 204: Putting the tissue sample from the patient's skin on the glass slide, for example, spreading the sample on a glass slide by gently tapping the sample on the slide with the pincer repeatedly.

Step 206: Dropping a stain solution to cover the tissue sample from the patient's skin. In one embodiment, the stain solution can be a modified Giemsa stain solution which contains Giemsa solution, isopropanol and propylene glycol in a ratio of 2:1:1.

Step 208: Covering the tissue sample from the patient's skin with a cover glass.

Step 210: Removing an excess portion of the stain solution from the glass slide.

Step 212: Observing an image of the tissue sample from the patient's skin under a light microscope at least 2 minutes later or within 15 minutes after the stain solution is dropped onto the tissue sample from the patient's skin.

Step 214: Determining the patient is infected by HSV based on the image observed under the light microscope.

In step 214, by observing the image of the tissue sample, i.e. QTT sample, from the patient's skin under a microscope, some histopathological changes can be observed and the viral infection can be diagnosed. The histopathological change, for example, comprises an altered shape, a membrane fusion, inclusion bodies, lysis, and apoptosis, and usually, the change of cell size. The cell size varies from 5-50 micrometers in a transverse dimension compared to a normal tissue sample not infected by HSV.

Other Treatments for Non-Skin Diseases

Other treatments for non-skin diseases, such as cancer, tumor, lung cancer, kidney cancer, breast cancer, prostate cancer, brain tumor, lymphoma, cervical cancer, oral cancer, bone cancer, pancreatic cancer, leukemia or thyroid cancer, are described as below.

Figure 3:
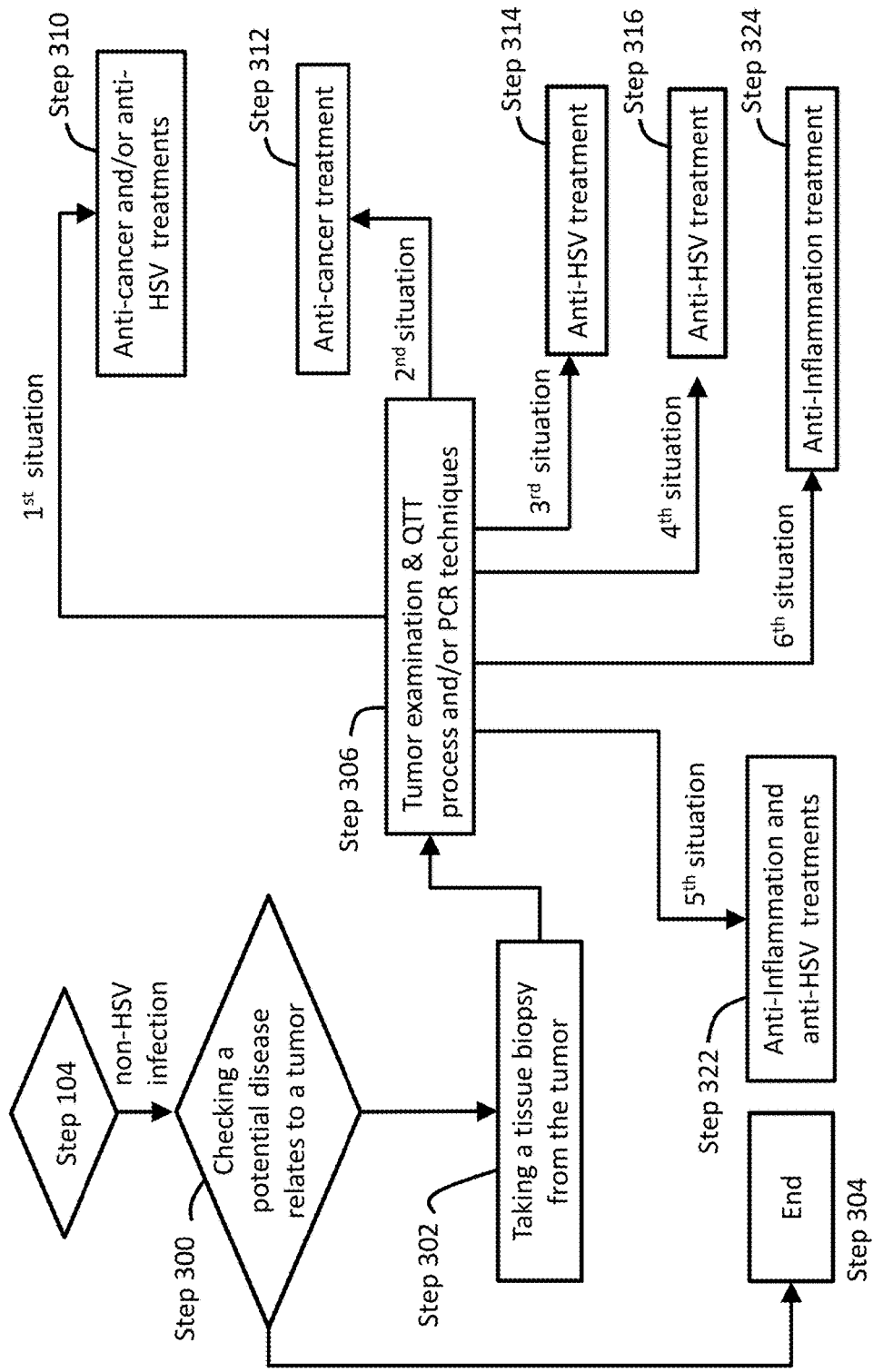
FIG. 3 is a flow chart of a detecting HSV method for Non-symptom on the skin.

FIG. 3 is a flow chart of treating non-skin diseases in accordance with an embodiment of the present invention.

Step 300: checking if a potential disease, such as cancer, tumor, lung cancer, kidney cancer, breast cancer, prostate cancer, brain tumor, lymphoma, cervical cancer, oral cancer, bone cancer, pancreatic cancer, leukemia or thyroid cancer, is found via one or more testing or diagnosing processes, for example, an inquiry process, a palpation process, a X-ray examination, a commuted tomography (CT) process, a Magnetic Resonance Imaging (MRI) process, a blood sampling routine process, an endoscopy process, a sonogram process, a colonoscopy process and/or an urine routine testing process. When the potential disease is determined to be caught by the patient, step 302 of taking a tissue biopsy may continue. Otherwise, the process of treating non-skin diseases may be finished, as illustrated in step 304.

Step 302: taking a tissue biopsy of a tumor from a viscus of the patient, or an inner organ, such as liver, kidney, lung, kidney, bone, pancreas, blood, thyroid, inside the patient, via a surgery; after the tissue biopsy is taken from the viscus of the patient via the surgery, and step 306 of tumor examination and QTT processes is then carried out.

Step 306: performing a tumor examination to a first portion of the tissue biopsy, taken in the step 302, and a QTT process and/or PCR techniques to a second portion of the tissue biopsy taken in the step 302. In the tumor examination, the first portion of the tissue biopsy may be diagnosed as a malignant tumor, benign tumor or inflammation. In the QTT process and PCR techniques, the second portion of the tissue biopsy may be diagnosed as HSV-like infection or non-HSV-like infection. There are six possible situations for the combinations of the tumor examination and the QTT process/PCR techniques, illustrated as below:

|  | 1st situation | 2nd situation | 3rd situation | 4th situation |
|---|---|---|---|---|
| Tumor examination | Malignant | Malignant | Benign | Benign |
| QTT process/PCR techniques | HSV-like infection | non-HSV-like infection | HSV-like infection | non-HSV-like infection |

|  | 5th situation | 6th situation |
|---|---|---|
| Tumor examination | Inflammation | Inflammation |
| QTT process/PCR techniques | HSV-like infection | non-HSV-like infection |

1st situation: In the tumor examination, the first portion of the tissue biopsy is diagnosed as a malignant tumor; in the QTT process/PCR techniques, the second portion of the tissue biopsy is diagnosed as HSV-like infection. For the first situation, after the step 306 of performing the tumor examination and the QTT process/PCR techniques, step 310 continues.

2nd situation: In the tumor examination, the first portion of the tissue biopsy is diagnosed as a malignant tumor; in the QTT process/PCR techniques, the second portion of the tissue biopsy is diagnosed as non-HSV-like infection. For the second situation, after the step 306 of performing the tumor examination and the QTT process/PCR techniques, step 312 continues.

3rd situation: In the tumor examination, the first portion of the tissue biopsy is diagnosed as a benign tumor; in the QTT process/PCR techniques, the second portion of the tissue biopsy is diagnosed as HSV-like infection. For the third situation, after the step 306 of performing the tumor examination and the QTT process/PCR techniques, step 314 continues.

4th situation: In the tumor examination, the first portion of the tissue biopsy is diagnosed as a benign tumor; in the QTT process/PCR techniques, the second portion of the tissue biopsy is diagnosed as non-HSV-like infection. For the fourth situation, after the step 306 of performing the tumor examination and the QTT process/PCR techniques, step 316 continues.

5th situation: In the tumor examination, the first portion of the tissue biopsy is diagnosed as inflammation; in the QTT process/PCR techniques, the second portion of the tissue biopsy is diagnosed as HSV-like infection. For the fifth situation, after the step 306 of performing the tumor examination and the QTT process/PCR techniques, step 322 continues.

6th situation: In the tumor examination, the first portion of the tissue biopsy is diagnosed as inflammation; in the QTT process/PCR techniques, the second portion of the tissue biopsy is diagnosed as non-HSV-like infection. For the sixth situation, after the step 306 of performing the tumor examination and the QTT process/PCR techniques, step 324 continues.

Step 310: performing an anti-cancer treatment and/or anti-HSV treatment on the patient.

Step 312: performing an anti-cancer treatment on the patient.

Step 314: performing an anti-HSV treatment on the patient.

Step 316: performing an anti-HSV treatment on the patient because a tumor may be caused via HSV infection.

Step 322: performing an anti-inflammation treatment and an anti-HSV treatment on the patent.

Step 324: performing an anti-inflammation treatment on the patient.

Figure 4:
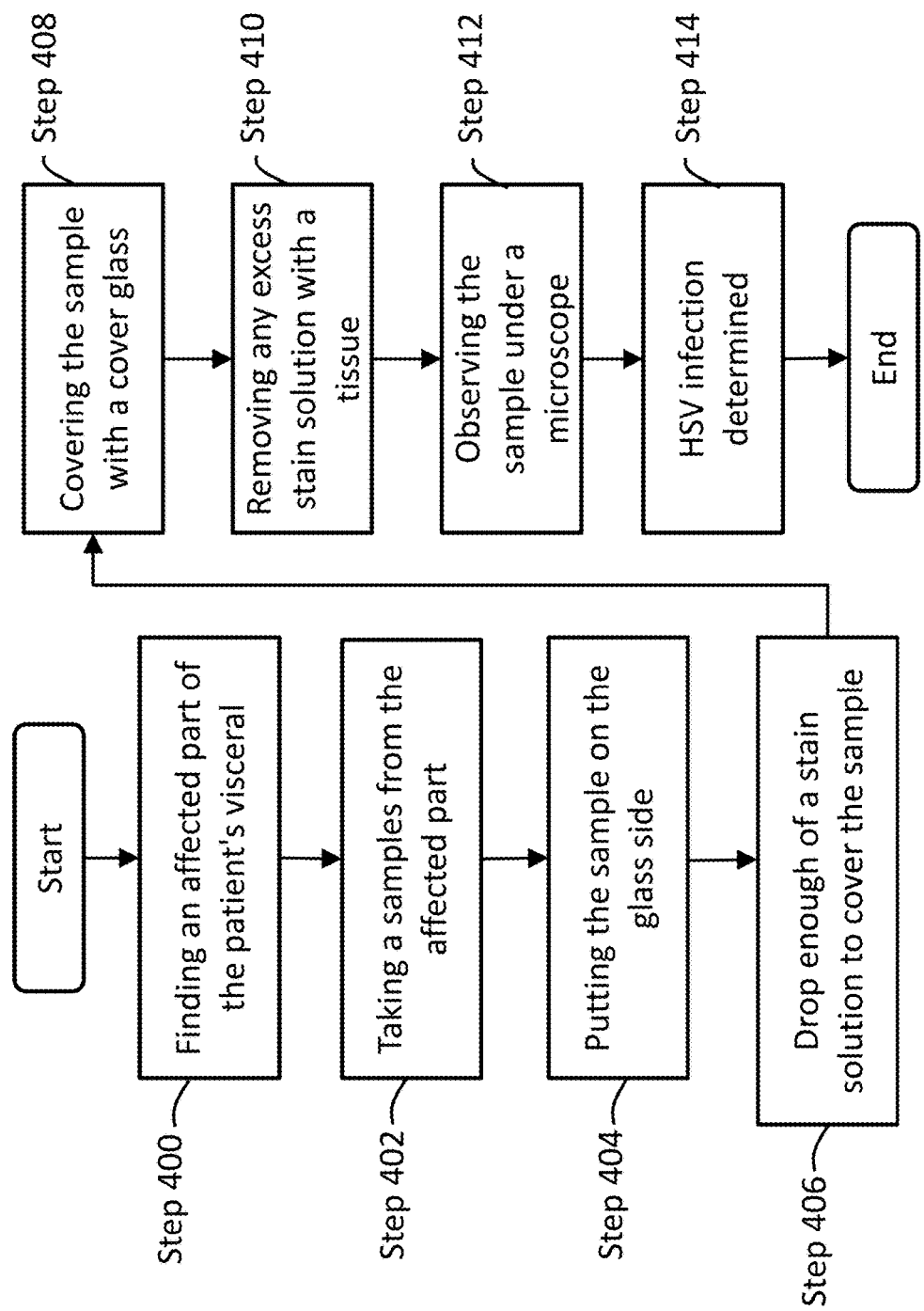
FIG. 4 is a flow chart describing smear preparation for the QTT process and diagnosis for a non-skin disease.

FIG. 4 is a flow chart describing smear preparation for the QTT process and diagnosis for a non-skin disease.

Step 400: Finding an affected part of the patient's visceral or finding a potential location of the patient's visceral, for example, tumor, inflammation, sputum, nasal discharge, genital discharge, ascites, pleural effusion, cerebral spinal fluid or polyps.

Step 402: Taking the tissue sample from the affected part of the patient's visceral. The sample is preferably thicker than 1 mm, 0.5 mm, 0.3 mm or 0.05 mm.

Step 404: Putting the tissue biopsy sample on the glass slide, for example, spreading the sample on a glass slide by gently tapping the sample on the slide with the pincer repeatedly.

Step 406: Dropping a stain solution to cover the tissue biopsy sample. In one embodiment, the stain solution comprises Giemsa solution, isopropanol and propylene glycol in a ratio of 2:1:1.

Step 408: Covering the tissue biopsy sample with a cover glass.

Step 410: Removing an excess portion of the stain solution from the glass slide.

Step 412: Observing an image of the tissue biopsy sample under a light microscope.

Step 414: Determining the patient is infected by HSV based on the image observed under the light microscope.

In step 414, by observing the image of the tissue biopsy sample, some histopathological changes can be observed and the viral infection can be diagnosed. The histopathological change, for example, comprises an altered shape, a membrane fusion, inclusion bodies, lysis, and apoptosis, and usually, the change of cell size.

Figure 5:
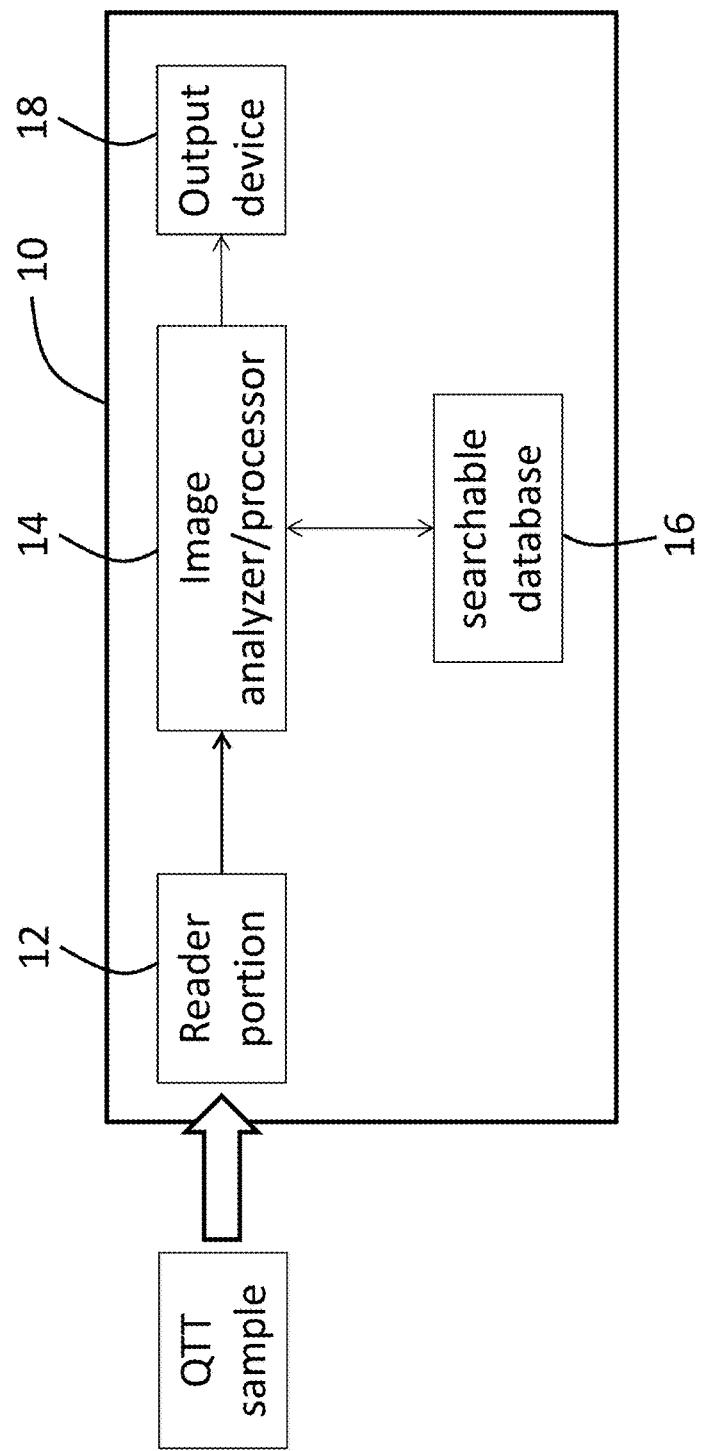
FIG. 5 is a block diagram of a HSV identification imaging system in the present invention.

An identification system may identify some histopathological changes from the QTT sample, i.e. the tissue sample from the patient's skin, visceral, tumor, inflammation or polyps, in a microscope and confirm the diagnosis with the clinical picture, i.e. the above-mentioned image generated by the microscope, to diagnose viral infection. FIG. 5 is a block diagram of a HSV identification imaging system 10. An HSV identification imaging system 10 includes a reader portion 12, an image analyzer/processor 14 and a searchable database 16, and an output 18. The reader portion 12 could be any of a number of known systems, such as complementary-metal-oxide-silicon (CMOS) image sensor, capable of capturing multiple cell images from the clinical picture, i.e. the above-mentioned image generated by the microscope, and transferring the cell images to the image analyzer/processor 14. The HSV identification imaging system 10 can be an identification device that includes an identification software.

The image analyzer/processor 14 can create an image model combining some of the cell images, such as those arranged in a 10*10 grid, in a 50*50 grid or in another grid having more than 2 rows and 2 columns, divided from image data received from the reader portion 12. The image model may be determined of interest by the image analyzer/processor 14 comparing a color and/or a partial profile of a cell shown in each cell image in the image model with those of a cell shown in images expressing features of HSV infection stored in the searchable database 16. If the cell images in the image model, having a number greater than a threshold number, are determined to have features as shown in the images expressing features of HSV infection, the image model may be deemed as an image model of interest. If the cell images in the image model, having a number less than the threshold number, are determined to have features as shown in the images expressing features of HSV infection, the image model may not be deemed as an image model of interest. For example, the images expressing features of HSV infection may include the image has a specific color, such as hyacinthine, slate gray, blue or purple, other than white and black, similar to the color of the stain solution in the QTT process.

The image model of interest may express cell images showing a continuous profile of a complete cell of interest, such as a complete balloon or giant cell, or a continuous profile of an infected area or showing a continuous profile of a part of a cell of interest, such as a balloon or giant cell. The image model may be determined to include cells of interest based on a specific color of a cell shown in the image model, such as hyacinthine, slate gray, blue or purple, other than white and black and/or a specific profile of a cell shown in the image model.

Next, the image model of interest may be compared with image models of HSV infection, stored in the searchable database 16, by the image analyzer/processor 14 to determine if the image model of interest is indicative of a HSV-infected cell. The searchable database 16 stores a lot of image models of HSV infection and a lot of images expressing features of HSV infection. It is able, by using the image models of HSV infection and the images expressing features of HSV infection, to quickly and efficiently make a determination, whether the image model of interest is substantially similar to any of the image models of HSV infection stored in the searchable database 16. The output device 18 may show the comparison result and analysis data on a display.

Figure 6:
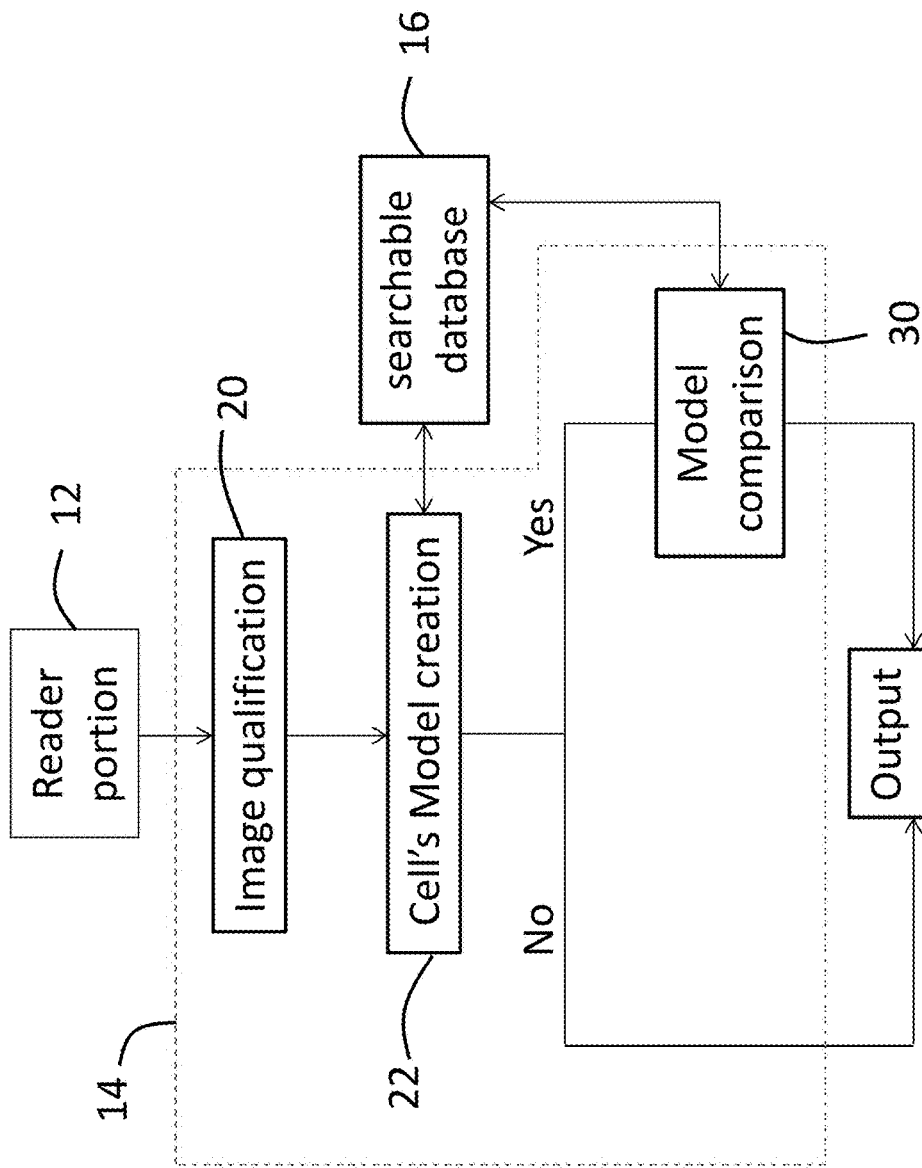
FIG. 6 is a flow diagram illustrating operations to be carried out within the HSV identification imaging system according to the present invention.

FIG. 6 is a flow diagram illustrating operations in the HSV identification imaging system 10, especially in the image analyzer/processor 14, in accordance with an embodiment of the present invention. The process begins when the image analyzer/processor 14 receives image data from reader portion 12. After the image data is received, a series of image qualification functions are performed by the image analyzer/processor 14 to clarify the image data, as indicated in block 20 in FIG. 6.

Figure 7:
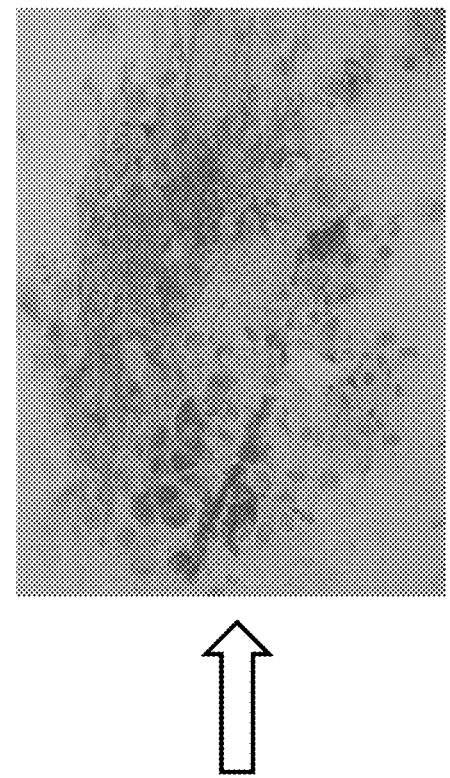
FIG. 7 shows a change from a non-clean cell's image to a clean cell image by a corrected action.
Figure 7:
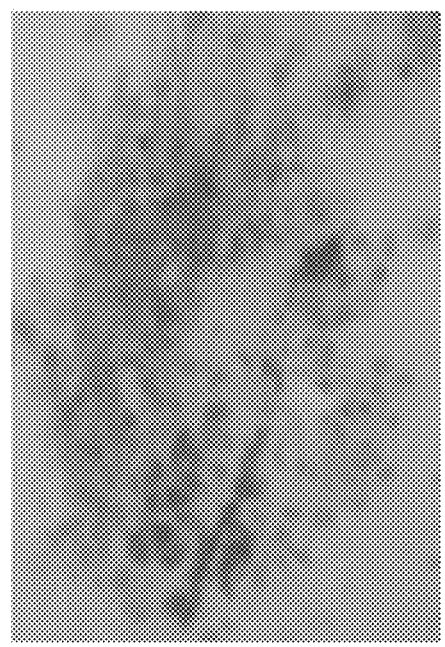

The step 20 of image qualification involves quickly processing a fraction of the available image data to ensure that the received image data is of sufficient quality to proceed with the following processing. In one embodiment, if the step 20 of image qualification leads to a conclusion that the image data has bad quality or inadequacies, a focus or aperture of the microscope may be automatically adjusted and then the reader portion 12 may be instructed to recapture new image data of the tissue sample from the patient's skin, tumor, inflammation or polyps until the inadequacies have been corrected. Referring to FIG. 7, when blurred image data (at the left side of FIG. 7) of the tissue samples from the patient's skin, tumor, inflammation or polyps are captured by the reader portion 12 and the image data is determined in the step 20 to have a bad quality or inadequacies, a focus or aperture of the microscope may be automatically adjusted and then the reader portion 12 may be instructed to recapture new image data of the tissue sample from the patient's skin, tumor, inflammation or polyps until the inadequacies have been corrected, as seen at the right side of FIG. 7. Furthermore, one or two portions, each of which may have an area of between 5×5 µm$^2$ and 200×200 µm$^2$ or between 50×50 µm$^2$ and 1000×1000 µm$^2$, of the image data may be used to determine the image data are blurred or clear in real time.

Figure 8:
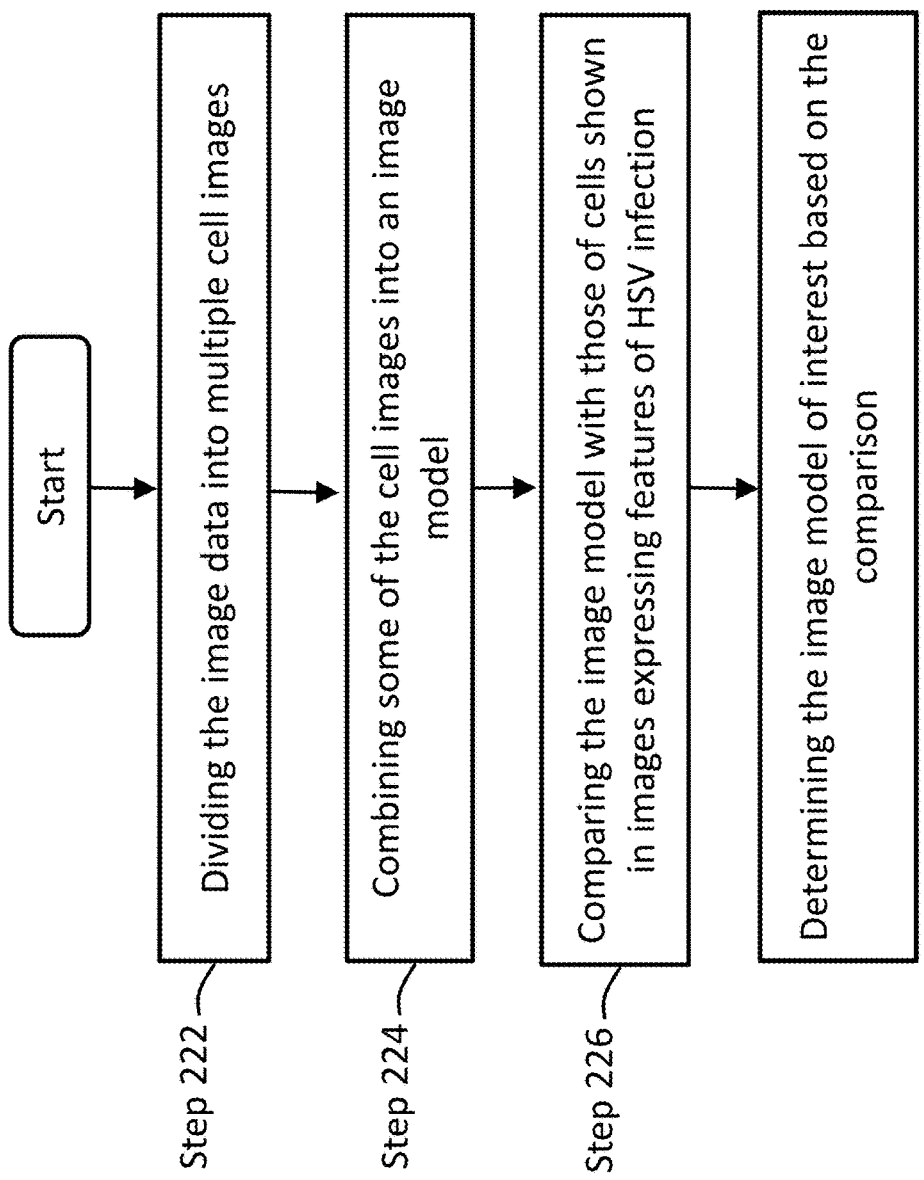
FIG. 8 is a flow chart of creating image models of interest.

Upon the image data being determined in the step 20 to have a good quality or no inadequacies, as illustrate in block 22 in FIG. 6, multiple image models are created. Referring to FIG. 8, the step 22 of creating image models of interest may include:

step 222: dividing the image data, such as an image of the tissue sample from the patient skin, tumor, inflammation or polyps, into multiple cell images;

step 224: combining some of the cell images, such as those arranged in a 10*10 grid, in a 50*50 grid or in another grid having more than 2 rows and 2 columns into an image model; and step 224: comparing a color and/or a partial profile of a cell shown in each cell image in the image model with those of cells shown in images expressing features of HSV infection stored in the searchable database 16 so as to determine if the image model is one of interest based on the number of the cell images in the image model having features as shown in the images expressing features of HSV infection. The image model of interest may have an area of between 5×5 $\mu m^2$ and 20×20 $\mu m^2$ or between 50×50 $\mu m^2$ and 200×200 $\mu m^2$.

Figure 9:
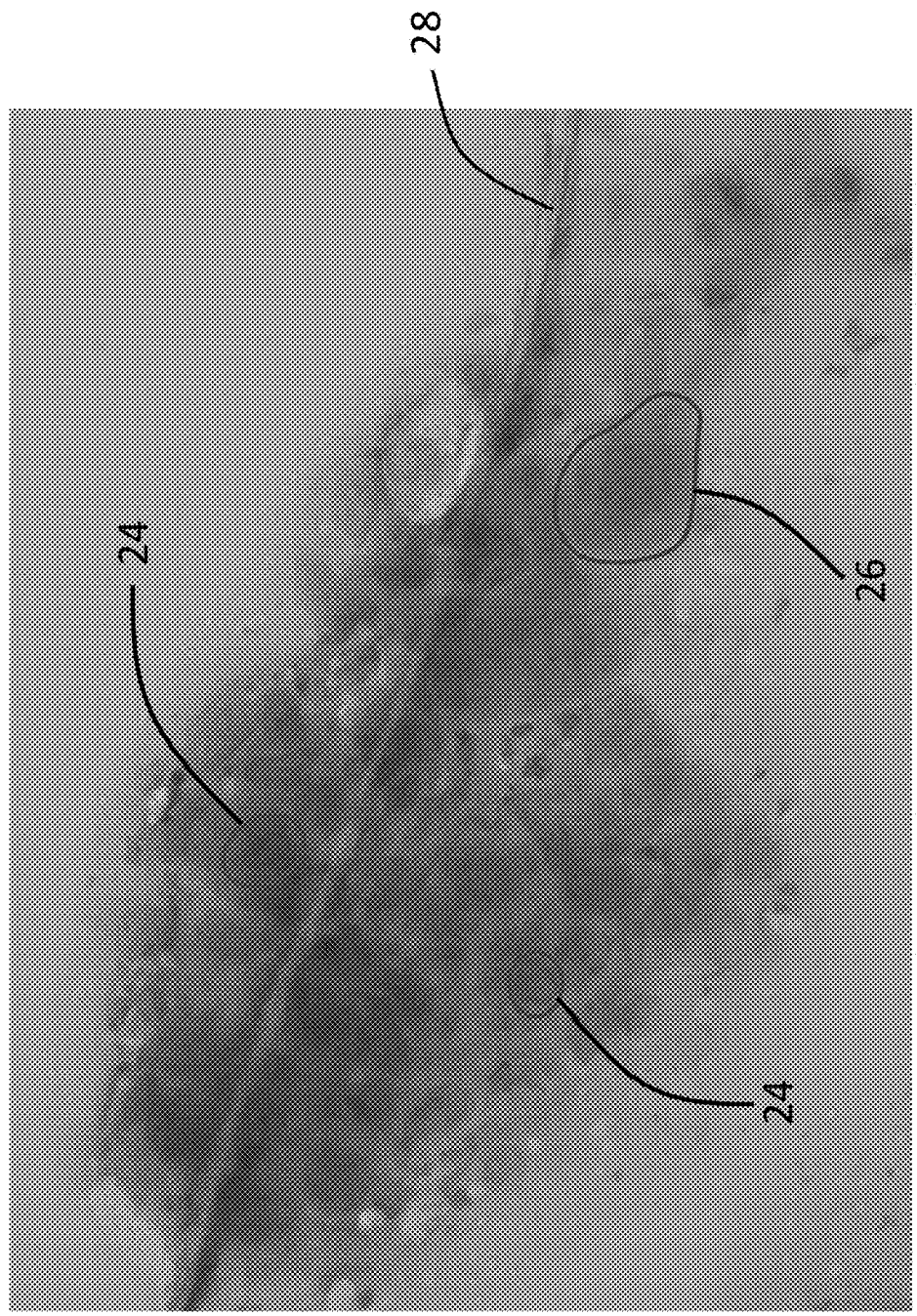
FIG. 9 is a photomicrograph of HSV infected cells showing the balloon cells (BCs) and giant cells (GCs).

Please refer to FIG. 9, which shows the step of cell's model creation in accordance with an embodiment of the present invention. As shown in FIG. 9, the balloon cells (BCs) 24 and the giant cells (GCs) 26 are in an infected nerve end organ 28. The swollen nuclei of the balloon cells (BCs) 24 are slate gray and ground glass in appearance due to margination of the nuclear chromatin. BCs 24 fuse to form giant cells GCs 26. Many nuclei are present in the GCs 26 (original magnification ×400). The image model of interest may express cell images showing a continuous profile of a complete cell of interest, such as complete balloon cell 24 or complete giant cell 26, or a continuous profile of an infected area or showing a continuous profile of a part of a cell of interest, such as balloon cell 24 or giant cell 26.

If no image model is determined of interest, a "non-HSV infection" message may be output from the output device 18, such as screen or printer.

If one or more of the image models derived from the image data are determined of interest in the step 22 of model creation, a step 30 of model comparison may be performed to compare the image model of interest with image models of HSV infection, stored in the searchable database 16, so as to determine if the image model of interest is indicative of a HSV-infected cell. The step 30 of model comparison may include:

(1) shifting and/or rotating the image model of interest; and (2) comparing the image model of interest with image models of HSV infection, stored in the searchable database 16, so as to determine if the image model of interest is indicative of a HSV-infected cell. Accordingly, a score representing similarity between the image model of interest and one or more of the image model of HSV infection may be output to the output device 18, and then a message of "HSV infection" may be output from the output device 18.

The image model of interest may be compared with all of the image models of HSV infection stored in the searchable database 16. Alternatively, the image models of HSV infection may be previously sorted based on the features expressed by the image models of HSV infection, and the image models of HSV infection expressing the same features as the image model of interest expresses may be selected from the searchable database 16 to be compared with the image model of interest.

The anti-cancer treatment, as illustrated in the steps 310 and 312, may include the following treatment as below:

(1) Surgery: In theory, non-hematological cancers can be cured if entirely removed by surgery, but this is not always possible. When the cancer has metastasized to other sites in the body prior to surgery, complete surgical excision is usually impossible. In the Halstedian model of cancer progression, tumors grow locally, then spread to the lymph nodes, then to the rest of the body. This has given rise to the popularity of local-only treatments such as surgery for small cancers. Even small localized tumors are increasingly recognized as possessing metastatic potential. Examples of surgical procedures for cancer include mastectomy for breast cancer, prostatectomy for prostate cancer, and lung cancer surgery for non-small cell lung cancer. The goal of the surgery can be either the removal of only the tumor, or the entire organ. A single cancer cell is invisible to the naked eye but can regrow into a new tumor, a process called recurrence. For this reason, the pathologist will examine the surgical specimen to determine if a margin of healthy tissue is present, thus decreasing the chance that microscopic cancer cells are left in the patient. In addition to removal of the primary tumor, surgery is often necessary for staging, e.g. determining the extent of the disease and whether it has metastasized to regional lymph nodes. Staging is a major determinant of prognosis and of the need for adjuvant therapy. Occasionally, surgery is necessary to control symptoms, such as spinal cord compression or bowel obstruction. This is referred to as palliative treatment. If surgery is possible and appropriate, it is commonly performed before other forms of treatment, although the order does not affect the outcome. In some instances, surgery must be delayed until other treatments are able to shrink the tumor.

(2) Radiation therapy: Radiation therapy (also called radiotherapy, X-ray therapy, or irradiation) is the use of ionizing radiation to kill cancer cells and shrink tumors. Radiation therapy can be administered externally via external beam radiotherapy (EBRT) or internally via brachytherapy. The effects of radiation therapy are localized and confined to the region being treated. Radiation therapy injures or destroys cells in the area being treated (the "target tissue") by damaging their genetic material, making it impossible for these cells to continue to grow and divide. Although radiation damages both cancer cells and normal cells, most normal cells can recover from the effects of radiation and function properly. The goal of radiation therapy is to damage as many cancer cells as possible, while limiting harm to nearby healthy tissue. Hence, it is given in many fractions, allowing healthy tissue to recover between fractions. Radiation therapy may be used to treat almost every type of solid tumor, including cancers of the brain, breast, cervix, larynx, oral, lung, pancreas, prostate, skin, stomach, uterus, or soft tissue sarcomas. Radiation is also used to treat leukemia and lymphoma. Radiation dose to each site depends on a number of factors, including the radio sensitivity of each cancer type and whether there are tissues and organs nearby that may be damaged by radiation.

(3) Chemotherapy: Chemotherapy is the treatment of cancer with drugs ("anticancer drugs") that can destroy cancer cells. In current usage, the term "chemotherapy" usually refers to cytotoxic drugs which affect rapidly dividing cells in general, in contrast with targeted therapy (see below). Chemotherapy drugs interfere with cell division in various possible ways, e.g. with the duplication of DNA or the separation of newly formed chromosomes. Most forms of chemotherapy target all rapidly dividing cells and are not specific to cancer cells, although some degree of specificity may come from the inability of many cancer cells to repair DNA damage, while normal cells generally can. Hence, chemotherapy has the potential to harm healthy tissue, especially those tissues that have a high replacement rate (e.g. intestinal lining). These cells usually repair themselves after chemotherapy. Because some drugs work better together than alone, two or more drugs are often given at the same time. This is called "combination chemotherapy"; most chemotherapy regimens are given in a combination. The treatment of some leukaemias and lymphomas requires the use of high-dose chemotherapy, and total body irradiation (TBI). This treatment ablates the bone marrow, and hence the body's ability to recover and repopulate the blood. For this reason, bone marrow, or peripheral blood stem cell harvesting is carried out before the ablative part of the therapy, to enable "rescue" after the treatment has been given. This is known as autologous stem cell transplantation. Alternatively, hematopoietic stem cells may be transplanted from a matched unrelated donor (MUD).

(4) Targeted therapies: Targeted therapy, which first became available in the late 1990s, has had a significant impact in the treatment of some types of cancer, and is currently a very active research area. This constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors imatinib (Gleevec/Glivec) and gefitinib (Iressa). Monoclonal antibody therapy is another strategy in which the therapeutic agent is an antibody which specifically binds to a protein on the surface of the cancer cells. Examples include the anti-HER2/neu antibody trastuzumab (Herceptin) used in breast cancer, and the anti-CD20 antibody rituximab, used in a variety of B-cell malignancies. Targeted therapy can also involve small peptides as "homing devices" which can bind to cell surface receptors or affected extracellular matrix surrounding the tumor. Radionuclides which are attached to these peptides (e.g. RGDs) eventually kill the cancer cell if the nuclide decays in the vicinity of the cell. Especially oligo- or multimers of these binding motifs are of great interest, since this can lead to enhanced tumor specificity and avidity. Photodynamic therapy (PDT) is a ternary treatment for cancer involving a photosensitizer, tissue oxygen, and light (often using lasers). PDT can be used as treatment for basal cell carcinoma (BCC) or lung cancer; PDT can also be useful in removing traces of malignant tissue after surgical removal of large tumors.

(5) Immunotherapy: Cancer immunotherapy refers to a diverse set of therapeutic strategies designed to induce the patient's own immune system to fight the tumor. Contemporary methods for generating an immune response against tumors include intravesical BCG immunotherapy for superficial bladder cancer, and use of interferon and other cytokines to induce an immune response in renal cell carcinoma and melanoma patients. Vaccines to generate specific immune responses are the subject of intensive research for a number of tumours, notably malignant melanoma and renal cell carcinoma. Sipuleucel-T is a vaccine-like strategy in late clinical trials for prostate cancer in which dendritic cells from the patient are loaded with prostatic acid phosphatase peptides to induce a specific immune response against prostate-derived cells. Allogeneic hematopoietic stem cell transplantation ("bone marrow transplantation" from a genetically non-identical donor) can be considered a form of immunotherapy, since the donor's immune cells will often attack the tumor in a phenomenon known as graft-versus-tumor effect. For this reason, allogeneic HSCT leads to a higher cure rate than autologous transplantation for several cancer types, although the side effects are also more severe. The cell based immunotherapy in which the patient's own Natural Killer cells (NK) and Cytotoxic T-Lymphocytes (CTL) are used has been in practice in Japan since 1990. NK cells and CTLs primarily kill the cancer cells when they are developed. This treatment is given together with the other modes of treatment such as Surgery, radiotherapy or Chemotherapy and called as Autologous Immune Enhancement Therapy (AIET).

(6) Hormonal therapy: The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial.

(7) Angiogenesis inhibitors: Angiogenesis inhibitors prevent the extensive growth of blood vessels (angiogenesis) that tumors require to survive. Some, such as bevacizumab, have been approved and are in clinical use. One of the main problems with anti-angiogenesis drugs is that many factors stimulate blood vessel growth in cells normal or cancerous. Anti-angiogenesis drugs only target one factor, so the other factors continue to stimulate blood vessel growth. Other problems include route of administration, maintenance of stability and activity and targeting at the tumor vasculature.

Multiple methods to take a tissue biopsy, as illustrated in the step 302, from a viscus of the patient are mentioned as below:

Excision biopsy: A whole organ or a whole lump is removed (excised). These are less common now, since the development of fine needle aspiration (see below). Some types of tumors (such as lymphoma, a cancer of the lymphocyte blood cells) have to be examined whole to allow an accurate diagnosis, so enlarged lymph nodes are good candidates for excisional biopsies. Some surgeons prefer excisional biopsies of most breast lumps to ensure the greatest diagnostic accuracy. Some organs, such as the spleen, are dangerous to cut into without removing the whole organ, so excisional biopsies are preferred for these.

Incisional biopsy: Only a portion of the lump is removed surgically. This type of biopsy is most commonly used for tumors of the soft tissues (muscle, fat, connective tissue) to distinguish benign conditions from malignant soft tissue tumors, called sarcomas.

Endoscopic biopsy: This is probably the most commonly performed type of biopsy. It is done through a fiberoptic endoscope the doctor inserts into the gastrointestinal tract (alimentary tract endoscopy), urinary bladder (cystoscopy), abdominal cavity (laparoscopy), joint cavity (arthroscopy), mid-portion of the chest (mediastinoscopy), or trachea and bronchial system (laryngoscopy and bronchoscopy), either through a natural body orifice or a small surgical incision. The endoscopist can directly visualize an abnormal area on the lining of the organ in question and pinch off tiny bits of tissue with forceps attached to a long cable that runs inside the endoscope.

Colposcopic biopsy: This is a gynecologic procedure that typically is used to evaluate a patient who has had an abnormal Pap smear. The colposcope is actually a close-focusing telescope that allows the physician to see in detail abnormal areas on the cervix of the uterus, so that a good representation of the abnormal area can be removed and sent to the pathologist.

Fine-needle aspiration biopsy: Fine-needle aspiration biopsy (FNAB, FNA or NAB), or fine-needle aspiration cytology (FNAC), is a diagnostic procedure used to investigate superficial (just under the skin) lumps or masses. In this technique, a thin, hollow needle is inserted into the mass for sampling of cells that, after being stained, will be examined under a microscope. There could be cytology exam of aspirate (cell specimen evaluation, FNAC) or histological (biopsy—tissue specimen evaluation, FNAB). Fine-needle aspiration biopsies are very safe, minor surgical procedures. Often, a major surgical (excisional or open) biopsy can be avoided by performing a needle aspiration biopsy instead. Today, this procedure is widely used in the diagnosis of cancer. A needle aspiration biopsy is safer and less traumatic than an open surgical biopsy, and significant complications are usually rare, depending on the body site. Common complications include bruising and soreness. There is a risk, because the biopsy is very small (only a few cells), that the problematic cells will be missed, resulting in a false negative result. There is also a risk that the cells taken will not enable a definitive diagnosis.

A needle no wider than that typically used to give routine injections (about 22 gauge) is inserted into a lump (tumor), and a few tens to thousands of cells are drawn up (aspirated) into a syringe. These are smeared on a slide, stained, and examined under a microscope by the pathologist. A diagnosis can often be rendered in a few minutes. Tumors of deep, hard-to-get-to structures (pancreas, lung, and liver, for instance) are especially good candidates for FNA, as the only other way to sample them is with major surgery. Such FNA procedures are typically done by a radiologist under guidance by ultrasound or computed tomography (CT scan) and require no anesthesia, not even local anesthesia. Thyroid lumps are also excellent candidates for FNA.

Punch biopsy: This technique is typically used by dermatologists to sample skin rashes and small masses. After a local anesthetic is injected, a biopsy punch, which is basically a small (3 or 4 mm in diameter) version of a cookie cutter, is used to cut out a cylindrical piece of skin. The hole is typically closed with a suture and heals with minimal scarring.

Bone marrow biopsy: In cases of abnormal blood counts, such as unexplained anemia, high white cell count, and low platelet count, it is necessary to examine the cells of the bone marrow. In adults, the sample is usually taken from the pelvic bone, typically from the posterior superior iliac spine. This is the prominence of bone on either side of the pelvis underlying the "bikini dimples" on the lower back/upper buttocks. Hematologists do bone marrow biopsies all the time, but most internists and pathologists and many family practitioners are also trained to perform this procedure.

With the patient lying on his/her stomach, the skin over the biopsy site is deadened with a local anesthetic. The needle is then inserted deeper to deaden the surface membrane covering the bone (the periosteum). A larger rigid needle with a very sharp point is then introduced into the marrow space. A syringe is attached to the needle and suction is applied. The marrow cells are then drawn into the syringe. This suction step is occasionally uncomfortable, since it is impossible to deaden the inside of the bone. The contents of the syringe, which to the naked eye looks like blood with tiny chunks of fat floating around in it, is dropped onto a glass slide and smeared out. After staining, the cells are visible to the examining pathologist or hematologist.

This part of procedure, the aspiration, is usually followed by the core biopsy, in which a slightly larger needle is used to extract core of bone. The calcium is removed from the bone to make it soft, the tissue is processed and tissue sections are made. Even though the core biopsy procedure involves a bigger needle, it is usually less painful than the aspiration.

For ensuring the safety (no significant side-effects or damages to the human, for example, leukocyte, liver or kidney) of the anti-cancer, anti-HSV and/or anti-inflammation treatment in the steps 106, 310, 312, 314, 316, 322 and 324, data about leukocyte, liver and kidney functions related to the patient before and after taking or being subjected to the anti-cancer, anti-HSV and/or anti-inflammation treatments in the steps 106, 310, 312, 314, 316, 322 and 324 may need to be obtained as an option. The data about leukocyte, liver and kidney functions related to the patient before taking or being subjected to the anti-cancer, anti-HSV and/or anti-inflammation treatments in the steps 106, 310, 312, 314, 316, 322 and 324 are defined as first data LK1, and the data about leukocyte, liver and kidney functions related to the subject after taking or being subjected to the anti-cancer, anti-HSV and/or anti-inflammation treatments in the steps 106, 310, 312, 314, 316, 322 and 324 are defined as second data LK2. Each piece of the first and second data LK1 and LK2 may include, but not limited to, (1) data about white blood cell count (2) data about kidney functions (such as blood urea nitrogen (BUN), glomerular filtration rate (GFR), creatinine, creatinine clearance rate (CCR), albumin/urine creatinine ratio (ACR), cystatin C, uric acid, microalbumin, urine routine, and/or urine sediment), and (3) data about liver functions (such as aspartate aminotransferase (AST), alanine aminotransferase (ALT), α-fetoprotein (AFP), total bilirubin, direct bilirubin, indirect bilirubin, albumin, globulin, albumin/globulin ratio, γ-glutamyltranspeptidase (γ-GT), alkaline phosphatase (ALP), prothrombin time (PT), HBsAg, Anti-HBs, and/or Anti-HCV). AST is also called glutamic oxaloacetic transaminase (GOT), serum glutamic-oxaloacetic transaminase (SGOT), or aspartate aminotransferase (ASAT). ALT is also called alanine aminotransferase (ALAT), serum glutamic-pyruvic transaminase (SGPT), or glutamic pyruvic transaminase (GPT).

By comparing the second data LK2 with the first data LK1, the difference between the first and second data LK1 and LK2 can be obtained to identify or evaluate the effect of the anti-cancer, anti-HSV and/or anti-inflammation treatments in the steps 106, 310, 312, 314, 316, 322 and 324 on the leukocyte, liver and kidney of the patient, as mentioned below.

If there is no (significant) difference between the first and second data LK1 and LK2, it could mean the anti-cancer, anti-HSV and/or anti-inflammation treatments in the steps 106, 310, 312, 314, 316, 322 and 324 are harmless to the leukocyte, liver and kidney of the subject.

If the second data LK2 is (much or significantly) better than the first data LK1, it could mean the anti-cancer, anti-HSV and/or anti-inflammation treatments in the steps 106, 310, 312, 314, 316, 322 and 324 are harmless but beneficial to the leukocyte, liver and/or kidney of the subject.

If the second data LK2 is a little worse than the first data LK1, it could mean the anti-cancer, anti-HSV and/or anti-inflammation treatments in the steps 106, 310, 312, 314, 316, 322 and 324 are slightly harmful to the leukocyte, liver and/or kidney of the subject.

If the second data LK2 is much or significantly worse than the first data LK1, it could mean the anti-cancer, anti-HSV and/or anti-inflammation treatments in the steps 106, 310, 312, 314, 316, 322 and 324 are significantly harmful to the leukocyte, liver and/or kidney of the subject.

Anti-HSV Treatment

The anti-HSV treatment, as illustrated in the steps 310, 314, 316 and 322, may include taking an anti-HSV agent mentioned as below:

Early treatment with antiviral agents can reduce morbidity and prevent complications. According to one feature of the present anti-HSV agent provide the compound of formula (I)

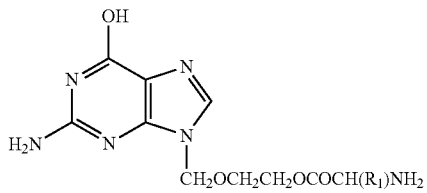

wherein $R_1$ represents a group of formula $-CH[CH_3]_2$ and pharmaceutically acceptable salts thereof. The compound of formula (I) can also be named as 2-[(2-amino-6-oxo-6,9-dihydro-3H-purin-9-yl)methoxy]ethyl-2-amino-3-methylbutanoate. As used herein, the compounds according to the anti-HSV agent will be intended to include the compound of formula (I) and its pharmaceutically acceptable salts.

The pharmaceutically acceptable salts of the compound of formula (I) are preferably acid addition salts derived from an appropriate acid, e.g. hydrochloric, sulphuric, phosphoric, maleic, fumaric, citric, tartaric, lactic, acetic or p-toluene-sulphonic acid. Particularly preferred salts are the hydrochloride salts of compound of formula (I).

The compounds according to the anti-HSV agent may be prepared in conventional manner, e.g., by a process as described below.

Thus, according to a further feature of the present anti-HSV agent provide a process for the preparation of the compound of formula (I) above and pharmaceutically acceptable salts thereof which comprises (a) reacting a compound of formula (II)

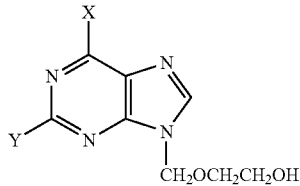

wherein X is an optionally protected hydroxy group, and Y is an optionally protected amino group with an optionally protected valine or a functional equivalent thereof;

(b) converting a compound of formula (III)

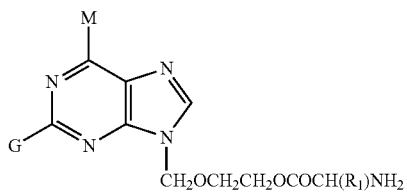

(wherein $R_1$ is as defined above; and M represents a hydroxy group and G represents an atom or group that can be replaced by or converted to an amino group; or G represents an amino group and M represents an atom or group that can be replaced by or converted to a hydroxy group) into a compound of formula (I) or a pharmaceutically acceptable salt thereof; or (c) reacting a compound of formula (IV)

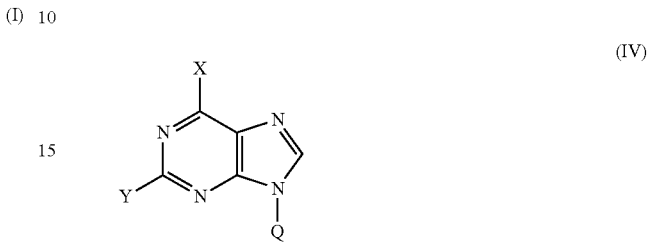

(wherein X and Y are as defined above and Q represents a leaving atom or group) with a compound of formula (V)

$$ACH_2OCH_2CH_2OCOCH(R_1)R_2 \quad (V)$$

(wherein $R_1$ is as defined above, A represents a leaving group or atom and $R_2$ is an optionally protected amino group); and optionally effecting one or more of the following conversions;

(i) removal of any protecting groups;
(ii) where the resulting product is a compound of formula (I), conversion of the said compound into a pharmaceutically acceptable salt thereof; and
(iii) where the resulting product is a pharmaceutically acceptable salt of a compound of formula (I), conversion of the said salt into the parent compound.

With regard to process (a), the esterification reaction may be carried out in conventional manner, for example in a solvent such as pyridine or dimethylformamide in the presence of a coupling agent such as N,N'-dicyclohexylcarbodiimide, optionally in the presence of a catalytic base such as 4-dimethylaminopyridine. The water formed during the reaction may, if desired, be removed in conventional manner, for example by distillation or by the addition of a water-binding substance. Subsequently, the ester obtained as reaction product may be isolated in conventional manner.

As an alternative to the use of valine per se, a functional equivalent of the acid may be employed, e.g., an acid halide such as the acid chloride, or an acid anhydride. In such a case in order to avoid undesirable side-reactions, it is advantageous to use an amino-protected derivative. Examples of preferred amino-protecting groups including acyl, e.g., $C_{1-4}$ alkanoyl such as acetyl and aryloxycarbonyl, e.g., benzyloxy carbonyl. A suitable amino-protected derivative, for example, is one wherein the amino group of the amino acid is replaced by an azido group.

Conversion of a compound of formula (III) into a compound of formula (I), by method (b), can be achieved by various means. For example G may represent an azide group which can be reduced to an amino group by catalytic hydrogenation, using a suitable catalyst such as palladium on carbon. Alternatively, G may each represent a halogen atom or an alkylthio or alkylsulphonyl group which can be converted to an azide group which in turn can be converted to an amino group by catalytic hydrogenation using, for example, hydrogen in the presence of palladium on carbon. For the preparation of the compound of formula (I), a compound of formula (III) wherein M is an amino group may be converted to a hydroxy group for example by treatment with a deaminating enzyme such as adenosine deaminase.

In process (c), the group Q in formula (IV) may, for example, represent a hydrogen atom; an acyl group, e.g. a $C_{1-4}$ alkanoyl group such as an acetyl group or an aroyl group such an a benzoyl group; or a tri-$C_{1-4}$ alkylsilyl group such as a trimethylsilyl group. The group A in formula (V) may, for example, represent a halogen atom (e.g. chlorine) or an acyloxy group wherein the acyl moiety may be, for example, a $C_{1-4}$ alkanoyl group such as acetyl or an aroyl group such as benzoyl. The group $R_2$ may represent an amino-protecting group such as for example, $C_{1-4}$ alkanoyl (e.g., acetyl) or aryloxycarbanoyl (e.g., benzyloxycarbonyl) it may also represent an azido group. The reaction may be conveniently effected in a strong polar solvent such as dimethylformamide or hexamethylphosphoramide, advantageously in the presence of a base such as triethylamine or potassium carbonate. Alternatively, a thermal condensation may be effected by heating the compounds of formulae (IV) and (V) in the presence of a catalytic amount of a strong acid, e.g., sulphuric acid.

Compounds of formulae (II) to (V), employed as intermediates in the synthesis of the compound of formula (I), can be prepared in conventional manner, e.g., by procedures described in U.K. Patent Specification No. 1523865. These methods rely on intermediates prepared from simply substituted purines, which may be available commercially, or prepared according to techniques which are well known per se and which are disclosed in the literature such as the aforementioned text-book. Thus, for example, compounds of formula (III) may be generally prepared by using an analogous procedure to that of process (c), i.e., reacting an appropriate purine with a compound of formula (V).

The optional conversions (i), (ii) and (iii) may be effected in conventional manner. Thus, for example, removal of protecting groups in conversion (i) may be effected by hydrolysis, solvolysis or hydrogenolysis as appropriate. With regard to removal of protecting groups on the amino acid acyl radicals, hydrogenolysis, e.g., of aryloxycarbonyl protecting groups, and conversion of azido group, e.g., by catalytic hydrogenation, e.g., using a palladium catalyst, are preferred. With regard to protection of the groups in the 2- and/or 6-positions of purine nucleus, these may be selected for example from arylmethyl groups, e.g., benzyl; or tri-$C_{1-4}$ alkylsilyl, e.g., trimethylsilyl. Arylmethyl blocking groups, may be removed for example by hydrogenolysis, e.g., by hydrogenation in the presence of Raney nickel or a palladium catalyst. Trialkylsilyl blocking groups may be removed for example by solvolysis, e.g., by alcoholysis.

The conversion of a compound of formula (I) into a pharmaceutically acceptable salt may be effected in conventional manner, for example, by treatment of the compound with an appropriate acid to form an acid addition salt, for example, by lyophilisation of a methanolic solution of the parent ester with an acid solution.

Similarly, conversion of a salt into the parent compound of formula (I) may be effected in conventional manner.

The present anti-HSV agent, or the combination thereof also provides the compounds of formula (I) and pharmaceutically acceptable salts thereof (hereinafter identified as "the active compounds") for use in medical therapy, e.g., in the treatment of a viral disease in an animal, e.g., a mammal such as a human. The compounds are especially useful for the treatment of diseases caused by various DNA viruses, such as herpes infections, for example, herpes simplex, varicella or zoster, cytomegalovirus as well as diseases caused by hepatitis B or Epstein-Barr viruses or human herpes virus-6 (HHV-6). The active compounds, i.e. the anti-HSV agent, can also be used for the treatment of papilloma or wart virus infections, for example, for the treatment of cervical cancer and oral cancer. Besides, the active compounds, i.e. the anti-HSV agent, can be used for the treatment of retrovirus infections such as HIV infections in synergistic combination with anti-HIV agents.

In addition to their use in human medical therapy, the compounds of formula (I) can be administered to other animals for treatment of viral diseases, e.g., in other mammals. For example, the active compounds are especially useful for the treatment of equine rhinopneumonitis.

The present anti-HSV agent also provides a method for the treatment of a viral disease in an animal, e.g., a mammal such as a human, which comprises administering to the animal an effective antiviral amount of a compound of formula (I) or a pharmaceutically acceptable salt thereof.

The present anti-HSV agent also provides the use of a compound of formula (I) in the manufacture of a medicament for the treatment of a viral infection.

The active compounds may be administered by any route appropriate to the condition to be treated, suitable routes including oral, rectal, nasal, topical (including buccal and sublingual) vaginal and parenteral (including subcutaneous, intramuscular, intravenous, intradermal, intrathecal and epidural). It will be appreciated that the preferred route may vary with for example the condition of the recipient.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable effective dose will be in the range 0.1 to 250 mg per kilogram bodyweight of recipient per day, preferably in the range 1 to 100 mg per kilogram bodyweight per day and most preferably in the range 5 to 20 mg per kilogram bodyweight per day; an optimum dose is about 10 mg per kilogram bodyweight per day. (Unless otherwise indicated, all weights of active ingredient are calculated as the parent compound of formula (I): for salts thereof the figures would be increased proportionately.) The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

The compounds of the present anti-HSV agent may be administered alone or in combination with other therapeutic agents, for example, with 2-Amino-1,9-dihydro-9-((2-hydroxyethoxy)methyl)-6H-purin-6-one (acyclovir) or 2-[(2-amino-6-oxo-6,9-dihydro-3H-purin-9-yl)methoxy]ethyl-2-amino-3-methylbutanoate (valacyclovir) used to treat herpes virus infections in particular HSV.

The acyclovir formula (VI) is showed below:

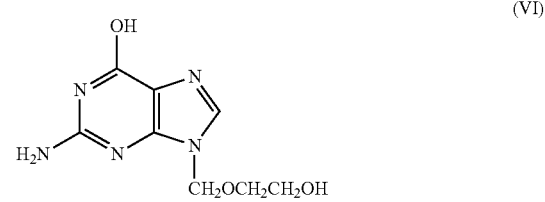

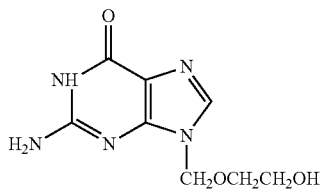

The valacyclovir formula (VII) is showed below:

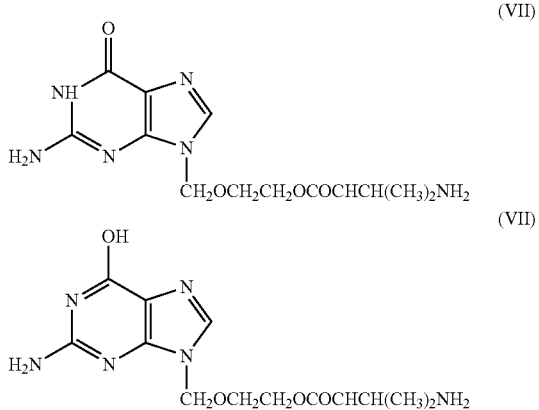

Acyclovir is an antiviral drug. It slows the growth and spread of the herpes virus so that the body can fight off the infection. Acyclovir will not cure herpes, but it can lessen the symptoms of the infection.

Acyclovir is used to treat infections caused by herpes viruses. Illnesses caused by herpes viruses include genital herpes, cold sores, shingles, and chicken pox.

Acyclovir differs from previous nucleoside analogues in containing only a partial nucleoside structure: the sugar ring is replaced with an open-chain structure. It is selectively converted into acyclo-guanosine monophosphate (cyclo-GMP) by viral thymidine kinase, which is far more effective (3000 times) in phosphorylation than cellular thymidine kinase. Subsequently, the monophosphate form is further phosphorylated into the active triphosphate form, acyclo-guanosine triphosphate (acyclo-GTP), by cellular kinases. Acyclo-GTP has approximately 100 times greater affinity for viral than cellular polymerase. As a substrate, acyclo-GTP is incorporated into viral DNA, resulting in premature chain termination. Although acyclovir resembles a nucleotide, it has no 3' end. Therefore, after its incorporation into a growing DNA strand, no further nucleotides can be added to this strand. It has also been shown that viral enzymes cannot remove acyclo-GTP from the chain, which results in inhibition of further activity of DNA polymerase. Acyclo-GTP is fairly rapidly metabolised within the cell, possibly by cellular phosphatases. In sum, acyclovir can be considered a prodrug: it is administered in an inactive (or less active) form and is metabolised into a more active species after administration.

Valacyclovir is a prodrug that is nearly completely converted to Acyclovir and L-valine. Due to its more efficient phosphorylation by viral thymidine kinase, Acyclovir's antiviral activity is greatest against herpes simplex virus type 1 (HSV-1), followed by herpes simplex virus type 2 (HSV-2), varicella-zoster virus (VZV), Epstein-Barr virus (EBV), and cytomegalovirus (CMV).

Valacyclovir is rapidly and nearly completely (99%) converted to the active compound, acyclovir, and L-valine by first-pass intestinal and hepatic metabolism by enzymatic hydrolysis. Acyclovir is converted to inactive metabolites by alcohol and aldehyde dehydrogenase and, to a small extent, by aldehyde oxidase. The metabolism of valacyclovir and acyclovir is not associated with hepatic microsomal enzyme systems.

While it is possible for the active ingredients to be administered alone, it is preferable to present them as pharmaceutical formulations. The formulations, both for veterinary and for human use, of the present anti-HSV agent comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers of finely divided solid carriers or both, and then, if necessary, shaping the product.

Formulations of the above-mentioned anti-HSV agent suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion; or as a preventive vaccine; or as a spray gas; or as a skin care products; or as a skin cleaning products. For some applications, the above-mentioned anti-HSV agent can be one of the ingredients in a shampoo or hair restorer for improving or curing user's Alopecia or preventing the user from catching Alopecia. The above-mentioned anti-HSV agent can be one of the ingredients in a soap, facial cleanser or cleaning cream for improving or curing user's dermatoses or for preventing the user from catching specific dermatoses. The active ingredient may also be presented as a bolus, electuary or paste.

Furthermore, the anti-HSV agent can include, for example, valacyclovir, penciclovir, famciclovir, Foscarnet, Cidofovir (HPMPC, GS-504), Trifluridine, Lobucavir, Crofelemer or Resiquimod except acyclovir and valacyclovir, but is not limited thereto.

Proposed dose of the antiviral agent prescribed for HSV infection:
1. Adult: Valacyclovir (500 mg)
    a. 2 tablets daily (i.e. 1 tablet after breakfast and dinner) for 5-7 days.
    b. 3 tablets daily (i.e. every 8 hours) for severe cases in the beginning only.
2. Children: Acyclovir granules 10 mg/KG, every 6 hours, for 5-7 days
3. Topical corticosteroids ointment or cream
4. The antiviral medications available to treat the pregnant woman infected with HSV are acyclovir, famciclovir and valacyclovir. Acyclovir has the most data on the safety of use in pregnancy. A registry of over 1000 pregnant women who were exposed to acyclovir during early pregnancy suggests that acyclovir is probably safe as there were no increases in birth defects. For example, the pregnant woman infected with HSV may take 2 or 3 tablets of valacyclovir (500 mg) daily (i.e. 1 tablet after breakfast and dinner) for 5-7 days. Alternatively, the pregnant woman infected with HSV may take 2 or 3 tablets of acyclovir (400 mg) daily (i.e. 1 tablet after breakfast and dinner) for 5-7 days. Alternatively, the pregnant woman infected with HSV may take 2 or 3 tablets of famciclovir (250 mg) daily (i.e. 1 tablet after breakfast and dinner) for 5-7 days.

This invention discloses these QTT-positive patients show remarkable response to antiviral agent. They could and should be treated promptly in order to prevent the latent state and being an infectious source.

Those described above are the embodiments to exemplify the present disclosure to enable the person skilled in the art to understand, make and use embodiments of the present disclosure. This description, however, is not intended to limit the scope of the present disclosure. Any equivalent modification and variation according to the spirit of the present disclosure is to be also included within the scope of the claims stated below.

The components, steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, benefits and advantages. These also include embodiments in which the components and/or steps are arranged and/or ordered differently.

In reading the present disclosure, one skilled in the art will appreciate that embodiments of the present disclosure can be implemented in hardware, software, firmware, or any combinations of such, and over one or more networks. Suitable software can include computer-readable or machine-readable instructions for performing methods and techniques (and portions thereof) of designing and/or controlling the fabrication and design of integrated circuit chips according to the present disclosure. Any suitable software language (machine-dependent or machine-independent) may be utilized.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. The scope of protection is limited solely by the claims. That scope is intended and should be interpreted to be as broad as is consistent with the ordinary meaning of the language that is used in the claims when interpreted in light of this specification and the prosecution history that follows and to encompass all structural and functional equivalents.

Those skilled in the art will readily observe that numerous modifications and alterations of the device and method may be made while retaining the teachings of the invention. Accordingly, the above disclosure should be construed as limited only by the metes and bounds of the appended claims.

New Indications for Clinical HSV Infection Cases

Figures 1A, 10:
Figures 1B, 10:
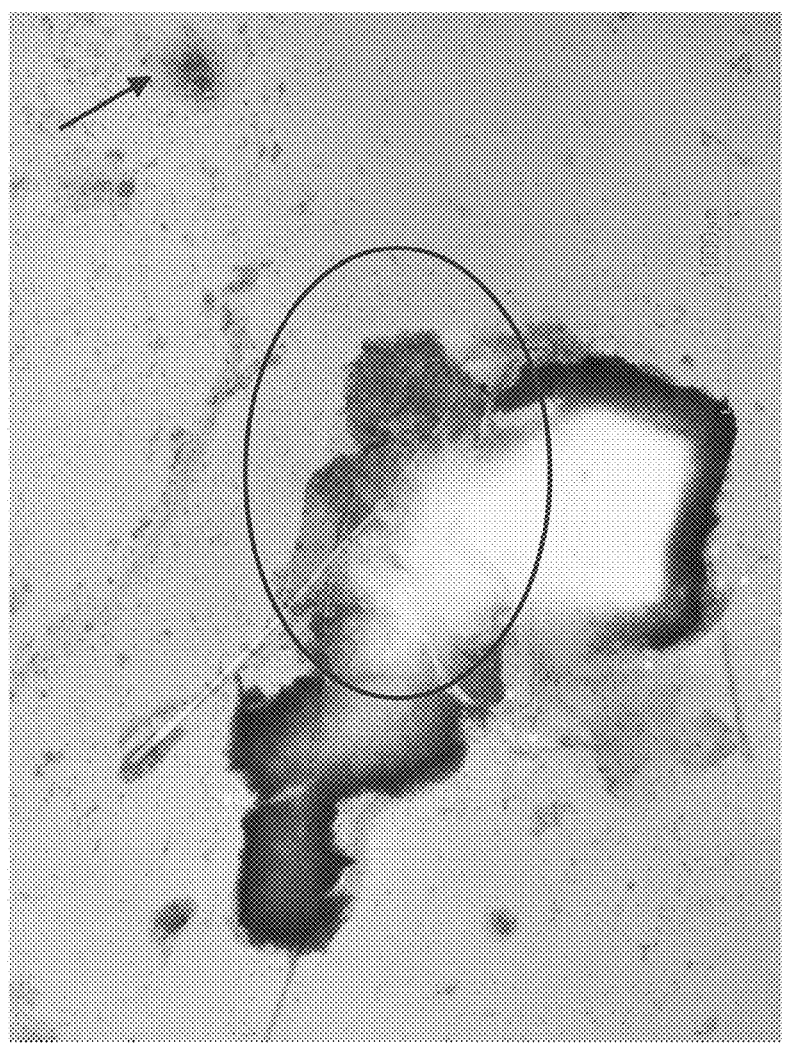

CASE 1: A 20-day-old newborn suffered from pin-sized vesiculopapules and pustules appearing over his forehead and extending to his cheeks and mandibles 10 days after his birth (FIG. 10-1a). Balloon degeneration of the squamous cells, intraepithelial vesicles and a balloon cells nest were observed by a QTT of a vesiculopapule (FIG. 10-1b). High power observation revealed that there were many eosinophils infiltrating between the BCs (FIG. 10-1b). The patient was treated with antiviral agent and TCS. His older brother suffered from HSV-associated dermatitis on his trunk 6 months after birth. His mother was diagnosed to have HSV-associated dermatitis when she was pregnant for her 2 boys. Her HSIgG titer was 12.5.

Figures 2A, 10:
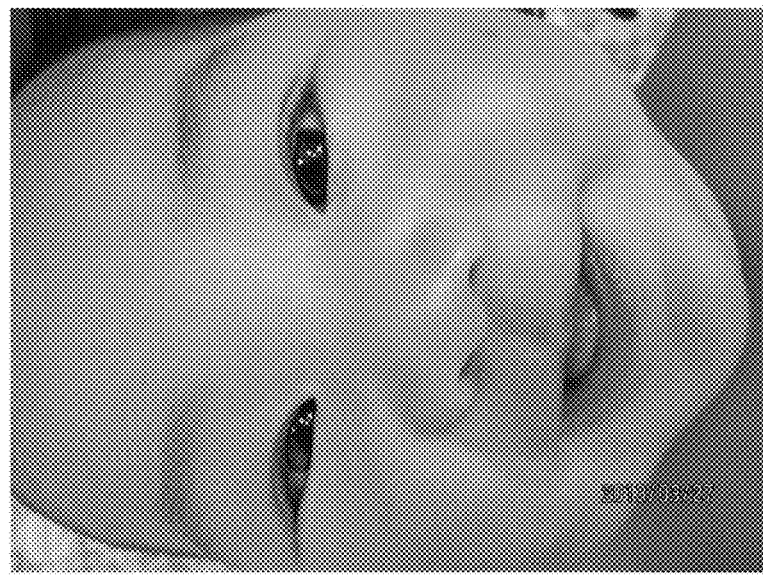

CASE 2: A 4-month-old newborn presented with a pustule over its right nostril (FIG. 10-2a). She began to suffered from itchy multiple vesiculopapules over her face and trunk since she was 2-month-old. Her mother had past history of HS vesicles over her forearm. This is the third episode of QTT-positive eruptions and the first time appeared with single lesion on face. Balloon degeneration of the follicular epithelium, a balloon cell and a giant cell were observed by QTT (FIG. 10-2b), which is compatible with cytologic finding of HS infection. The pustule and the concurrent itchy multiple vesiculopapules over her trunk responded to antiviral agents. There was no recurrence for 3 months till now.

Figures 2B, 10:
Figures 3A, 10:
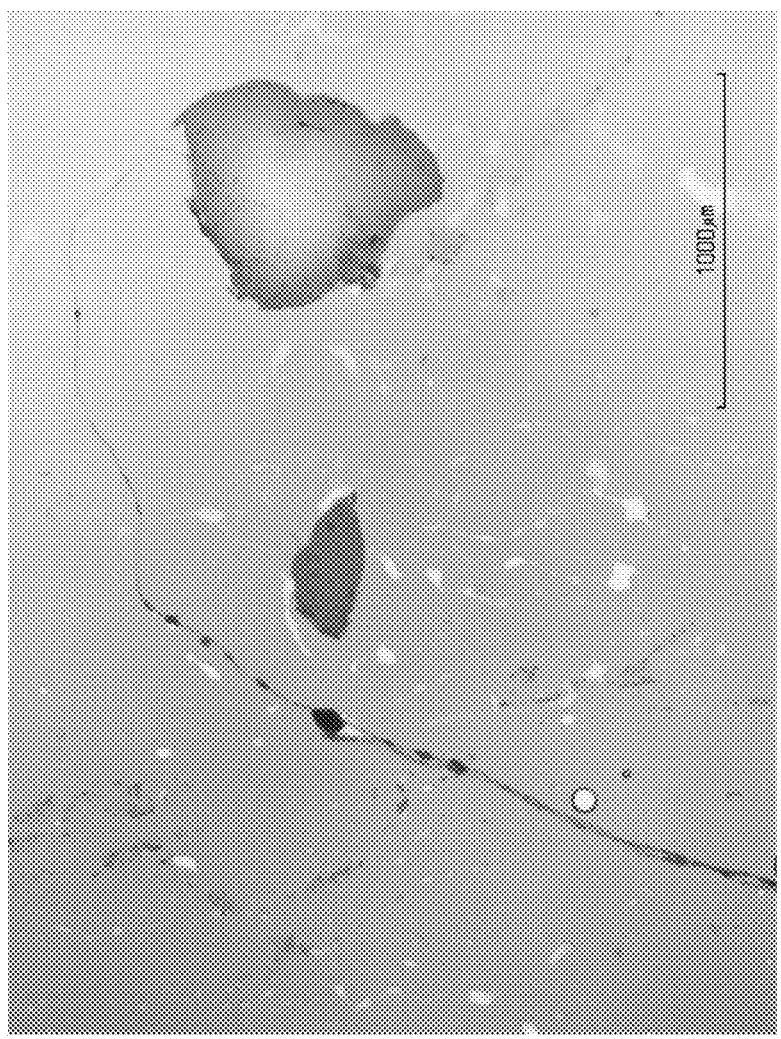
Figures 3B, 10:
Figures 3C, 10:
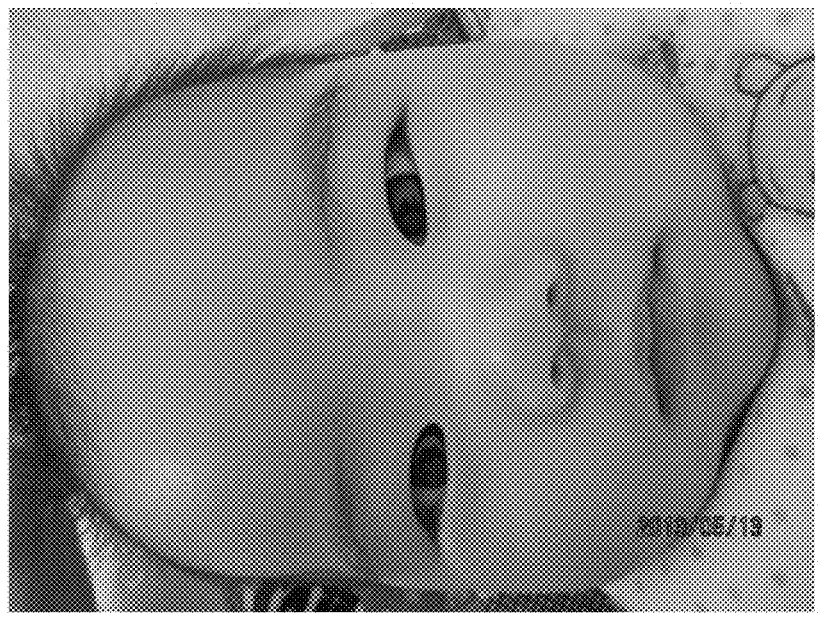
Figures 3D, 10:
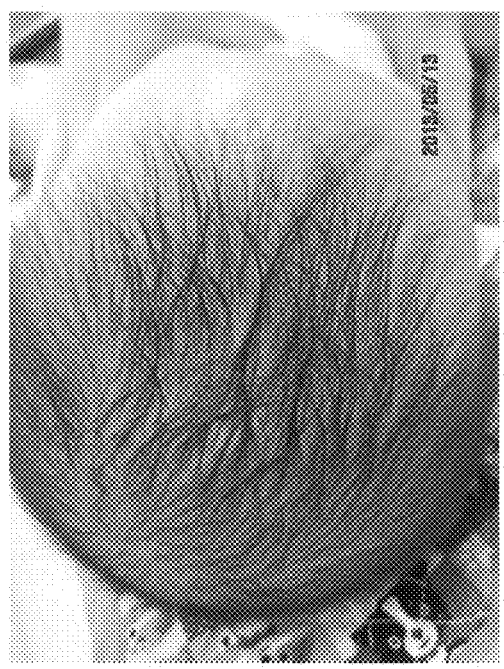

CASE 3: A 5-month-old newborn suffered from a crusted plaque over the frontal area of her scalp for 2 months. Many pin-sized vesiculopapules and pustules appearing over his cheeks 5 days ago. Dryness and scaliness around her mouth were also noted. QTT of vesiculopapules from her cheek revealed a nerve extending from the dermis (vesicular cavity) to its overlying epidermal sheet (FIG. 10-3a). Balloon degeneration of cells near the basement membrane and a giant cell with many pleomorphic nuclei were also observed under high power observation (FIG. 10-3b). The facial eruptions disappeared completely 3 days after the antiviral therapy (FIG. 10-3c). There were still some light-brown crust on the periphery of the frontal area (FIG. 10-3d). Her mother had past history of HS infection on her toes during pregnancy. Her father had a history of HS labialis for years and two episodes of HSV-associated dermatitis.

Figures 1A, 11:
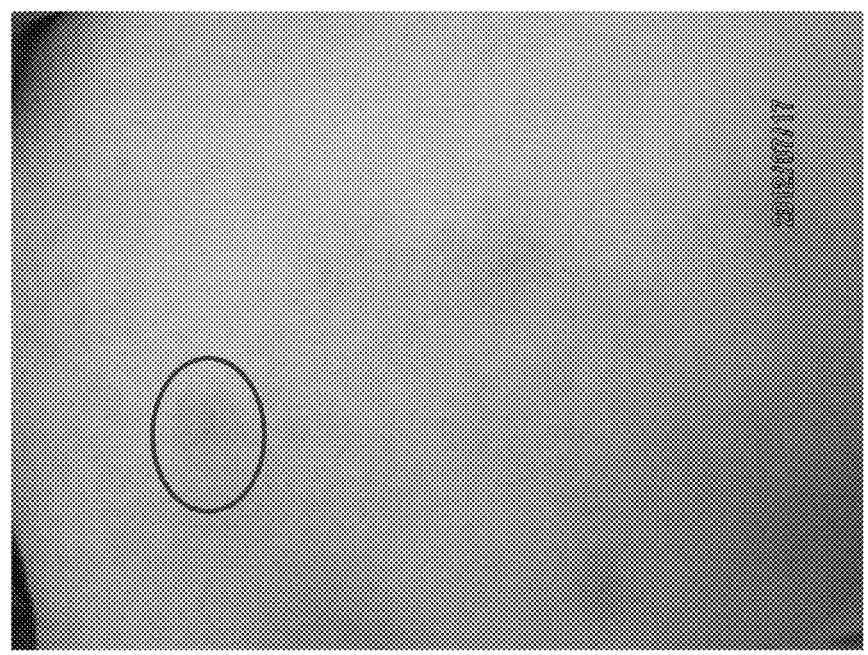
Figures 1B, 11:

CASE 4: An 8-month-old boy presented with multiple reddish nodules over back. Some has a pustule in the center (FIG. 11-1a). The QTT was positive and he cured completely after 5 days of antiviral agent. His mother whose HSIgG titer was 8.4 also complained of pustules over her hip (FIG. 11-1b). She first suffered from papular lesions on her trunk 2 months before delivery. Itchy scaly plaques on her baby's cheeks and around the ears were found 2 months after its birth. Both of them had been treated by antiviral agent 2 months later when they were first diagnosed as HSV-associated dermatitis. Because there were many BCs with large nuclei and thick cell membrane and some had intranuclear eosinophilic body in the QTT of the pustules over her hip (FIG. 11-1c), his mother was also treated with antiviral therapy. 7 days later, nearly all the pustules disappeared, yet there was still a new pustule on the left side of hip (FIG. 11-1b). Both of them do not have recurrence for one year till now CASE 5: An 8-years-old boy presented with many vesicles appeared over his swollen forearm suddenly 2 days ago (FIG. 11-2a). His two younger brothers also had past history of HSV-associated dermatitis. Balloon degeneration of the epithelial cells, band-like BC nest and large BCs with intranuclear eosinophilic body were observed in a QTT (FIG. 11-2b). Most of the vesicles became crusts and the swelling of his forearm improved a lot (FIG. 11-2c) 2 days after Valacyclovir granule. His brother who is 5 years younger than him suffered from multiple vesiculopapules over upper arm on the same time. He was also completely treated by antiviral agent for 5 days.

Figures 1A, 12:
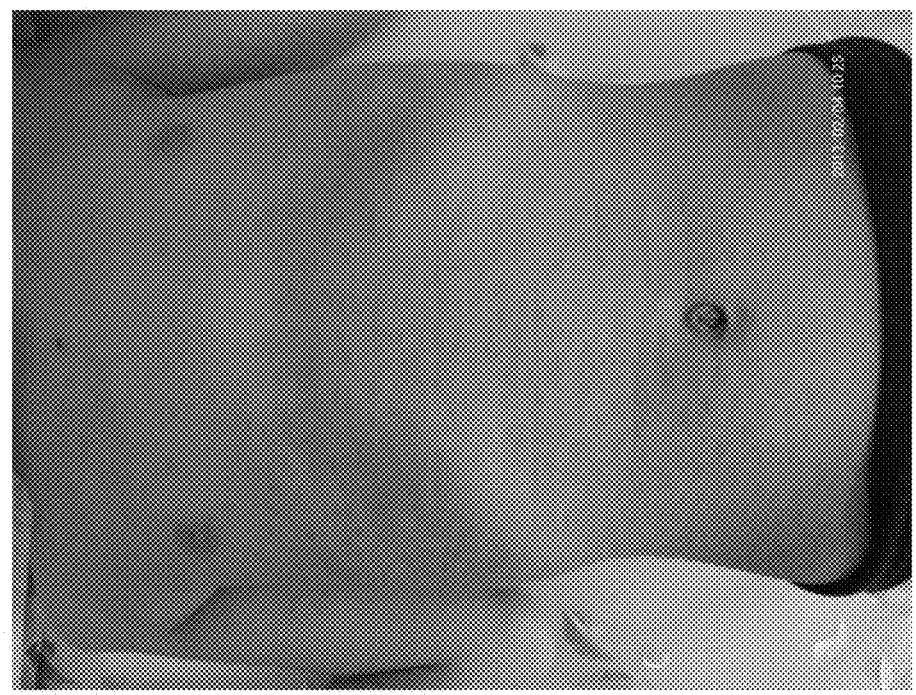
Figures 1B, 12:
Figures 2A, 12:
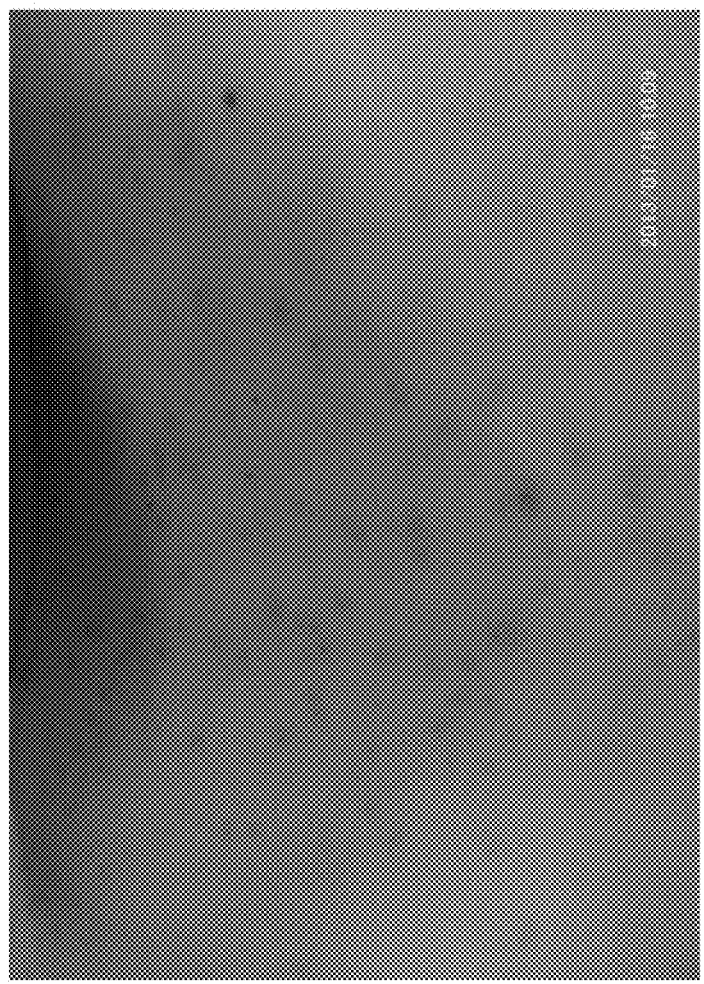
Figures 2B, 12:
Figures 2C, 12:
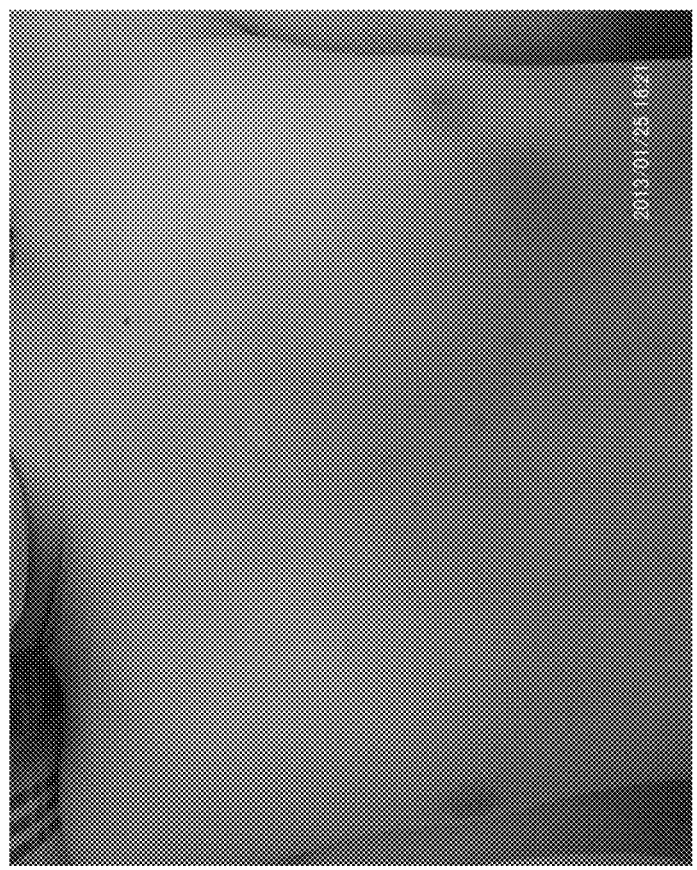

CASE 6: An 8-year-old boy presented with many small vesicopapules appearing suddenly and extending from his trunk to both thighs 3 days ago (FIG. 12-1a). Most of the vesicopapules gathered to became plaques. The boy complained with severe itching. This boy was treated with anti-allergic agents and TCS due to itchy scaly and papular eruptions first appeared on his face 2 months after his birth. Similar lesions appeared and recurred over his trunk till he was 2 years old. As the QTT was positive, the patient was treated with acyclovir. 2 days later there were nearly no vesiculopapules and plaques over his trunk and upper extremity (FIG. 12-1b). Her mother suffered from possible HSV-associated dermatitis in the $32^{th}$ week when she was pregnant for this boy. Antiviral agent was prescribed for the first time after a QTT taken from the pustules over her lower legs was positive when her son was 3 years old.

Figures 2C, 11:
Figures 2D, 12:
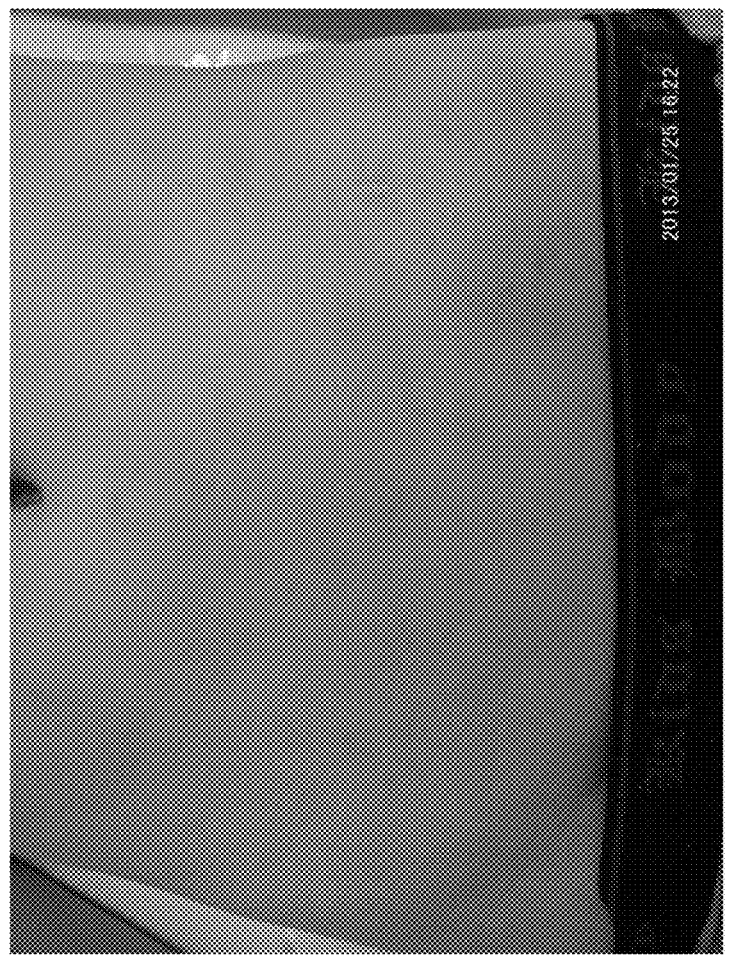

CASE 7: An 11-year-old boy presented with many papules and vesicopapules appeared suddenly over his neck and anterior chest yesterday (FIG. 12-2a). There were similar eruptions appeared over his scrotum and lower abdomen 3 days ago (FIG. 12-2b). Some of them turned into punched out erosions quickly. The boy complained of tingling pain. As the QTT from the vesicopapules on his chest was positive. Valacyclovir, anti-allergic agent and antibiotic ointment were prescribed. 9 days later, there were only few vesiculopapules over his anterior chest (FIG. 12-2c) and nearly no punched out erosions over his lower abdomen (FIG. 12-2d). The only abnormal data were that the HSIgG was 27.1 and IgE was 198 (normal: <170 IU/mL). Her mother was treated as atopic dermatitis for many years. After she was treated and followed by QTT in our clinic, normal skin increased instead of the hyperkeratotic skin with lichenification over her trunk and hands. The EIA titer of the HSIgG was 105, and the Ig E was 1393 IU/mL. She visited together with her son due to aggravations 2 months after her last visit.

Figures 1C, 11:
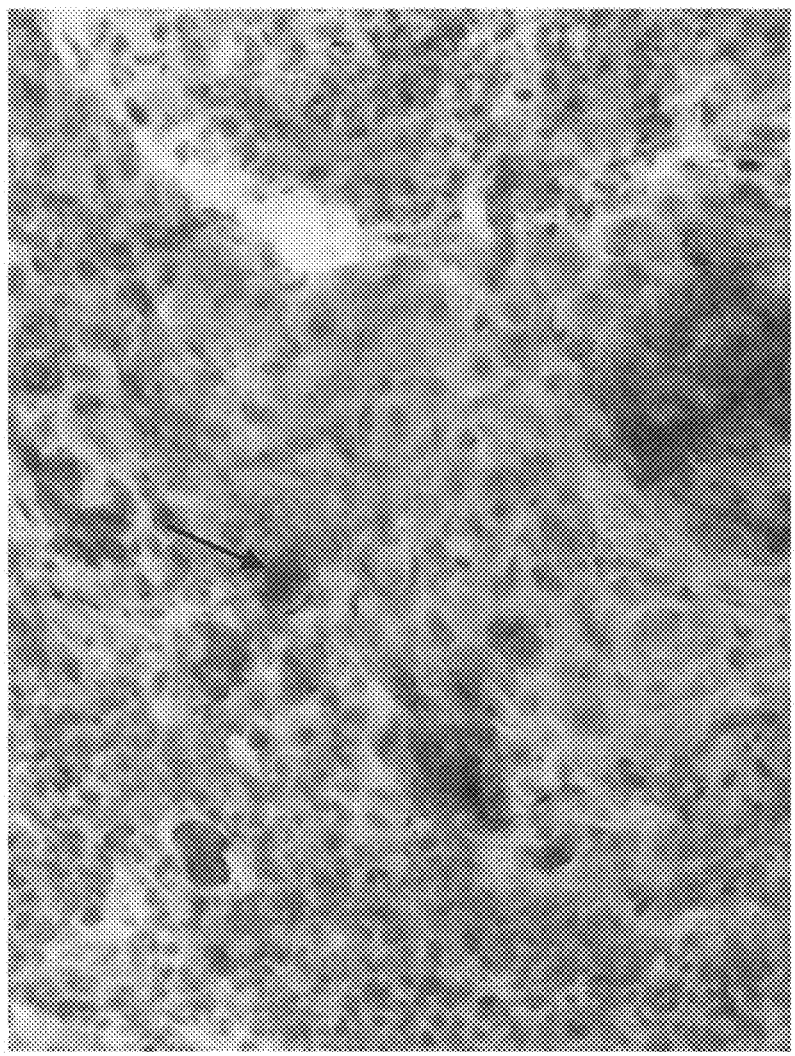
Figures 2A, 11:
Figures 2B, 11:
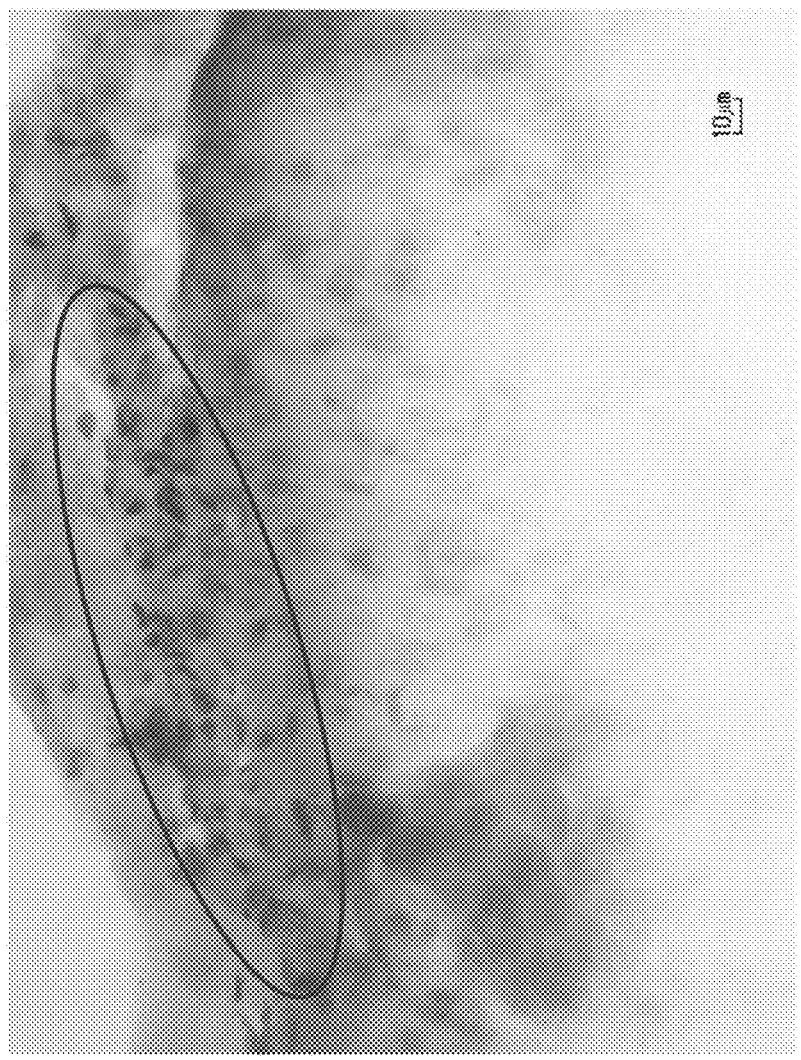
Figures 1A, 13:
Figures 1B, 13:
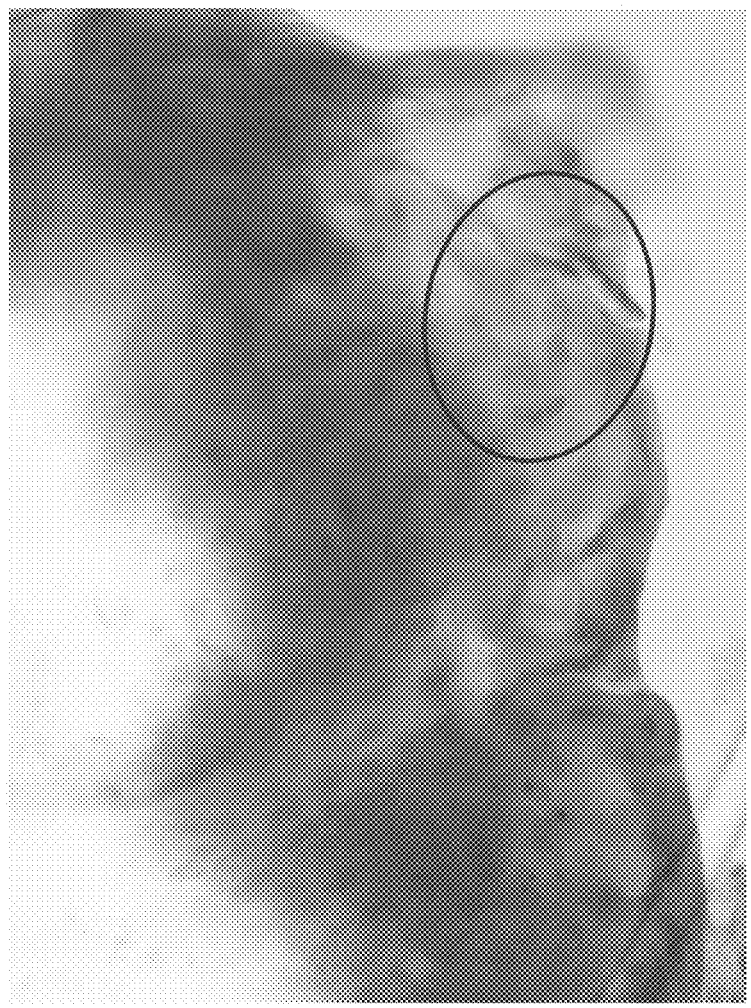
Figures 1C, 13:
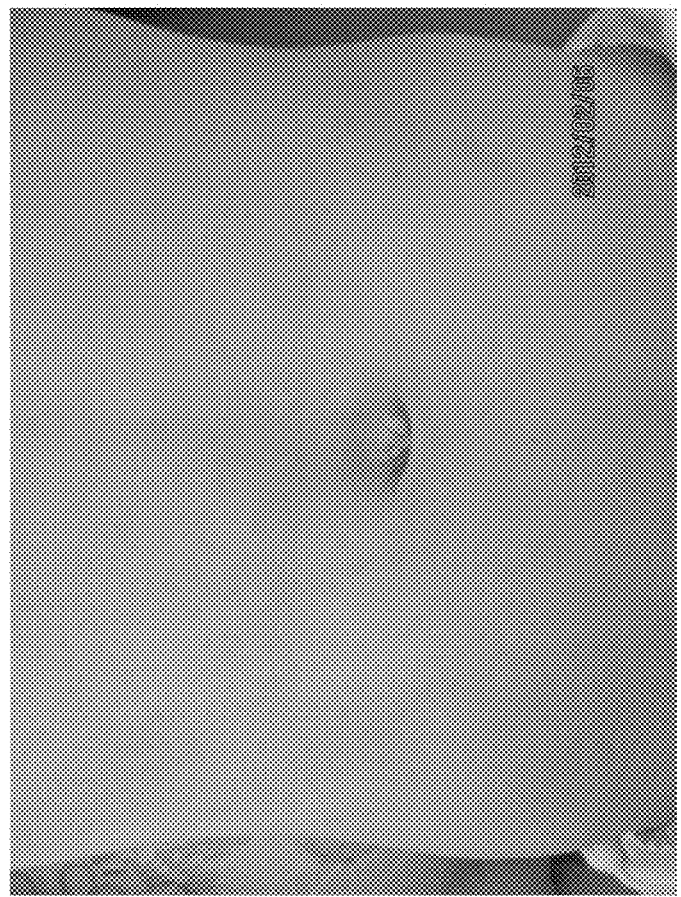
Figures 2A, 13:
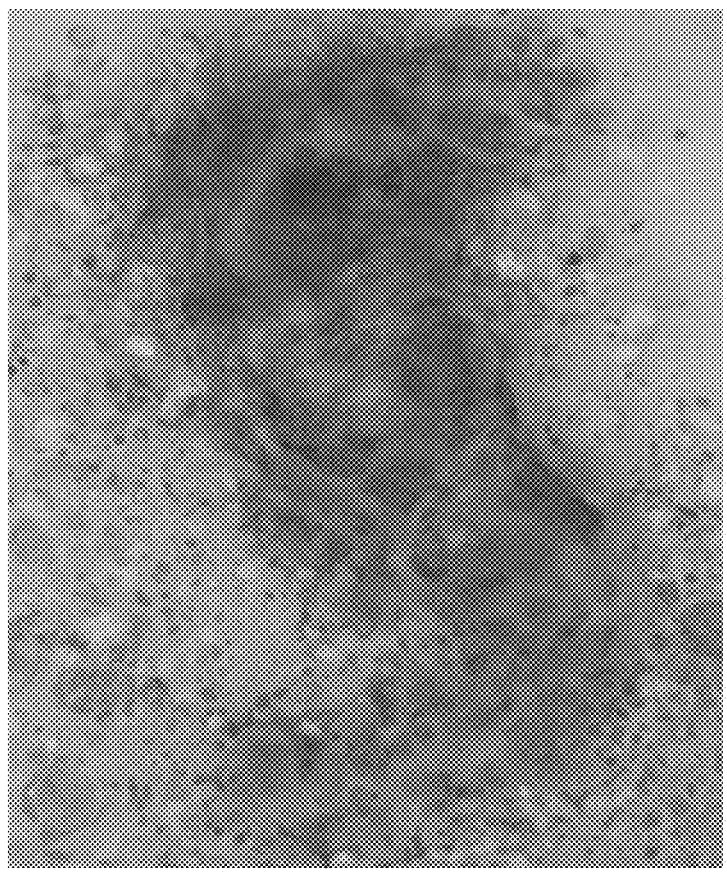
Figures 2B, 13:

Case 8: This 6-year-old girl presented with many itchy papules over her abdomen (FIG. 13-1a) and four extremities for a week. QTT from the papules over her abdomen revealed a group of BCs, BC nests and GCs were observed connected with the basement membrane (FIG. 13-1b). 5 days later, there were no more papules over her abdomen (FIG. 13-1c). She was treated as atopic dermatitis with TCS for 3 years before she visited our clinic 9 months ago. Completely disappearance of similar eruptions 7 and 9 months ago were also brought about by 5-7 days of acyclovir granules.

Case 9: A 21 years old female came for painful erosions and vesicles over her nape and along the left hair line for 3 days. She was treated with medium potency TCS under the diagnosis of atopic dermatitis about 3 times a year from 2 years old to 16 years old for itchy dry skin. The QTT from a vesicle revealed besides pleomorphic BCs, a giant cell with many nuclei moulding together were also observed (FIG. 13-2a). 3 days after treatment with Valacyclovir and anti-allergic agent, the roofs of the vesicles detached and became crusted erosions (FIG. 13-2b). Her skin lesion healed completely 7 days later. There was no recurrence for 2 years. Her mother, grandmother, younger brother and mother's sister were also suffered from HSV-associated dermatitis.

Case 1, 2, 3 all presented with multiple vesiculopapules and pustules beginning over their faces. The diagnosis was enabled by the QTT which clearly revealing the balloon degeneration in the spinous layer, intraepithelial vesicles as reported by Hsiao previously.[1,2,3] Besides the characteristic cytopathologic findings of BCs, GCs, the inflammatory infiltration by the eosinophils, polymorphnuclear leukocytes and lymphocytes were also clearly observed.

The Tzanck Test was introduced in 1947.[4] Compared with a polymerase chain reaction (PCR), the Tzanck test was confirmed to have a sensitivity of 76.9% and a specificity of 100% in a study of 98 patients (77 patients with recurrent herpes simplex and 21 patients with herpes zoster).[5] Its practical use and importance in diagnosing HSV infection, bullous diseases, and epidermal tumors have been recently reconfirmed.[6,7] Skin vesicles remain the easiest source of virus isolation and confirmation of diagnosis for the devastating HSV infection of newborn.[8] However, in contrast to the fetal disseminating neonatal HSV infection, it seemed skin biopsy was not indicative for the 3 healthy infants. This is the reason why similar patients are usually diagnosed as acne-like eruption of newborn, folliculitis, and seborrheic dermatitis thus treated as such. Even though case 2 experienced 2 episodes over her face and trunk, she presented only one pustule over her face on the 3rd episodes. The clinical picture furthermore proved that the antiviral agent was quite effective for her previous episodes.

The mother of case 4 whose HSIgG titer was 8.4 suffered from papular lesions on her trunk 2 months before delivery. He presented with erythema multiforme after experienced an itchy scaly plaques on his cheeks and around the ears 6 months ago. The QTT from the pustule in the infant's erythema multiforme and his mother's hip were both positive. They were treated by 5 days of antiviral agent, and there were no recurrence for one year till now.

CASE 5 presented with many vesicles appeared over his swollen forearm suddenly 2 days ago. His two younger brothers also had past history of HSV-associated dermatitis. The one who is 2 years old suffered from multiple vesiculopapules over upper arms for 2 months visited on the same day. Transmission of HSV can occur through intimate contact with infected parents, siblings and children care center.[9,10] Children being under 3 years old are susceptible to primary infection manifested as gingivostomatitis[11] and clinically apparent HSV infection.[12] Besides these reports documenting typical HSV infection, atypical HSV presented with various clinical entities as cases in this study is not yet reported. Consequently, QTT should be applied to diagnose more atypical HSV-associated dermatitis for early treatment.

Case 6 whose mother suffered from an unrecognized HSV-associated dermatitis from the $32^{th}$ week of pregnancy for this boy. He had never been treated with antiviral agents for the scaly eczematous lesions recurred over his trunk from 2 months to 2 years old.

Case 7 was born to a woman who was treated as atopic dermatitis before his birth. Before the extensive, multiple Kaposi's varicelliform eruption, he was treated twice by antiviral agents with complete recovery. Recrudescence may be in different and distant locations because asymptomatic viremia occur in primary[13,14] and recurrent herpes infections[13,15,16] in immunocompotent hosts. Detection of HSV in non-herpetic areas of patients with eczema herpeticum suggests that they may also be directly and indirectly spread via the hands and underwear.[17] Detecting HSV-DNA within the epidermis using PCR in vivo,[18] in cultured keratinocytes,[19] and in non-herpetic areas of patients with eczema herpeticum[17] supports the notion that subclinical HSV infection may spread during every recurrence. Case 6 may experience a gradually subclinical spreading of the untreated HSV-associated dermatitis during past 6 years free of clinical symptom. The acute onset of the eruption, quick and complete response to the antiviral therapy proves the effectiveness of the antiviral therapy. In addition, it demonstrates that both eczema herpeticum (case 6) and Kaposi's varicelliform eruption (case 7) were elicited by HSV recurrence that resides within the dermis[20] and epidermis.[18, 19]

Keratosis pilaris (KP) is an extremely common condition that manifests as small, rough folliculocentric keratotic papules. KP is included as an associated features of the Hanifin and Rajka diagnostic criteria for the atopic dermatitis.[21]

Case 8, a 6-year-old girl presented with KP over her abdomen and four extremities which responded well to antiviral agent without recurrence for more than 1 year.

On the other hand, Case 9 was treated about 3 times a year until 5 years ago with medium potency TCS under the diagnosis of atopic dermatitis because there was KP from her neck to trunk. The observation of the pleomorphic BCs and a giant cell with tremendous nuclei moulding together imply that TCS only actually suppressed the immune reaction toward the HSV-infected cells but were unable to lessen them. The undetected HSV-infected cells remained and even increased and enlarged in every episodes. The not fully treated HSV-infected cells may induce increasement of serum HSIgG Ab and IgE that reported by Hsiao in a study of 787 patients suffering from HSV-associated dermatitis.[1] There are many studies concerning the relationship between HSV infection and atopic dermatitis recently[22, 23, 24] A large cohort study of 235 adults revealed that patients treated as atopic dermatitis with history of eczema herpeticum had earlier age of onset, significantly high serum IgE, higher frequency of concomitant physician diagnosed asthma and allergic rhinitis.[25] If these patients are diagnosed and followed by QTT as the patients reported in this study, early and adequate treatment may improve the prognosis not only for dermatitis but also for their concomitant asthma and allergic rhinitis.

Among the infants whose age of onset was before one year old, one was presented as erythema on hip and one as typical HS around lip, others all presented as multiple atypical HSV-associated dermatitis beginning over face. The most possibly origin of the HSV infection was from the hematogenous spread through the placenta and to the fetus. This route is the consequence of viremia accompanying HSV of its mother during her pregnancy.[26, 9, 13] In a study of 56 newborns with neonatal HSV infection, the tranplacental maternal HSV Ab failed to influence the outcome of the devastating infection.[8] In this study, the transplacental maternal HSV Ab induced a Ab dependent CMI to the HSV-infected cells was confirmed by the QTT. QTT provided a cytologic evidence for other studies that HSV Ab protect the mother and newborns from severe infection.[27, 28, 9] The beginning of HSV-associated dermatitis over face is consistent with the cranial-caudal maturation of the Langerhans cells capable of antigen presenting in rat which is directed by the maturation of nervous system.[29] There were reports about the HSV infection developed in neonates,[30] and children as encephalitis,[31] acute retina necrosis[32] reported to be due to the reactivation of a previously and undiagnosed asymptomatic neonatal HSV infection. In contrast to these infection which may result in considerable disability, our patients represented the most easily diagnosed mucocutaneous manifestations of the consequences of vertical HSV transmission during gestation. However, if misdiagnosed like most of the HSV-associated dermatitis as etiology unknown eczema the prescribed TCS may prompt the retrograde transport of the HSV-infected cell. Besides trigeminal ganglia, superficial cervical and vagus ganglia to brain tissue the most effective route was proved to be through the olfactory pathway to invade central nervous system.[33] HSV infection of the CNS even it take place silently, may bring about learning and behavioral deficiency.[34]

Besides maternal transmission, recurrence of the children persisted and subsided until their father (family 2 and 3) started the antiviral therap. Concomitant (case 5) and consecutive (case 8) occurrences of siblings by HSV were also observed in this study. Viruses, most plausibly HSV was hypothesised by Hussain in 2003 to cause the transmissible atopic disease based on many epidemiologic evidences.[35] QTT may be the most handy cytologic diagnostic tool to prove Hussain's hypothesis. In other words, the self-perpetuating active production of high-level of specific IgE[36, 37] is due to latency of the HSV. The population possessing the immunity toward HSV could be estimated by the high seroprevalent which was reported to be up to 90% at the forth decade.[13] Newborns from a seropositive mother were protected by the transplacental HSV Ab from HSV infection. Hence, the HSV-infected cells were usually presented together with inflammatory infiltration to hinder the proper diagnosis. The patients who are suffering from and capable of transmitting HSV-associated dermatitis are nearly universal. —The effective prevention of HSV-associated dermatitis and atopic diseases could and should be started from seropositive pregnant women and family members. QTT could be applied as the most quick and non-invasive cytologic diagnostic tool to disclose this common yet concealed infectious disease. Early diagnosis and treatment by dermatologist of this neurotropic pathogen is warrants because it always possesses the potentiality of retrograde transport to central nervous system.

1st Clinical Case of Acne

Figure 14:
FIG. 14 is a picture showing 1st clinical case of acne before treatment.

Before the treatment: FIG. 14 is a patient presented with many painful pustules over her face especially around her mandible for 3 months. The pus was proved to be positive for HSV by polymerase chain reaction (PCR).

Figure 15:
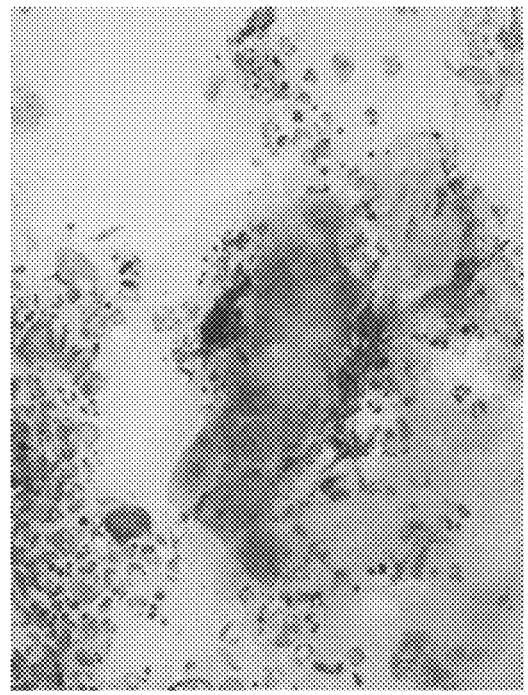
FIG. 15 is a photomicrograph of cells of $1^{st}$ clinical case of acne.
Figure 15:

FIG. 15 is an image of QTT sample which from the same pustule revealing that a dermal nerve fiber (DNF) is surrounded by many balloon cells (BCs). There were other similar degenerated Schwann cells groups. High magnification demonstrated many BCs with large and pleomorphic nuclei. The pathologic findings together with the result of the PCR confirmed that these pustules originated from HSV infection.

Figure 16:
FIG. 16 is a picture showing $1^{st}$ clinical case of acne after treatment.

Diagnosis: acne induced by HSV infection
Prescriptions:
Valacyclovir: 2 tablets daily for 5 days
Nadifloxacin cream for 5 days
After the treatment: FIG. 16 is an affected part of the patient after the treatment. The number of the pustules and the extent of inflammation decreased 5 days later.

2nd Clinical Case of Acne

Figure 17:
FIG. 17 is a picture showing $2^{nd}$ clinical case of acne before treatment.

Before the treatment: FIG. 17 is a patient presented with many reddish-brown pustules and pigmented spots over her face for one month.

The QTT sample from a pustule revealed long, degenerated DNFs were surrounded by many BCs. The patient was diagnosed as acne-like eruption originated from HSV infection.

Figure 18:
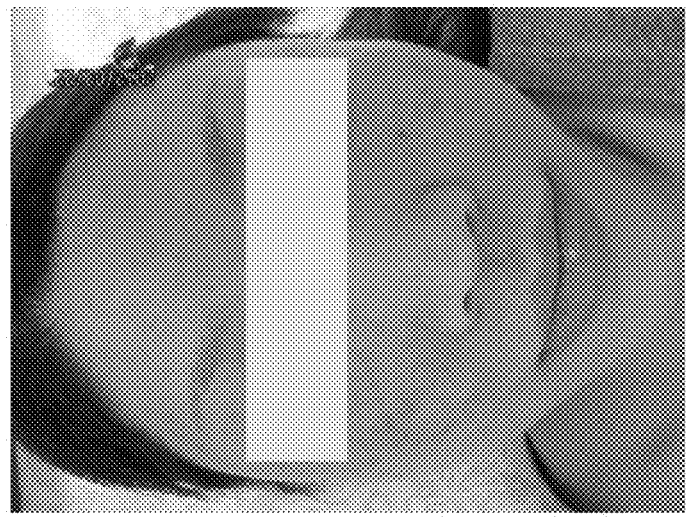
FIG. 18 is a picture showing $2^{nd}$ clinical case of acne after treatment.

Diagnosis: acne induced by HSV infection
Prescriptions:
Valacyclovir: 2 tablets daily for 5 days
Acyclolidofenac (ADO) ointment After the treatment: FIG. 18 is an affected part of the patient after the treatment. Nearly no pustules were seen 8 days later. Her skin became finer and whiter.

3$^{rd}$ Clinical Case of Acne

Figure 19:
FIG. 19 is a picture showing $3^{rd}$ clinical case of acne before treatment.
Figure 19:

Before the treatment: FIG. 19 is a patient presented with many comedoes, pustules combined with severe inflammation over his nose for 5 months.

The QTT sample from a pustule revealed long, degenerated DNFs were surrounded by many BCs. Giant cells (GCs) and melanin pigments are also found.

HSV IgG enzyme immunoassay titer (normal <2.0): 53.1

Diagnosis: acne induced by HSV infection

Prescriptions:

Antiviral agent: Valacyclovir 2 tablets daily for 5 days per month.

ADO ointment

Figure 20:
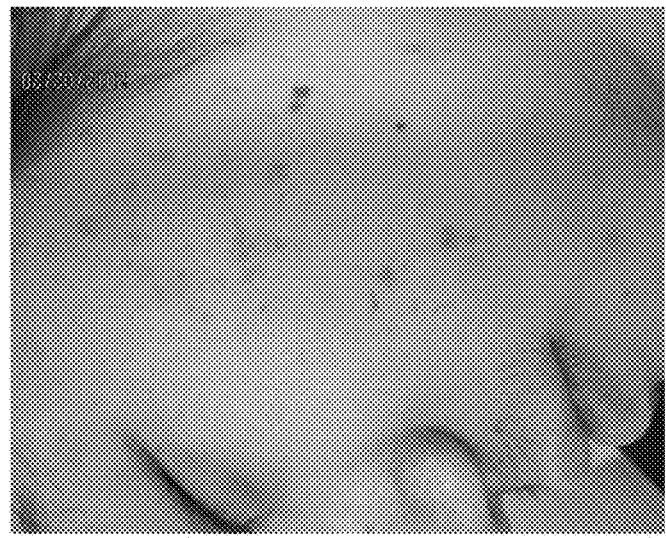
FIG. 20 is a picture showing $3^{rd}$ clinical case of acne after treatment.
Figure 20:
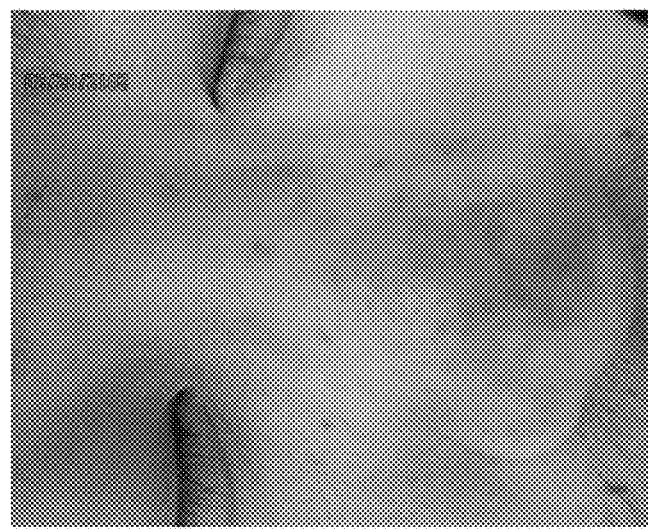

After the treatment: FIG. 20 is an affected part of the patient after the treatment. The severe inflammation on the nose and over the left cheek decreased a lot. The number of the white comedoes also decreased 23 days later.

4$^{th}$ Clinical Case of Acne

Figure 21:
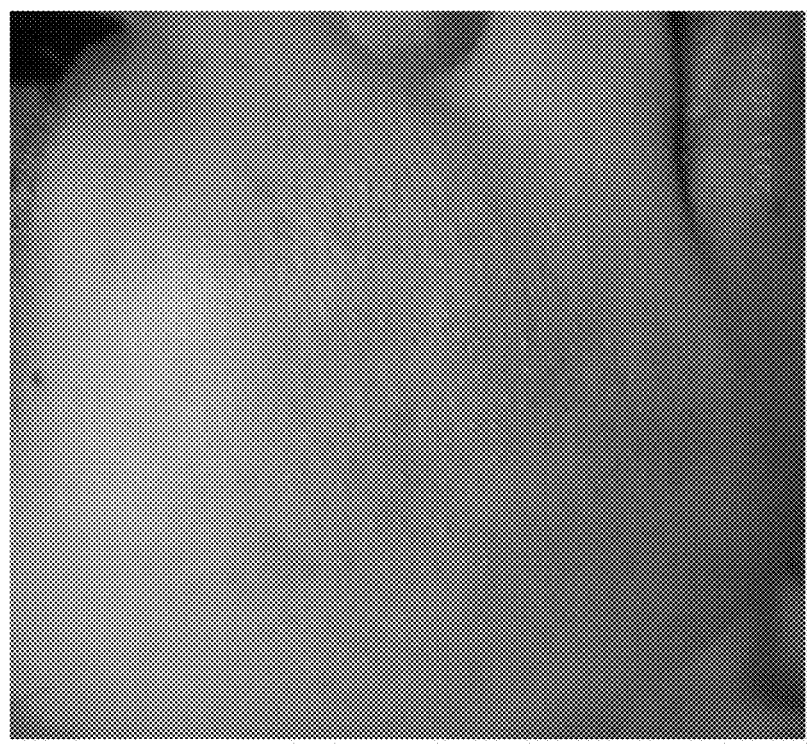
FIG. 21 is a picture showing $4^{th}$ clinical case of acne before treatment.

Before the treatment: FIG. 21 is a patient presented with many itchy pin-head-size pustules appearing suddenly over her face. The eruption appeared suddenly after she applied new kind of skin lotion over her face.

Figure 22B:
FIG. 22$a$-FIG. 22$b$ are photomicrographs of cells of $4^{th}$ clinical case of acne.
Figure 22A:
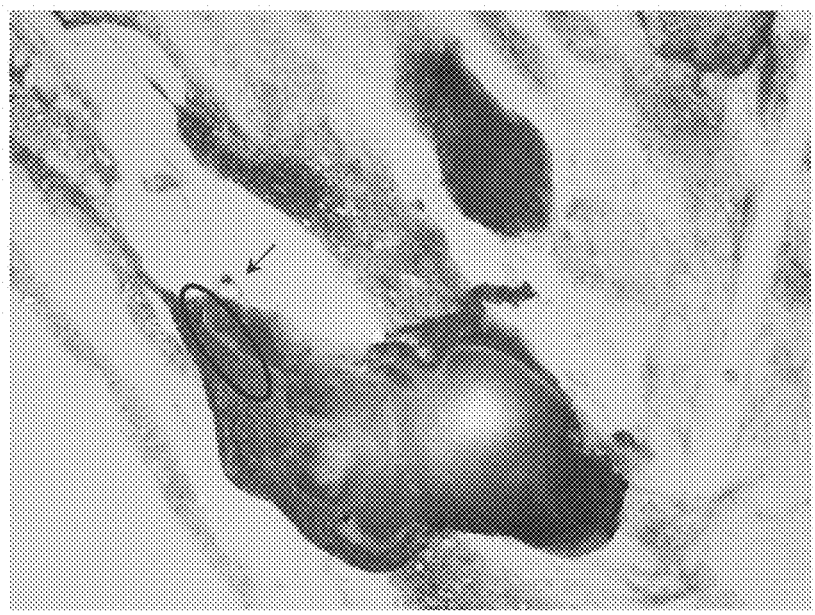

FIG. 22*a* is an image of QTT sample revealing a degenerated nerve (circle) and hair (arrow) are observed in an enlarged hair follicle due to dense inflammatory infiltration.

FIG. 22*b* is an image of QTT sample revealed a BC with thick cell membrane and intranuclear eosinophilic inclusion body (EIB). Some BCs gathered together to form balloon cell nests (BCNs).

Diagnosis: acne (multiple pustular type) induced by HSV infection

Prescriptions:

Valacyclovir: 2 tablets daily for 5 days

Anti-allergic agent for 7 days

Gr. IV topical corticosteroids (CS)

Figure 23:
FIG. 23 is a picture showing $4^{th}$ clinical case of acne after treatment.

After the treatment: FIG. 23 is an affected part of the patient after the treatment. Not only the number but also the size of the pustules decreased a lot 2 days later. After completed the prescribed medication, there is no recurrence till now (about one year).

5$^{th}$ Clinical Case of Acne

Figure 24:
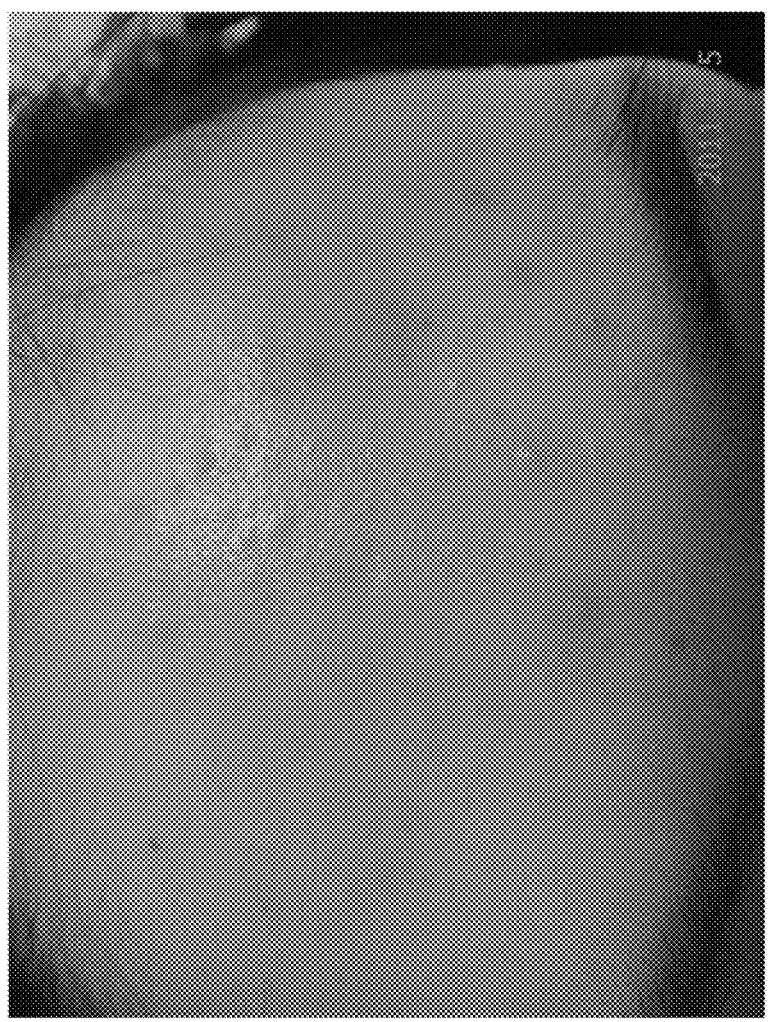
FIG. 24 is a picture showing $5^{th}$ clinical case of acne before treatment.

Before the treatment: FIG. 24 is a patient presented with many small red vesicopapules and pustules over her forehead, both cheeks for 2 weeks.

Figure 25B:
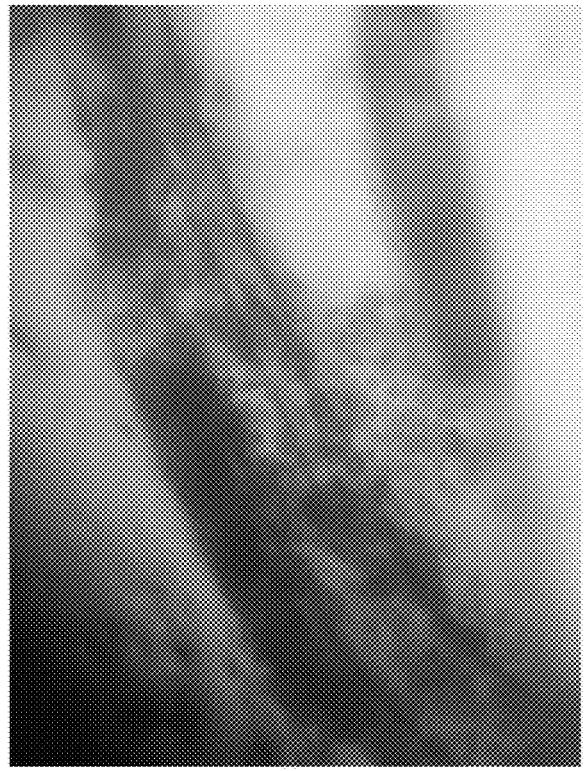
FIG. 25$a$-FIG. 25$b$ are photomicrographs of cells of $5^{th}$ clinical case of acne.
Figure 25A:
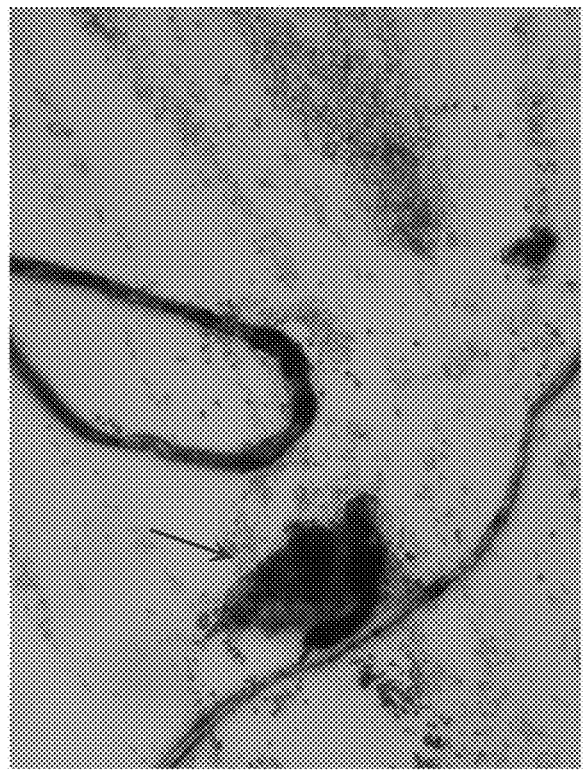

FIG. 25*a* is an image of QTT sample revealing that a large BC nest (arrow) was observed surrounded one of the 2 demyelinated DNFs.

FIG. 25*b* is an image of QTT sample revealed BCs of various sizes surrounded 2 demyelinated DNFs.

Diagnosis: acne induced by HSV infection

Prescriptions:

Valacyclovir: 2 tablets daily for 5 days

Antibiotics 2 days

Nadifloxacin cream

Figure 26:
FIG. 26 is a picture showing $5^{th}$ clinical case of acne after treatment.

After the treatment: FIG. 26 is an affected part of the patient after the treatment. Symptoms have significantly improved 7 days later.

6$^{th}$ Clinical Case of Acne

Figure 27:
FIG. 27 is a picture showing $6^{th}$ clinical case of acne before treatment.

Before the treatment: FIG. 27 is a patient presented with many red inflamed nodules over her face for 1 week. She also complained of pain over her cheeks and itching over her mandible.

Figure 28B:
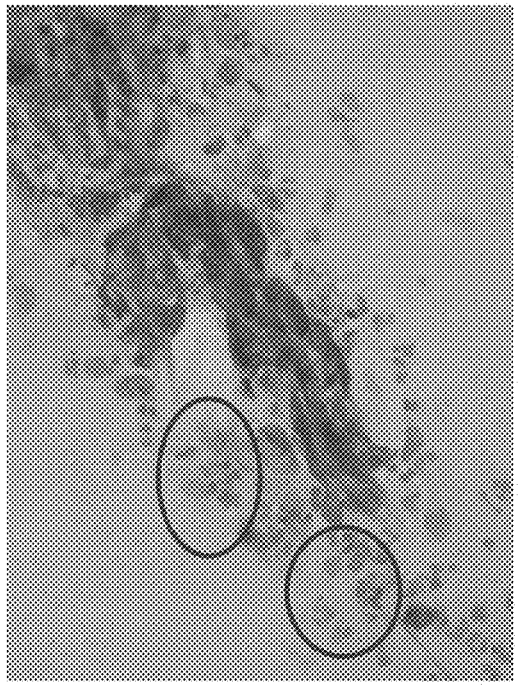
FIG. 28$a$-FIG. 28$b$ are photomicrographs of $6^{th}$ clinical case of acne.
Figure 28A:
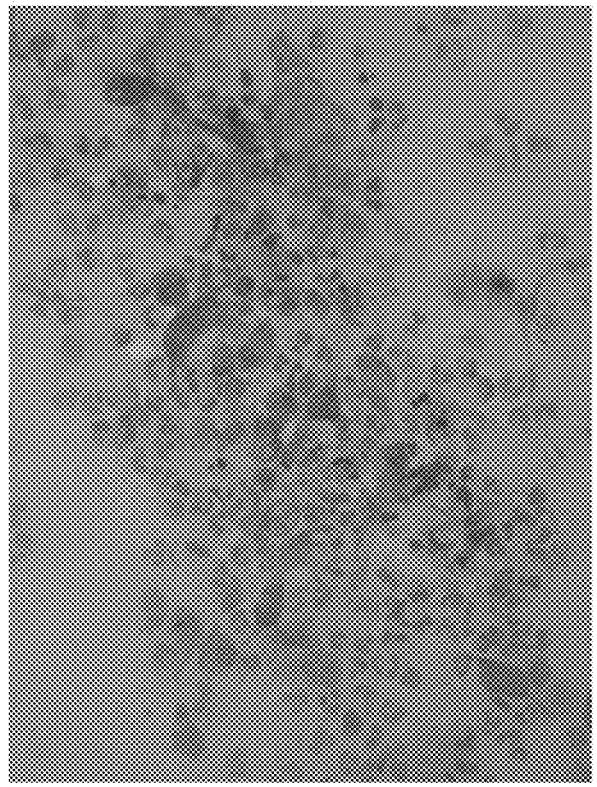

FIG. 28*a* is an image of QTT sample revealed BCs with EIBs and scattering BCNs.

FIG. 28*b* is an image of QTT sample revealed many longitudinal, large BCs and inflammatory infiltration by neutrophils (circles).

Diagnosis: acne induced by HSV infection

Prescriptions:

Valacyclovir: 2 tablets daily for 5 days

Nadifloxacin cream

Gr. IV topical CS

Figure 29:
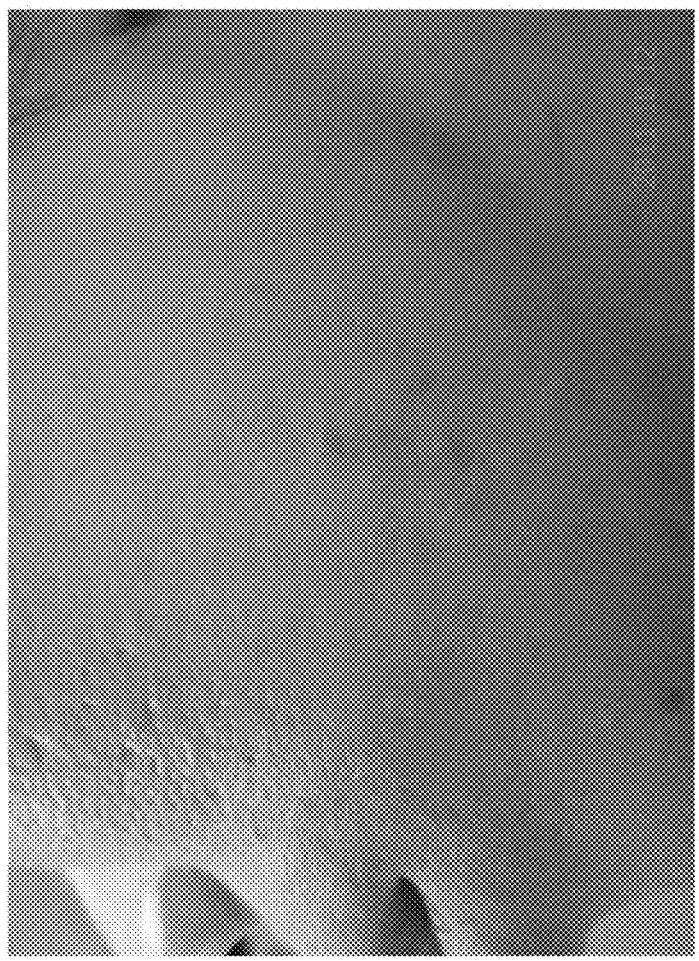
FIG. 29 is a picture showing $6^{th}$ clinical case of acne after treatment.

After the treatment: FIG. 29 is an affected part of the patient after the treatment. Symptoms have significantly improved 7 days later.

Above 6 patients presented with clinical picture of acne that have long been thought to be due to bacterial infection. However, the pathologic findings together with the result of the PCR confirmed that these pustules and red papules are caused by HSV infection.

3 days after intraperitoneal inoculation of HSV in Albino mice, general weakness and/or marked paralysis of the hind limbs developed (Yamamoto et al., *Acta neuropath (Berl.)* 26, 285-299 (1973)). Yamamoto et al. confirmed that neurons, astrocytes, oligodendrocytes and Schwann cells were infected. The endothelial cell, perineural fibrocyte and smooth muscle cells could also be infected. Affection of the hemispheres and cerebellum was limited, while pontobulbar, spinal lesions were severe and extensive. The site of virus replication in the peripheral nervous system was primarily in neurons, but replication occurred with great frequency in Schwann cells. This study documented that HSV is a systemic infection. The Schwann cells were infected and served as a mediating role in the spread of the HSV along peripheral nerve fibers to the central nervous system. The inflammatory infiltration surrounding the degenerated DNFs and ballooning Schwann cells in the QTT of patients suffering from acne may represent the immune reaction to excrete the HSV-infected cells through skin in order to protect central nervous system. Since the skin is the most external part of the nervous system, acne may represent the excretion of the HSV-infected cells after the maturation of one's immune system during adolescence.

The innervations of the hair follicle are the most complex and thus thoroughly studied among the cutaneous sensory receptors. It is because the innervations of the hair follicles arising from the myelinated stem axons in the deep dermal plexus together with the Pacinian corpuscles are the deepest sensory receptors. Pacinian corpuscles are the largest sensory corpuscles found not only in the palmar and plantar aponeurosis or genitalian deep to the skin and also present in ligaments and joint capsules (Munger et al., *Arch Histol Cytol.* 51, No 1, 1-34 (1988)).

Arthritis can thus be elicited by the HSV infection of the Pacinian corpuscles in ligaments and joint capsules as the acne-like eruption does in the skin. Actually the acne in adolescence could be self-limited but its fulminate type may combine fever and multiple joint pains (Medscape, *Acne Fulminate* Mar. 29, (2011)). Increase level of substance P has been documented in the synovial fluid and serum of patients with rheumatoid arthritis (Marshall et al., *Arthiritis Pherma* 33 (1): 87-90 (1990); Menkes et al, *J Rheumatol* 20 (4): 714-17 (1993)). Substance P stimulates prostaglandin E2, and collagenase release from the rheumatoid synoviocytes. These findings were reported to be responsible for the pannus formation in rheumatoid patients (Lotz et al., *Science* 235; 893-895 (1987)). After the disclosure of the pathologic changes causing acne in the Schwann cells of the DNFs, it is worthwhile to examine the pathologic changes in the diseased joints by QTT in this invention. There is a great chance to find a primary lesion in the sensory receptors and peripheral nerve fibers in the joints.

Substance P and other neuropeptides can be released from the peripheral sensory nerve fibers in the skin, muscle and joint in response to certain types of infection or injury and induce a local inflammatory (Donkin J J et al., *Progress in brain research*, 161:97-109 (2007)). In other words, the ballooning Schwann cells, desheathing DNFs induce by HSV infection followed by an inflammatory reaction mediated by neurogenic peptides in order to decrease the HSV-infected cells. However, if the HSV infected cells are too less to induce vesicles or pustules, the severe inflammatory reaction may lead a clinical mis-diagnosis of etiology unknown dermatitis, acne and arthritis. The QTT is the quickest method to diagnose the underlying HSV infection in various organs and is able to bring about an early treatment by the antiviral agents.

The tumor necrosis factor-alpha inhibitors are the most potent treatment for the rheumatoid arthritis around 2000. However, there are many reports concerning the adverse cutaneous reaction secondary to treatment for rheumatiod arthritis with tumor necrosis factors—alpha inhibitors after 2000. Two patients with erythema multiforme (Soliotis F et al., *Ann Rheum Dis* 61: 850-1, 2002; Vergara G et al, *Arch Dermatol* 138: 1258-9, 2002), one with atopic dermatitis-like eruption (Wright R C, *J Am Acad Dermatol*, 49:160-1, 2003) and another with perforating folliculitis (Gilaberte Y et al., *British J of Dermatol*, 156:368-71, 2007) were reported. Two review studies (Leigh I M et al., *Vlini Exp Dermatol*, 10: 58-67, 1985; Schofield J K et al, *Br J Dermatol*, 128: 542-5,1993) found that about 70% of recurrent erythema multi-forme were precipitated by HSV. A double-blind trial in 1995 (Tatnall F M, *British J of Dermatology*, 132:267-70 (1995)) shown that recurrent erythema multiforme can be completely suppressed by continuous acyclovir therapy. In this invention atopic dermatitis-like eruption was proved to be precipitated by HSV infection. These are further indirect evidences that HSV can cause systemic infection and manifests as dermatitis, erythema multiforme, acne and arthritis.

Consequently, the treatment in the present invention of acne may comprise a cream or an ointment mixed by an Anti-HSV agent to put on the affected part of the patient, wherein the Anti-HSV agent comprises Valacyclovir or Acyclovir. For example, the ADO ointment used in this invention contains acyclovir, lidocaine and diclofenac.

1$^{st}$ Clinical Case of Impetigo

Figure 30B:
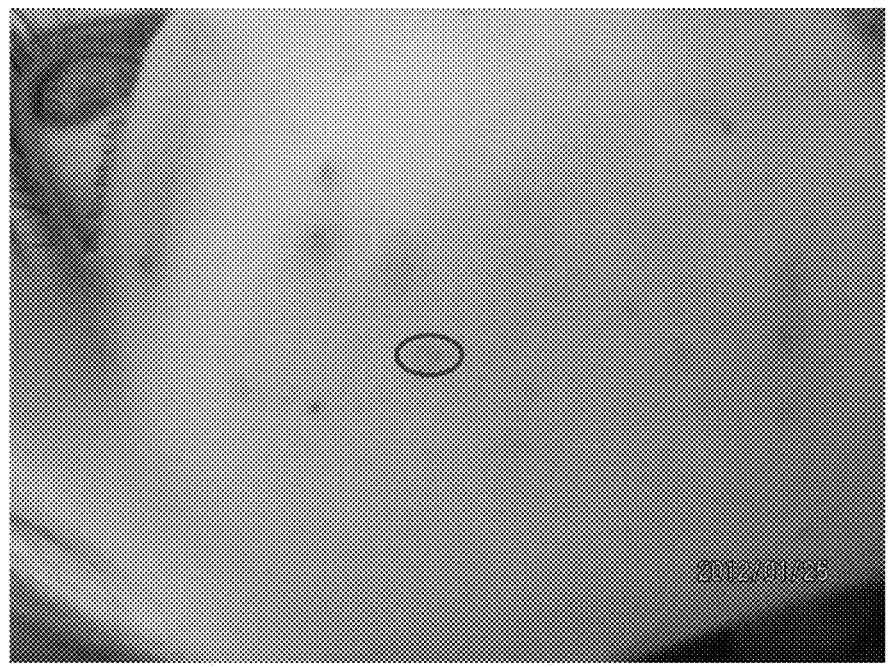
FIG. 30$a$-FIG. 30$b$ are pictures showing $1^{st}$ clinical case of impetigo before treatment.
Figure 30A:

Before the treatment: FIG. 30a is a patient presented with increasing crusted vesicles appearing around her mouth for 1 week. Some vesicopapules were also found over her right cheek about 2 days ago.

Figure 31A:
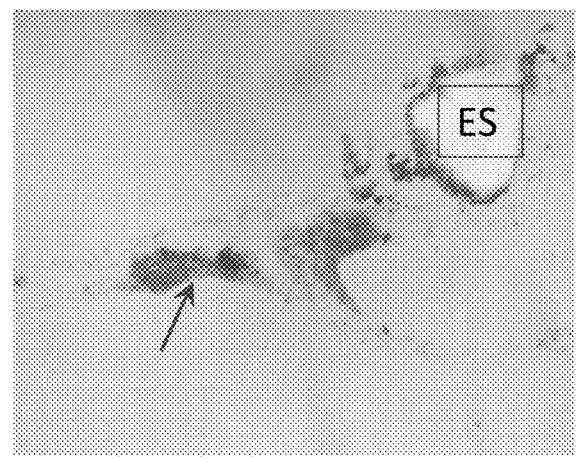
FIG. 31$a$-FIG. 31$c$ are photomicrographs of cells of $1^{st}$ clinical case of impetigo.

Before the treatment: FIG. 30b Some vesicopapules were also found over her right cheek. A vesicle (circle) was removed for QTT FIG. 31a is a first image of QTT sample: The QTT taken from the vesicle over the cheek included an epidermal sheet (ES) and band-like dermal compartment. The DNFs (arrow) was surrounded by an inflammatory infiltration.

Figure 31B:
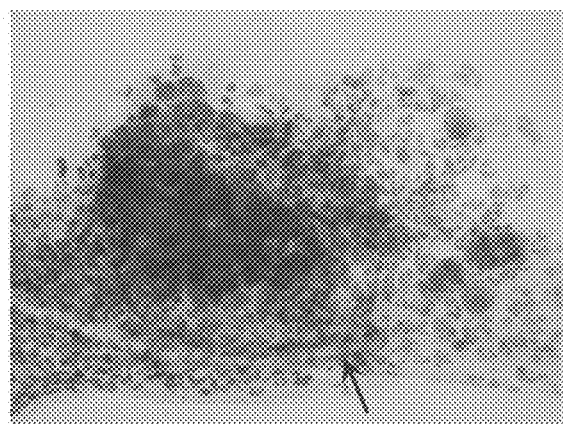

FIG. 31b is a second image of QTT sample: Balloon degeneration of the Schwann cells around a degenerated DNF (arrow). Some BCs gathered to become BC nests. EIBs were observed in some BCs.

Figure 31C:
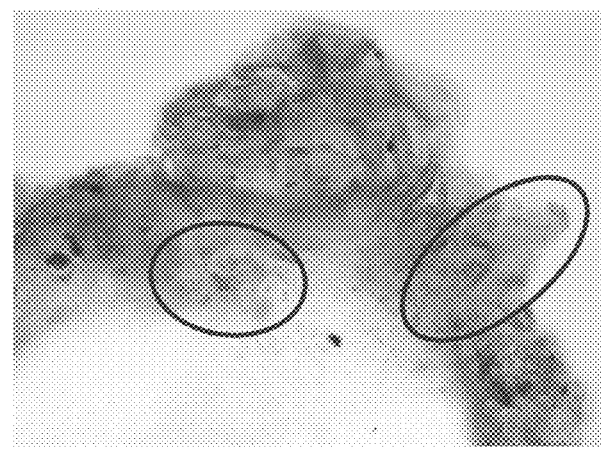

FIG. 31c is a third image of QTT sample: Micrococi (circles) was observed overlaid the BCs.

Figure 32:
FIG. 32 is a picture showing $1^{st}$ clinical case of impetigo after treatment.

Diagnosis: impetigo induced by HSV infection
Prescriptions:
Acyclovir G. 10 mg/kg 4 times a day for 7 days (1$^{st}$ visit)
Oral antibiotics for 4 days (2$^{nd}$ visit)
Anti-allergic agents for 8 days
Antibiotics ointment After the treatment: FIG. 32 is an affected part of the patient after the treatment. After Acyclovir for 7 days, there were only some erythema on her mandible and some small red erosions over right cheek 9 days later. As micrococi were observed in the QTT, cefcapene pivoxil hydrochloride for 4 days was prescribed.

2$^{nd}$ Clinical Case of Impetigo

Figure 33:
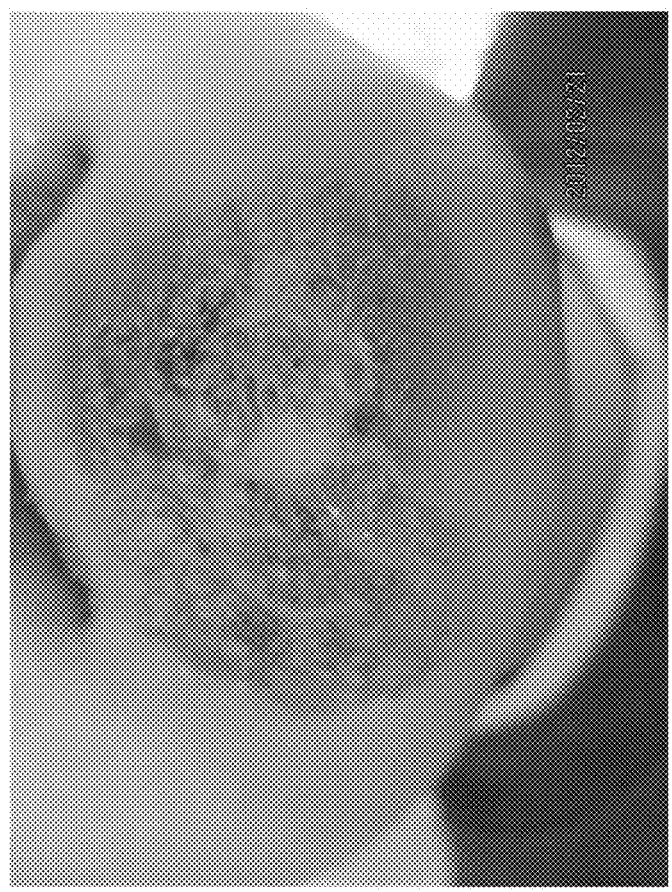
FIG. 33 is a picture showing $2^{nd}$ clinical case of impetigo before treatment.

Before the treatment: FIG. 33 is a patient presented with many vesicopapules appearing over her mandible since 10 days ago. The vesicopapules dried and merged into a plaque with many yellowish crusts and surrounded by vesicopapules.

Figure 34B:
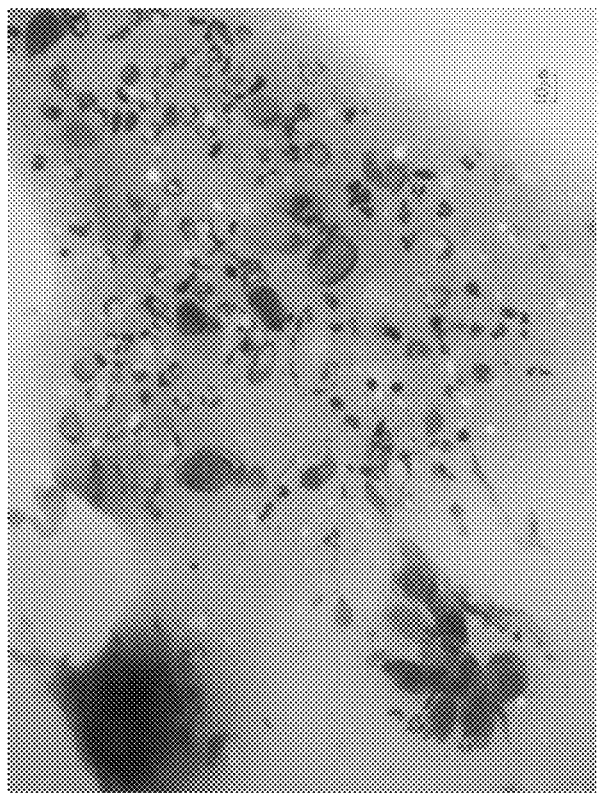
FIG. 34$a$-FIG. 34$b$ are photomicrographs of cells of $2^{nd}$ clinical case of impetigo.
Figure 34A:
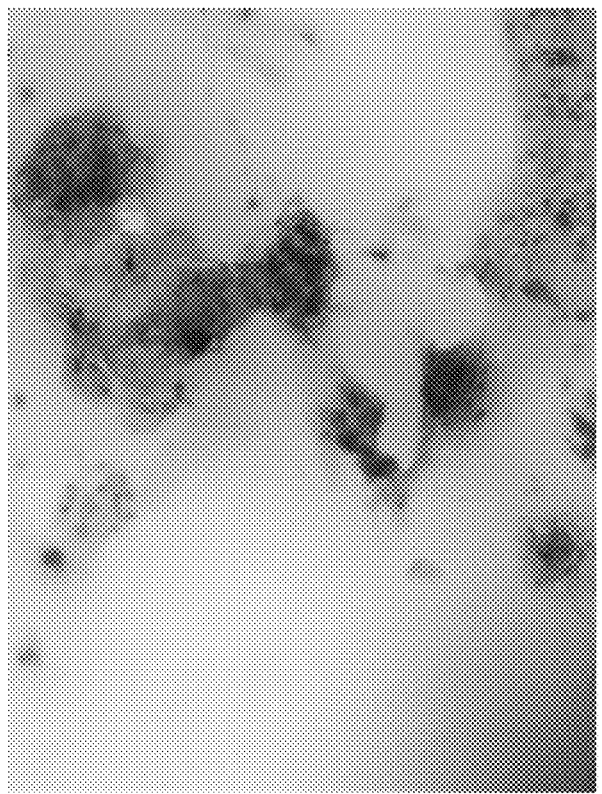

FIG. 34a is a first image of QTT sample: The QTT taken from the mandible revealed degenerated nerves surrounded by ballooning Schwann cells.

FIG. 34b is a second image of QTT sample: Many BCs and balloon cell nests (BCNs) with high N/C ratio were observed in the dermis.

Figure 35:
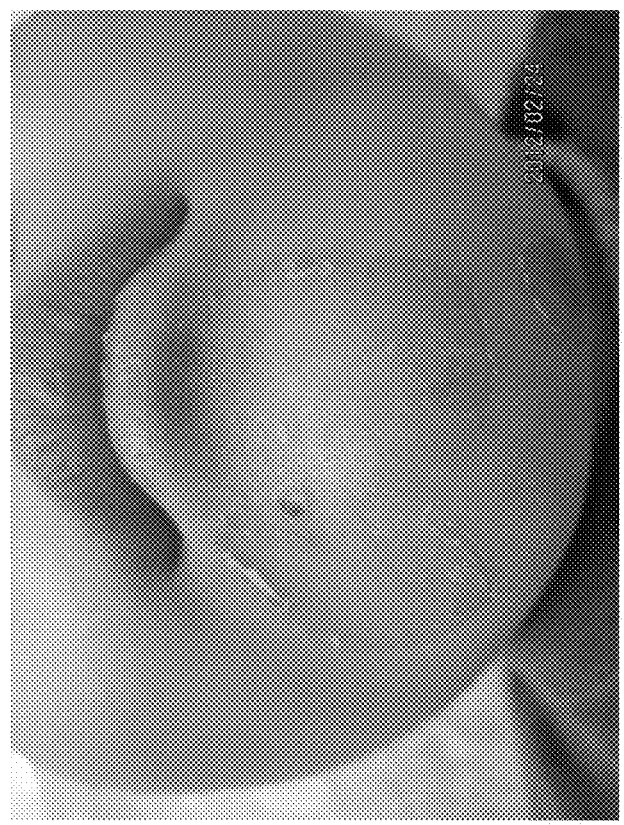
FIG. 35 is a picture showing $2^{nd}$ clinical case of impetigo after treatment.

Diagnosis: impetigo induced by HSV infection
Prescriptions:
Acyclovir G. 10 mg/kg 4 times a day for 7 days
Antibiotics ointment After the treatment: FIG. 35 is an affected part of the patient after the treatment. The lesion dried, desquamated and became flat 3 days later.

Figure 36:
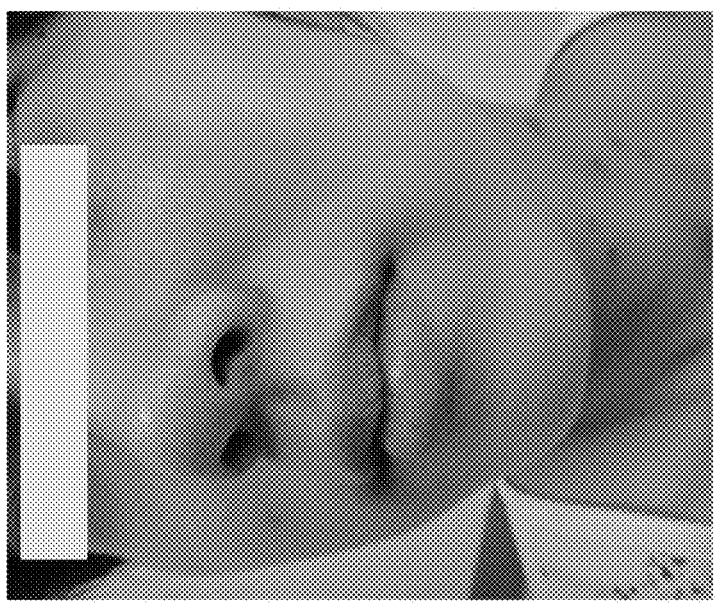
FIG. 36 is a picture showing $3^{rd}$ clinical case of impetigo 3 days after the treatment.

3$^{rd}$ Clinical Case of Impetigo 3 days after the treatment: FIG. 36 is after the treatment the vesicles found over her left neck 6 days ago collapsed. Some vesicles over her face appeared on the day she came to clinic despite of the treatment.

Figure 37B:
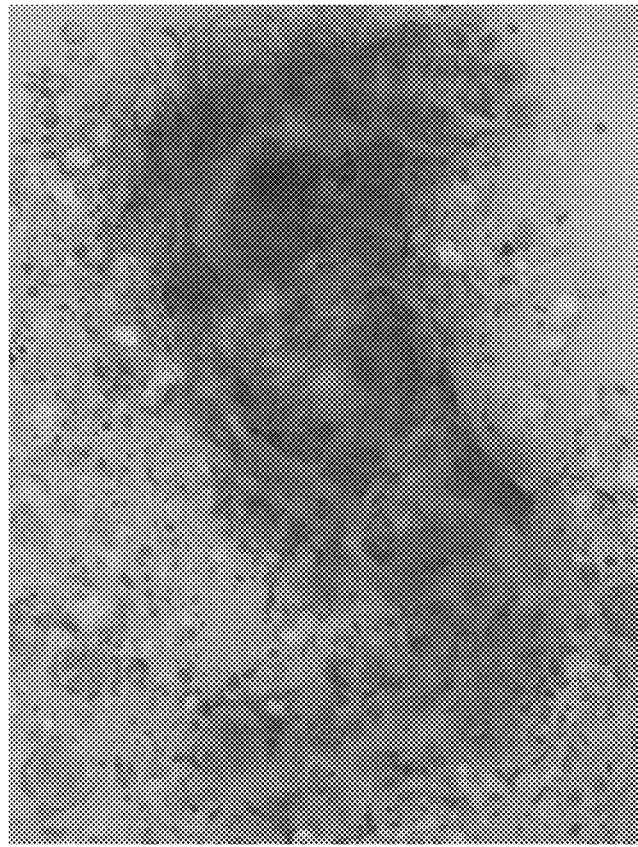
FIG. 37a-FIG. 37b are photomicrographs of cells of 3$^{rd}$ clinical case of impetigo.
Figure 37A:
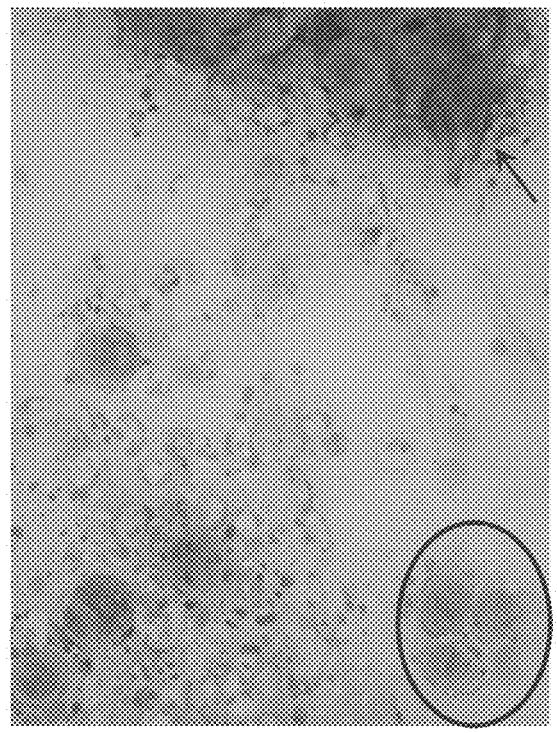

FIG. 37a is a first image of QTT sample: The QTT taken from a vesicle revealed BC with pleomorphic nuclei and high N/C ration gathering together to form a BC nest (circle). A degenerated nerve (arrow) was surrounded by ballooning Schwann cells.

FIG. 37b is a second image of QTT sample: The QTT taken from a vesicle revealed a lot of balloon cells and giant cell with severe nuclear pleomorphism.

Diagnosis: impetigo induced by HSV infection
Prescriptions:
Valacyclovir: 2 tablets daily for 7 days (1$^{st}$ visit)
Anti-allergic agent
Antibiotics 2 days due to cocci were also found on the QTT (2$^{nd}$ visit)

Figure 38:
FIG. 38 is a picture showing 3$^{rd}$ clinical case of impetigo after treatment.

After the treatment: FIG. 38 is an affected part of the patient after the treatment. Symptoms have significantly improved 7 days later.

4$^{th}$ Clinical Case of Impetigo

Figure 39:
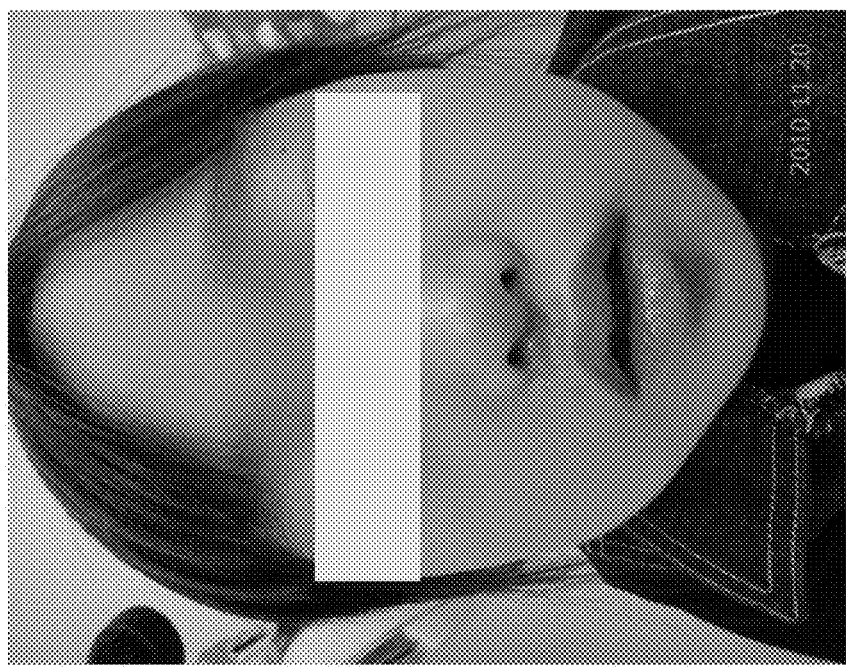
FIG. 39 is a picture showing 4$^{th}$ clinical case of impetigo before treatment.

Before the treatment: FIG. 39 is a patient presented with large yellowish red crusts with exudation on her right nostril, mandible and left eye for 1 week.

Figure 40A:
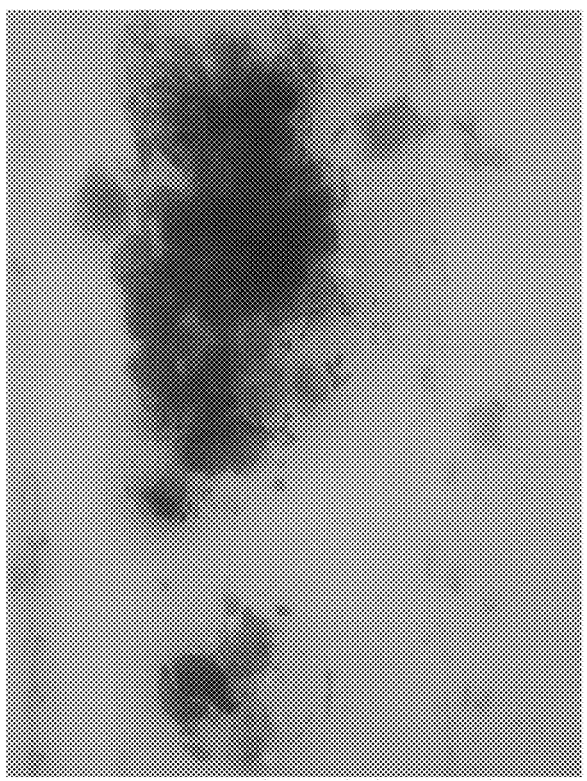
FIG. 40a-FIG. 40b are photomicrographs of cells of 4$^{th}$ clinical case of impetigo.

FIG. 40a is a first image of QTT sample: The QTT taken from a vesicle on her left eye revealed balloon degeneration of the Schwann cells of a DNF. The DNF extends to the epidermal sheet (ES).

Figure 40B:
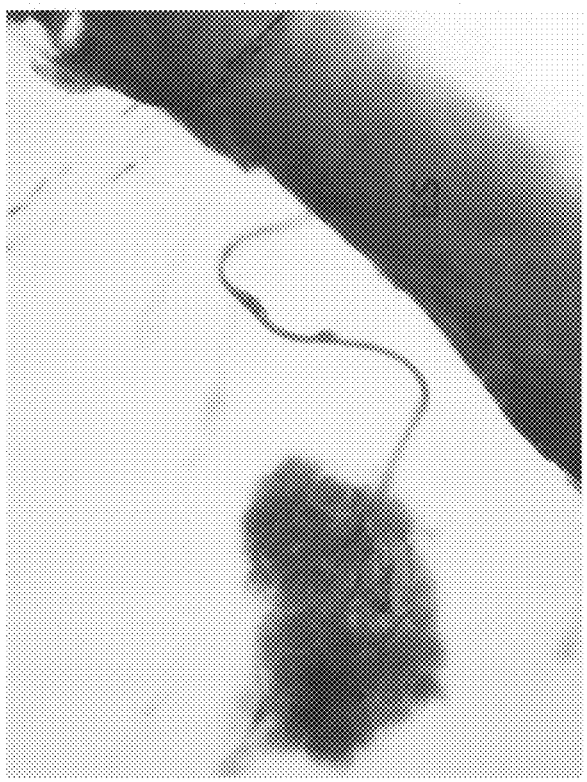

FIG. 40b is a second image of QTT sample: The QTT taken from a vesicle revealed many BCs and BCNs were observed in the dermis. The N/C ratio of the BC is very high.

Figure 41:
FIG. 41 is a picture showing 4$^{th}$ clinical case of impetigo after treatment.

Diagnosis: impetigo induced by HSV infection
Prescriptions:
acyclovir G. 10 mg/kg 4 times a day for 7 days
Oral antibiotics and anti-allergic agent for 5 days Antibiotics ointment After the treatment: FIG. 41 is an affected part of the patient after the treatment. There is nearly no skin lesion 4 days later. There is no recurrence till now (about one year).

5th Clinical Case of Impetigo

Figure 42:
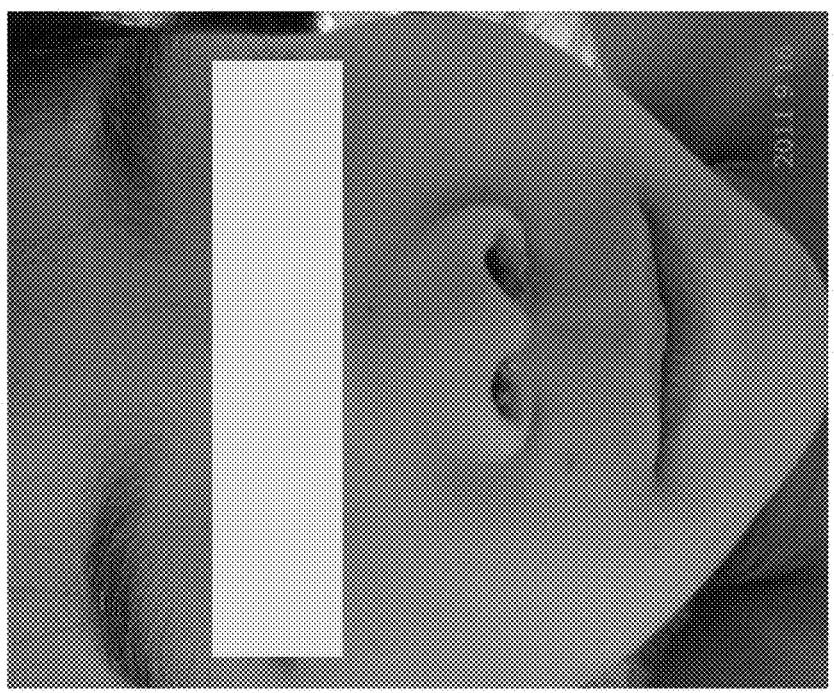
FIG. 42 is a picture showing 5$^{th}$ clinical case of impetigo before treatment.

Before the treatment: FIG. 42 is a patient presented with large yellowish red crusts in her nostrils and small ones over her face and complained of dry, scaly plaques over her trunk.

Figure 43:
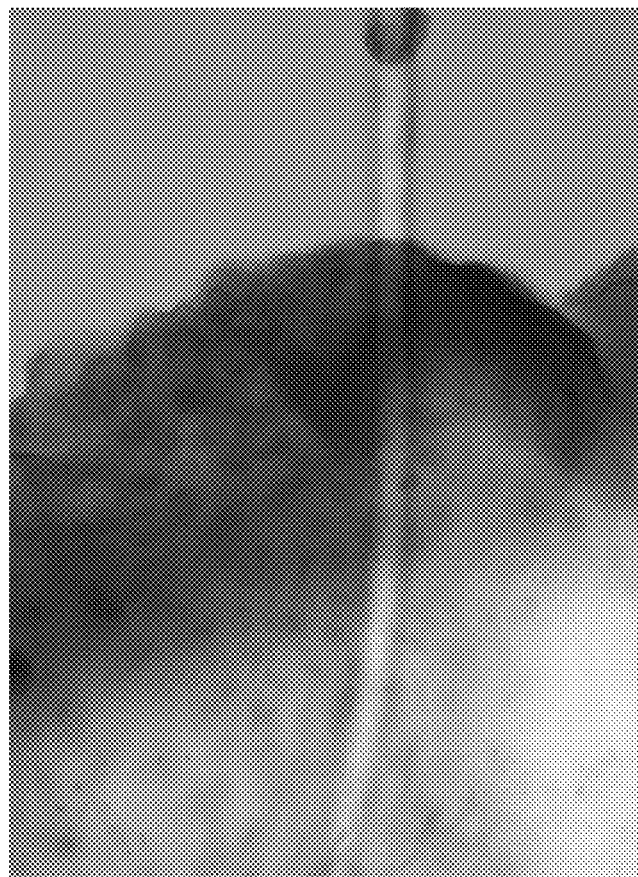
FIG. 43 is a photomicrograph of cells of 5$^{th}$ clinical case of impetigo.

FIG. 43 is an image of QTT sample: The QTT taken from a vesicopapule on her mandible revealed that the follicular epithelium in the dermis of a hair was completely destructed. Loss of polarity, highly irregular nuclear contours were observed in the spinous layer.

Diagnosis: impetigo induced by HSV infection and auto-sensitization dermatitis

Prescriptions:

Acyclovir G. 10 mg/kg 4 times a day for 7 days

Anti-allergic agents for 17 days

Gr. IV topical corticosteroids

Antibiotic ointment

Figure 44:
FIG. 44 is a picture showing 5$^{th}$ clinical case of impetigo after treatment.

After the treatment: FIG. 44 is an affected part of the patient after the treatment. There are some small erosions around her month and some vesiculopapules over the erythematosus eyelids 5 days later. There is no recurrence till now (about 14 months).

The mobility of impetigo in children is high. The most severe complication is glomerulonephritis. Fortunately, Streptococci induced impetigo is now commonly treated with antibiotics, the post-streptococcal glomerulonephritis is a rare complication (Post-streptococcal glomerulonephritis-PubMed Health, (2011)). On the other hand, 94% of chronic glomerulonephritis patients had a diagnostically significant level of IgG class anti-herpetic antibodies (Barinskii I F et al. "Herpesvirus infection in patients with chronic glomerulonephritis" Vopr Virusol 50 (1):35-37 (2005)) was reported. Among 75 patients studied, HSV type 1(34.4%), HSV type 2 (2.6%), cytomegalovirus (12%), mixed infections (46%). This result is consistent with this invention. The undiagnosed HSV (including other viruses)-induced impetigo may complicate by glomerulonephritis. In this invention, patients presented as impetigo diagnosed by the QTT responded well to the antiviral agent, thus the QTT may be a good screener to diagnose the HSV induced impetigo. Consequently, decrease the incidence of chronic glomerulonephritis.

1st Clinical Case of Pyoderma Gangrenosum

Figure 45:
FIG. 45 is a picture showing 1$^{st}$ clinical case of pyoderma gangrenosum before treatment.

Before the treatment: FIG. 45 is a patient presented with a large ulcer with yellowish exudation on the anterior aspect and a large crusted plaque on the posterior aspect of his lower leg. Besides, nearly half of the skin was reddish and edematous.

Figure 46:
FIG. 46 is a photomicrograph of cells of 1$^{st}$ clinical case of pyoderma gangrenosum.

FIG. 46 is an image of QTT sample: A degenerated nerve was surrounded by many pleomorphic BCs. Melanin pigments were also observed.

Laboratory data:

HSV IgG enzyme immunoassay titer (normal <2.0): >128

CMV IgG enzyme immunoassay titer (normal <2.0): 4.5

*Staph. Aureus* (MRSA): +

Diagnosis: pyoderma gangrenosum induced by HSV infection

Prescriptions:

Valacyclovir: 3 tablets daily for 10 days

Anti-allergic agent for 10 days

Antibiotics ointment

Gr. III topical corticosteroids (CS)

Figure 47:
FIG. 47 is a picture showing 1$^{st}$ clinical case of pyoderma gangrenosum after treatment.

After the treatment: FIG. 47 is an affected part of the patient after the treatment. 10 days later, although reddish-brown plaques were left, there were no more erosions and oozing.

2nd Clinical Case of Pyoderma Gangrenosum

Figure 48:
FIG. 48 is a picture showing 2$^{nd}$ clinical case of pyoderma gangrenosum before treatment.
Figure 48:
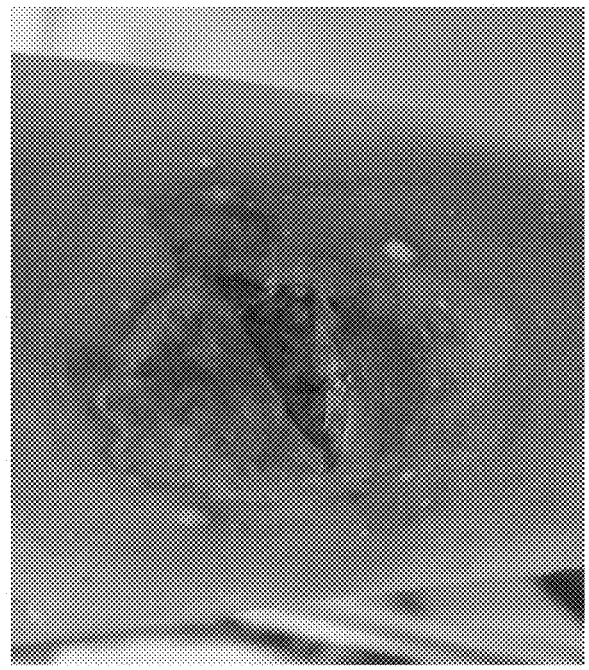

Before the treatment: FIG. 48 is a patient treated with systemic corticosteroids due to ulcerative colitis diagnosed 2 years ago. Several pustules appeared on her both legs 10 days ago. Some enlarged very fast and became nodules.

Figure 49:
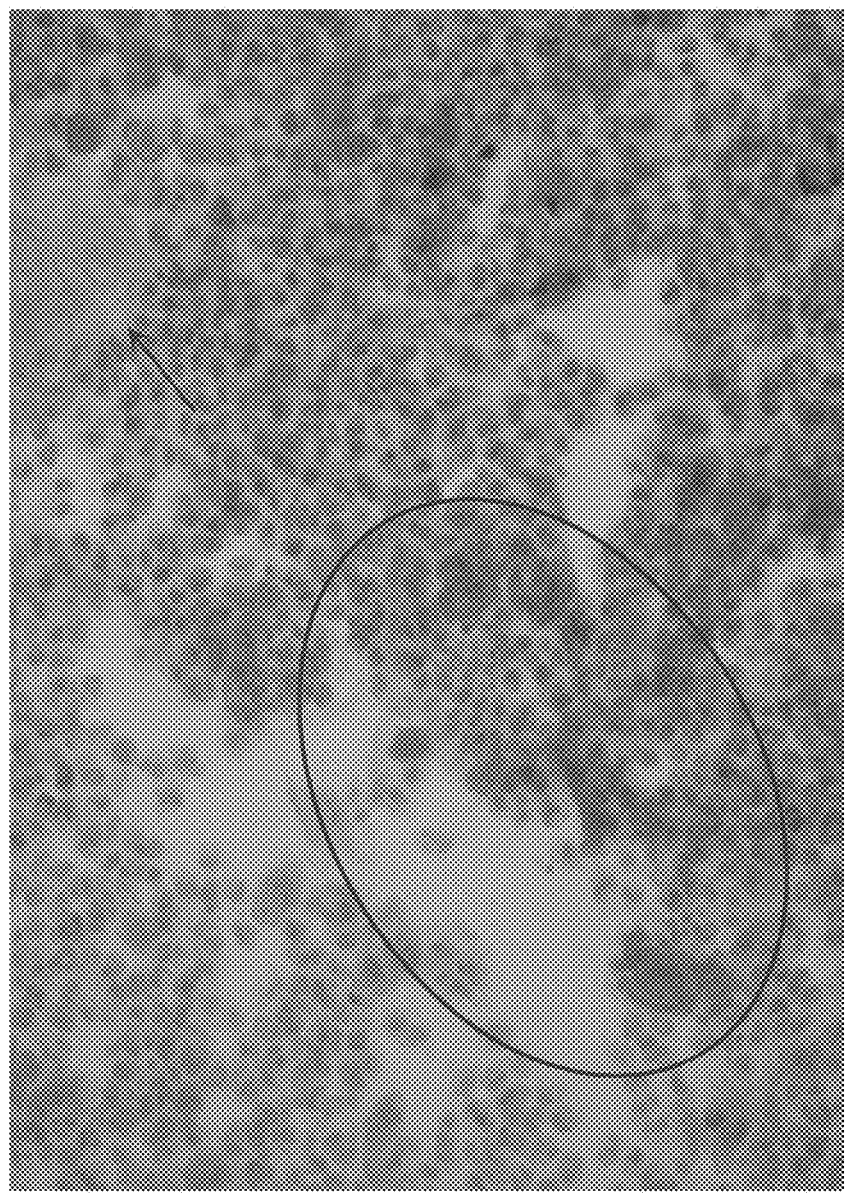
FIG. 49 is a photomicrograph of cells of 2$^{nd}$ clinical case of pyoderma gangrenosum.

FIG. 49 is an image of QTT sample: The QTT from a pustules revealed many BCs with eosinophilic inclusion body were seen among a dense inflammatory infiltration mainly by polymorphonuclear leukocytes. Degenerated nerves (arrow) were observed in the right upper corner. BCs with eosinophilic inclusion bodies in their nuclei (circle) were observed.

Diagnosis: pyoderma gangrenosum induced by HSV infection

Figure 50:
FIG. 50 is a picture showing 2$^{nd}$ clinical case of pyoderma gangrenosum after treatment.

Prescriptions:

1. oral prednisolone 40 mg for 11 days, then decreased to 35 mg, 30 mg, 30 mg, 25 every 7 days. The dose was further decreased and maintained dose was 15 mg.
2. Antibiotic ointment: gentamycin
3. Other treatment for ulcerative colitis is mesalazine After the treatment: FIG. 50 is an affected part of the patient after the treatment. Symptoms have significantly improved after the treatments. Some nodules healed and there were only some large erosions left 13 days later.

Viral infection has been implicated as precipitating factor of ulcerative colitis. However, only few papers succeeded in viral culture, the treatment are immunosuppressant agents to control the symptoms. It was reported that 0.6-5% of patients (Greenstein A J, "The extra-intestinal complications of Crohn's disease and ulcerative colitis", *Medicine* 55: 401-412 (1976)) suffering from ulcerative colitis complicated by pyoderma gangrenosum. Total proctocolectomy for extensive chronic ulcerative colitis was reported to bring about healing of associated pyoderma gangrenosum and without recurrence (Powell F C et al., *Arch Dermatol,* 120: 757-61, (1984)). This report confirmed that similar histopathological change may occur both in the gastrointestinal tract and skin. These 2 patients were diagnosed by the QTT as HSV infection. The first patient was treated by antiviral agent satisfactorily. It is worthwhile to apply The QTT to detect if there is a similar histopathological change in the gastrointestinal tract as found in the skin of the 2nd patient.

On the other hand, there are many reports concerning the adverse cutaneous reaction secondary to treatment with tumor necrosis factors-alpha inhibitors after 2000. Eczematide-like purpura (Wang L C et al., *J Am Acad Dermatol,* 49:157-8, 2003) leucocytoclastic vasculitis (Devos S A et al., *Dermatology,* 206: 388-90, 2003; Mcllwain L et al., *J Clin Gastroenterol,* 36: 411-13, 2003) and psoriasiform eruption (Verea M M et al., *Ann Phamacother,* 38:54-7, 2004) were reported after administration of the tumor necrosis factors-alpha inhibitors in patients suffering with Crohn's disease. These adverse reactions may occur with the same mechanism as in the patient 2nd clinical case of pyoderma gangrenosum with ulcerative colitis. It represents a systemic and peripheral spreading of the diseases. In other words, the adverse reaction actually provides a good chance for the QTT to detect their underlying etiology.

Pyoderma gangrenosum may complicate another important and mysterious disease: myelodysplasia. Nonmyelinating Schwann cells ensheathed autonomic nerves in mouse bone marrow was proved responsible for activation of the hematopoietic cells. Autonomic nerve denervation induced rapid loss of hematopoietic cells (Yamazaki S et al., *Cell*, 147:1146-58, 2011). In this invention, QTT detects the degenerated dermal nerve fibers surrounded by ballooning Schwann cells in various cutaneous diseases. Consistent with this latest reports, degenerated ballooning Schwann cells induce dysfunction of peripheral nerves thus bring vesicles, pustules, erosions and ulcers in skin; and bone marrow dysplasia (myelodysplasia) respectively. This can be applied to many other diseases associated with pyoderma gangrenosum. The frequent associations are rheumatoid arthritis (Stolman et al., *Arch Dermatol*, 111:1020-3 (1975)), Felty's syndrome (Kramer N et al., *J Rheumatol*, 17: 1079-82 (1990)), osteoarthritis (Lazarus G S et al., *Arch Dermatol*, 105:46-51 (1972)), acne conglobata (Powell F C et al., *Q J Med*, 55: 173-86 (1985)) and sacroileitis (Holt P J A et al., *Medicine* (Baltimore) 59: 114-33 (1980)). In this invention, QTT can thus be useful in elucidating weather these associated diseases are actually systemic infection of HSV.

$1^{st}$ Clinical Case of Chilblain

Figure 51:
FIG. 51 is a picture showing 1$^{st}$ clinical case of chilblain before treatment.

Before the treatment: FIG. 51 is a patient presented erythematosus swellings of her both ears for one week. There are erosions over her right earlobe.

Figure 52A:
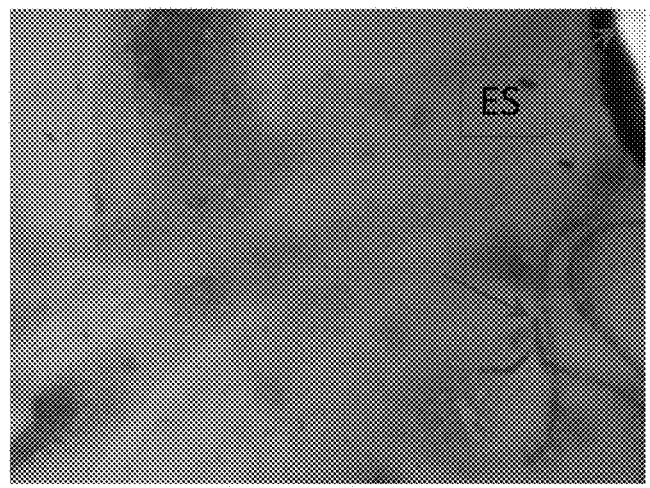
FIG. 52a-FIG. 52c are photomicrographs of cells of 1$^{st}$ clinical case of chilblain.

FIG. 52*a* is an image of QTT sample: There were several bands composed by inflammatory infiltration and degenerated tissues observed in the dermis. Several DNFs (arrow) extended from deep dermis to epidermal sheet (ES).

Figure 52B:

FIG. 52*b* is an image of QTT sample: A giant cell and some ballooning Schwann cells with pleomorphic nuclei were seen between 2 DNFs.

Figure 52C:
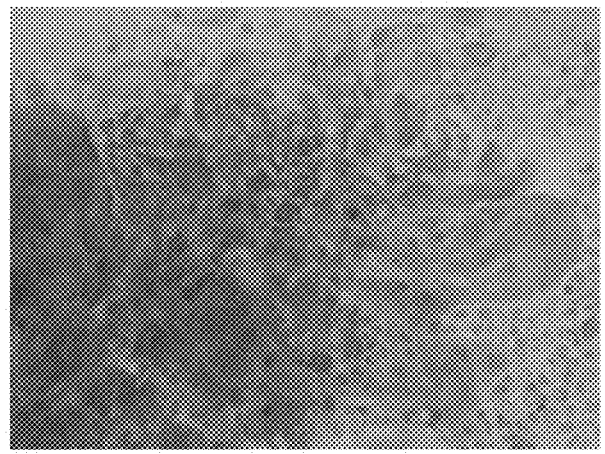

FIG. 52*c* is an image of QTT sample: Fine nerve fibers surrounded by ballooning Schwann cells were observed in deep dermis.

Figure 53:
FIG. 53 is a picture showing 1$^{st}$ clinical case of chilblain after treatment.

Laboratory data:
Non-specific immunoglobulin E (Ig E) titer (normal <170 IU/ml): 7.9 IU/ml
HSV IgG (normal <2.0): 39.3
CMV IgG (normal <2.0): 33.7
Prescriptions:
Acyclovir 200 mg: 3 tablets daily for 7 days
Diagnosis: chilblain induced by HSV infection After the treatment: FIG. 53 is an affected part of the patient after the treatment. The swelling and pain decreased a lot. The erosion improved 7 days later.

Figure 54:
FIG. 54 is a picture showing 2$^{nd}$ clinical case of chilblain 4 days after treatment.

$2^{nd}$ Clinical Case of Chilblain 4 days after $1^{st}$ prescriptions: FIG. 54 is a patient presented red swollen fingers with pain for one month. The lesions exacerbated gradually. The patient was treated yet without effect. This picture was taken 4 days after $1^{st}$ prescriptions under the diagnosis of HSV infection base on QTT and laboratory data.

Figure 55:
FIG. 55 is a picture showing 2$^{nd}$ clinical case of chilblain after 2$^{nd}$ prescriptions.

Laboratory data:
HSV IgG (normal <2.0): 33.8
Diagnosis: chilblain induced by HSV infection
Prescriptions of $1^{st}$ step:
Valacyclovir: 2 tablets daily for 4 days
Tocophenol nicotinate for 4 days
Anti-allergic agent for 4 days
Gr. III topical corticosteroids over the itchy lesions of the patient
Prescriptions of $2^{nd}$ step:
Valacyclovir: 1 tablets daily for 14 days
Anti-allergic agent for 14 days
ADO ointment: 2 time daily After the treatment of $2^{nd}$ prescriptions: FIG. 55 is an affected part of the patient after the treatment of $2^{nd}$ prescriptions. The red swollen fingers with pain were improved.

Figure 56:
FIG. 56 is a picture 2$^{nd}$ clinical case of chilblain after 3$^{rd}$ prescriptions.

Prescriptions of $3^{rd}$ step:
Valacyclovir: 1 tablets daily for 14 days
Anti-allergic agent for 14 days
ADO ointment: 2 time daily After the treatment of $3^{rd}$ prescriptions: FIG. 56 is an affected part of the patient after the treatment of $3^{rd}$ prescriptions. The red swollen fingers with pain were nearly cured.

Chilblain is localized inflammatory lesions that are caused by continued exposure to cold and dampness. Characteristic locations include the fingers, toes, heels, nose and ears. Nifedipine has been reported to be benefit (Down P M et al. "Nifedipine in the treatment of chilblains" *Br Med J*, 293: 923 (1986)), yet may induce headache and flushing. Cortisone ointment for itching and antibiotics for prevention of secondary infection are the most popular remedies. To the best of our knowledge, this invention includes the first description of the histopathological features of the HSV infection inducing DNF changes in chilblains by the QTT. Cold exposure induces replication of the latent HSV in DNFs and nerve free endings (NFEs). In addition, evokes a substance P mediated neurogenic inflammation presented as chilblain. The prompt response to the antiviral agents was consistent with the high titer of the HSV IgG which was 39.3. Another 8 patients cured by various amounts of antiviral agents are included in this invention. Besides 2 children not checked, the titer of the HS Ig G patients suffered from chilblains was 33.8 to over 128.

| Sex | Age | body parts | HSV IgG | Acyclovir 200 mg | Acyclovir 400 mg | Valacyclovir 500 mg |
|---|---|---|---|---|---|---|
| female | 82 | feet | 76.7 | 25T | 50T | |
| male | 74 | feet | 108 | 25T | | |
| male | 58 | feet | 107 | 25T | | 27T |
| female | 11 | hands | | 25T | | |
| female | 10 | feet | | 25T | | |
| female | 88 | feet | >128 | 50T | | |
| male | 77 | hands | 107 | 25T | | 17T |
| male | 68 | feet | >128 | 25T | 30T | |

Although chilblains is a self-limited disease, it is included in the diagnostic criteria of the systemic lupus erythematous (SLE). Viguier M. et al. investigated 33 patients affected with chilblain lesions for more than 1 month (Viguier M. et al., "Clinical and histopathologic features and immunologic variables in patients with severe chilblains. A study of the relationship to lupus erythematous" *Medicine* (Baltimore) 80 (3): 180-188 (2001)). 22 patients showed one or several abnormalities for the connective tissue diseases and 8 had a diagnosis of SLE. The hitopathologic studies included revealed only a deep perisudoral inflammatory infiltration. As there are many autonomic nerves around eccrine glands, the infiltration may represent the substance P mediated neurogenic inflammatory reaction toward HSV-infected cells.

Viral infection may cause death of the infected cells by direct effect. However, the HSV belonging to DNA viruses tend to integrating themselves in the cell nuclei where they produce latent infection (Young B et al., *Wheater's Basic Pathology*, 44 (2011)). Consequently, the genome of the host cell is recognized as foreign. This process may trigger the immune system to produce antibodies against the changed self to induce autoimmune hepatitis A (Vento S et al., *Autoimmunity Reviews*, 3:61-69 (2003)). In other words, auto antibodies detected in autoimmune diseases is the process in order to eradicate the viral-infected cells and not necessarily harmful. The inflammatory reaction in SLE may as in the chilblains aroused by the HSV infected Schwann cells in various organs and systems. Besides chilblain, glomerulonephritis, arthritis, anemia, cytopenia those among the diagnostic criteria of the SLE are included in this invention.

Although the clinical symptoms and sighs of the peripheral neuropathy are thoroughly described, a specific cause cannot be identified. The nerve damage provoked after viral and bacterial infection was referred to as an indirect autoimmune processes as in SLE. This may be due to the HSV-infected cells do not show up in traditional thin HE and other stains. Besides chilblain, these phenomena may occur in diabetes mellitus (DM), Guillain-Barre syndrome, multiple sclerosis and chronic inflammatory demyelinating polyneuropathy. QTT or a thick Giemsa cytologic observation may be a better tool than traditional ones.

Clinical Case of Diabetic Skin Complications

Figure 57:
FIG. 57 is a picture showing the clinical case of psoriasiform before treatment.

Before the treatment: FIG. 57 is a patient presented many scaly reddish papules of various sizes and some psoriasiform plaques appeared over lower legs for one month. The scaly reddish papules of various sizes and some psoriasiform plaques were not itchy.

Figure 58:
FIG. 58 is a picture showing the clinical case of psoriasiform after treatment.

Laboratory data:
Ig E (normal <170 IU/ml): 12.8 IU/ml
HSV IgG enzyme immunoassay titer (normal <2.0): >128
CMV IgG enzyme immunoassay titer (normal <2.0): 111
Diagnosis: psoriasiform plaques induced by HSV infection
Prescriptions:
Narrowband Ultraviolet light B (NBUVB)
Gr. I and III topical corticosteroids (CS)
Acyclovir (400 mg): 3 tablets daily for 10 days continued by 2 tablets daily for another 10 days After the treatment: FIG. 58 is an affected part of the patient after the treatment. Some lesions disappeared and the scaling of the psoriasiform plaques decreased a lot 7 days afterwards.

About 60% to 70% of people with DM have mild to severe form of nerve system damage. On the same time, skin problems are common. 22 patients were treated due to various kinds of diabetic skin complications. The titer of the HSV IgG or CMV IgG of the patients listed below was high, they all responded well after adding antiviral agents into traditional treatments of the skin diseases.

| Sex | Age | HSV IgG CMV IgG | IgE | skin manifestation |
|---|---|---|---|---|
| male | 73 | 48.8 | 26.4 | psoriasiform |
| male | 55 | | | pyoderma |
| male | 62 | 41.9 | 1,625 | burn ulcer |
| male | 68 | <2.0 9.9 | 318 | dermatitis, tinea ungium |
| male | 67 | 45.4 11.8 | 57.1 | urticaria |
| male | 77 | >128 | | tinea ungium |
| male | 76 | | | psoriasiform |
| male | 64 | <2.0 21.7 | | autosensitization dermatitis |
| male | 62 | <2.0 30.2 | 37.7 | nummular eczema verruca vulgaris |
| male | 77 | >128 | 6.2 | psoriasiform |
| male | 64 | 74.6 22.1 | 346 | autosensitization dermatitis |
| male | 56 | >128 | 163 | Kaposi's varicelliform eruption |
| male | 79 | 65 | 82.6 | nummular eczema |
| male | 47 | 37 | 183 | pemphigus foliaceous |
| female | 69 | 5.2 | 264 | acute urticaria |

-continued

| Sex | Age | HSV IgG CMV IgG | IgE | skin manifestation |
|---|---|---|---|---|
| female | 83 | 6.5 | 7.4 | Kaposi's varicelliform eruption |
| female | 70 | >128 | 14.5 | chronic urticaria |
| female | 74 | 69.4 | 15.8 | autosensitization dermatitis |
| female | 65 | >128 111 | 12.8 | psoriasiform |
| female | 78 | 104 | 61.6 | Kaposi's varicelliform eruption |
| female | 49 | 89.9 25.2 | 247 | chronic ulcer |
| female | 73 | 70 | 255 | acne-like |

In 1976 Brown et al. found that enhanced glycogenic effects of neurotension and substance P over glucagon may result from their inhibition of insulin release (Brown et al., *Endocrinology*, 98:819-22 (1976)). It is reasonable to speculate that if the autonomic nerve controlling insulin secretion is infected by the HSV just as shown in this invention in the cases of chilblain would result in substance P secretion and consequent inhibition of insulin release. DM complicated by polyneuropathy had marked reduction of Substance P and calcitonin-related peptide containing nerve fibers in the dermis (Lindberge M et al., *J of Neurological Science*, 93: 289-296 (1989)) may be the result of the destruction of the DNFs. In a review article, O'connor T M et al. provided evidences proving that many chronic inflammatory diseases such as asthma, sarcoidosis, chronic bronchitis, IBD and RA are due to elevated level of the Substance P (O'connor T M et al., *J cellular physiology*, 201 167-180 (2004)).

The nerve network of the skin contains somatic sensory and sympathetic autonomic fibers. They function at every point of the body. Sensory nerve of the skin have been found to synthesize and release calcitonin gene-related peptide, somatostatin, substance P, neurokinin A, vasoactive intestinal peptide and melanocyte stimulating hormones (Karanth S et al., *Am J Anat* 191: 379 (1991)). The most important neuropeptide is substance P that was reported to be released in joint activating rheumatoid synoviocytes (Martin et al., *Science*, 235: 893-895 (1987)). The somatic peripheral nervous systems is responsible as receptors of touch, pain, temperature, itch and mechanical stimuli, and the automatic peripheral nervous systems control and regulate the body internally. If some parts of the peripheral nervous system is infected and become latent by the HSV, acute and chronic inflammation may be induced as observed in skin.

$1^{st}$ Clinical Case of Alopecia

Figure 59:
FIG. 59 is a picture showing 1$^{st}$ clinical case of alopecia before treatment.
Figure 59:

Before the treatment: FIG. 59 is a patient presented with recurrent itchy red vesicopapules over his back for 5 years. The patient also noticed a hair loss plaque over the right side of his scalp one week ago.

Figure 60A:
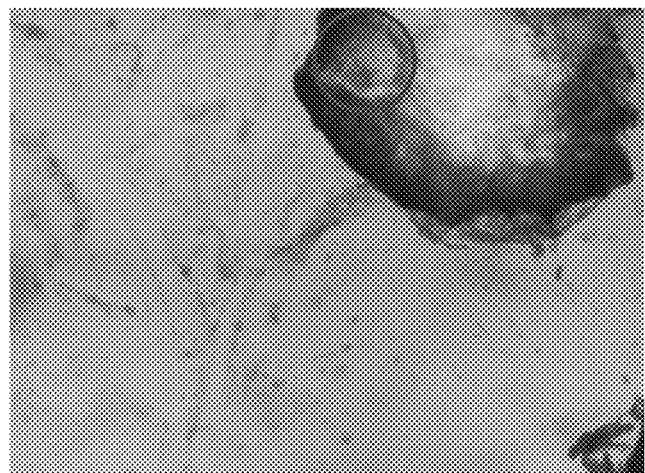
FIG. 60a-FIG. 60c are photomicrographs of cells of 1$^{st}$ clinical case of alopecia.

FIG. 60*a* is an image of QTT sample which from a red vesicopapule on the hair loss plaque revealed a large hair orifice (circle) filled by balloon cells.

Figure 60B:
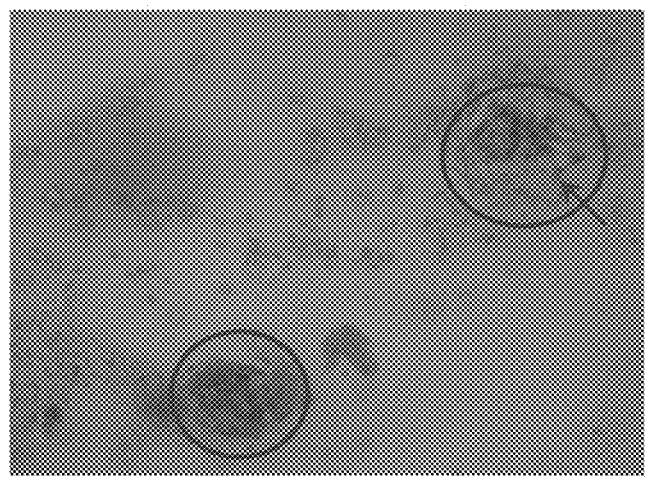

FIG. 60*b* is an image of QTT sample revealing a balloon degeneration of the Schwann cells of 2 dermal nerves (circles). The endoneurium (arrow) was partially preserved.

Figure 60C:
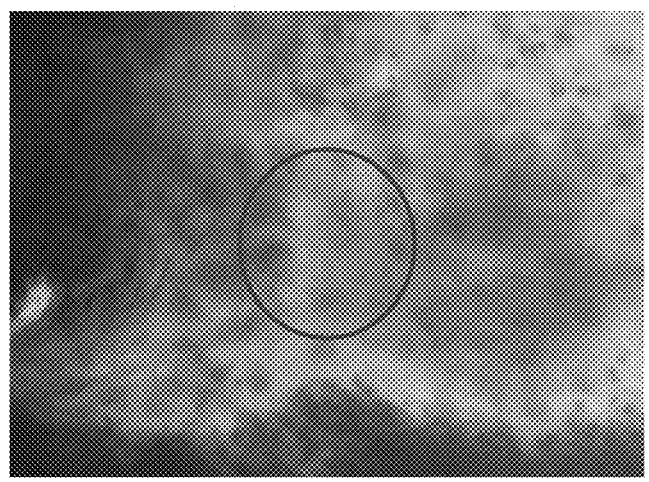

FIG. 60*c* is an image of QTT sample with high magnification revealed BCs and BCNs. BCs with EIBs (circle) were also found in the follicular orifice.

Diagnosis: alopecia and acne-like eruption due to HSV infection

Prescriptions:
Acyclovir (400 mg): 3 tablets daily for 10 days and 2 tablets daily for 14 days
Anti-allergic agent for 24 days
Gr. III topical CS.

Figure 61B:
FIG. 61a-FIG. 61d are pictures showing the 1$^{st}$ clinical case of alopecia after treatment.
Figure 61A:

After the treatment:

FIG. 61*a* is an affected part of the patient after the treatment. Small white hairs appeared especially over central portion 23 days later.

FIG. 61*b* was taken about 7 weeks after he finished Valacyclovir 2 tablets daily for 5 days. New hairs including black hairs increased a lot.

Figure 61C:
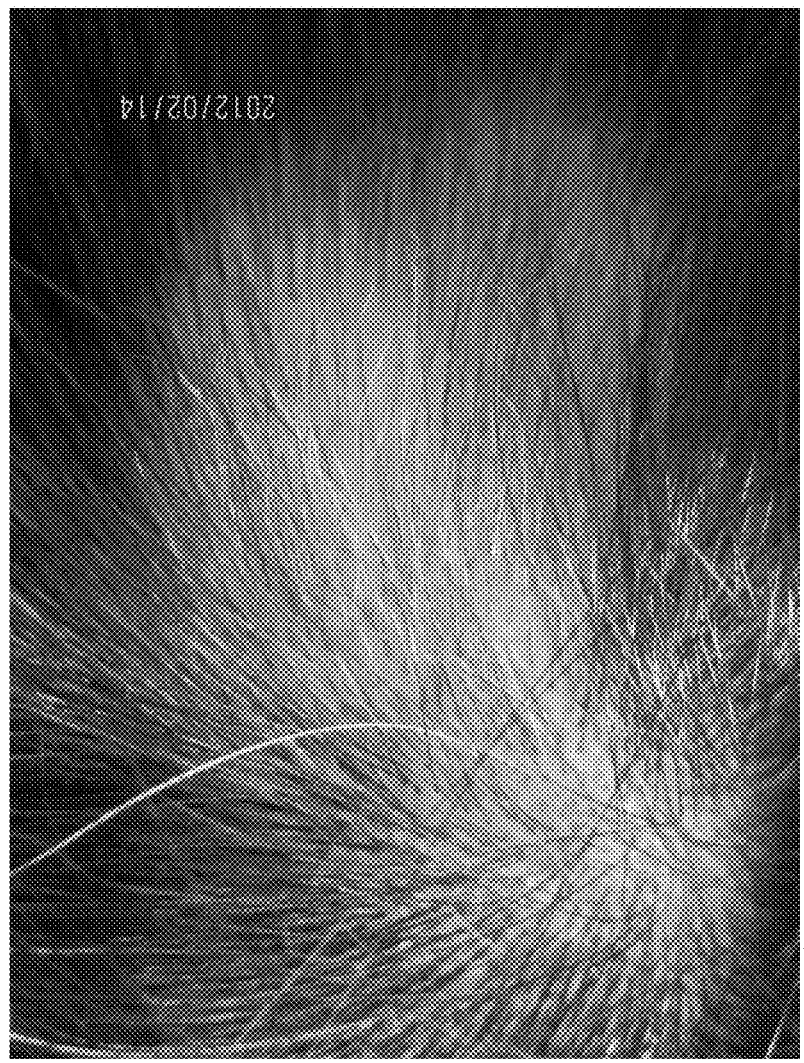

FIG. 61*c* was taken 21 weeks later. During these 3 weeks except Valacyclovir 2 tablets daily followed by 1 tablets daily for 5 days and a VD cream was prescribed twice a day, wherein the VD cream contain Diclofenac and Lidocaine.

Figure 61D:

FIG. 61*d* is an affected part of the patient after the treatment. There are only a few vesicopapules and pustules on his back.

$2^{nd}$ Clinical Case of Alopecia

Figure 62A:
FIG. 62a-FIG. 62c are pictures showing 2$^{nd}$ clinical case of alopecia before treatment.
Figure 62B:
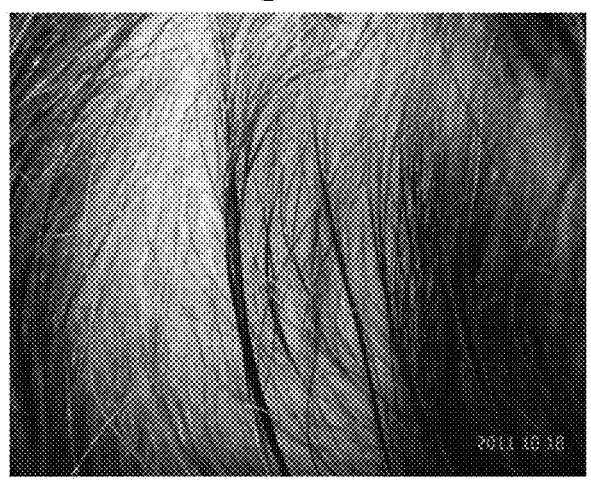
Figure 62C:

Before the treatment: FIG. 62*a* is a patient presented with a pustule appeared around a hair follicle over an atrophic whitish plague without hair appeared 4 years ago. Please refer FIG. 62*b*-62*c*, the patient also complained of hair loss especially over the posterior (FIG. 62*b*) and right(FIG. 62*c*) portions of her scalp.

Figure 63B:
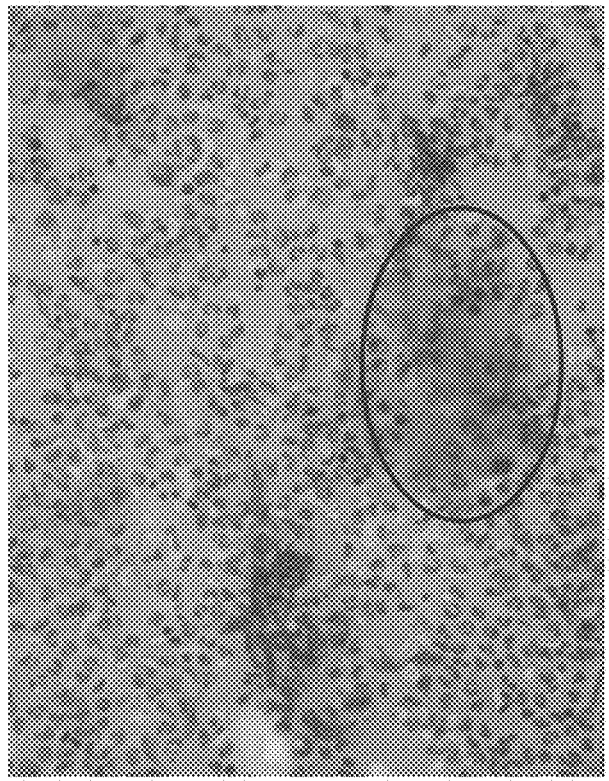
FIG. 63a-FIG. 63b are photomicrographs of cells of 2$^{nd}$ clinical case of alopecia.
Figure 63A:
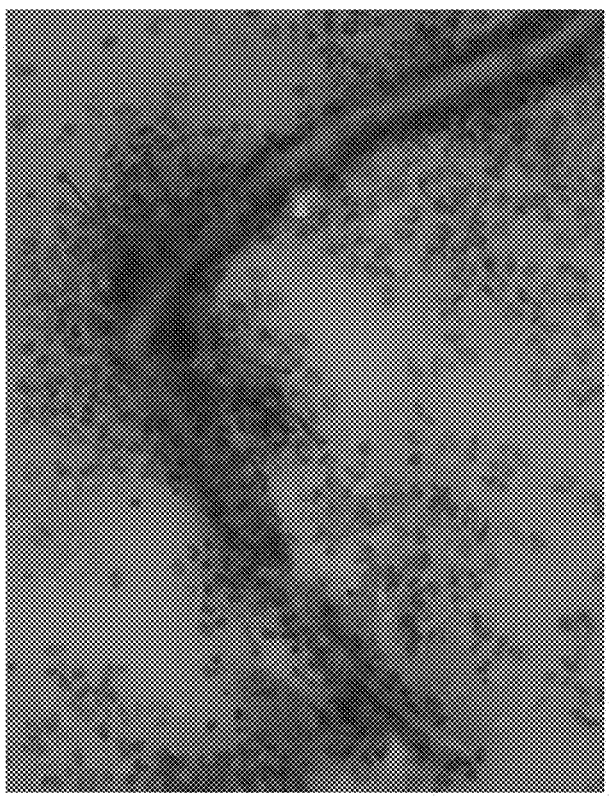

FIG. 63*a* is an image of QTT sample which from the pustule. A degenerated nerve was surrounded by BCs (arrows), mononuclear cells, and many PMNs.

FIG. 63*b* is an image of QTT sample revealing a balloon cell island (circle) composed by BCs with pleomorphic nuclei was surrounded by an inflammatory infiltration mainly by PMNs.

Laboratory data:

HSV IgG enzyme immunoassay titer (normal <2.0): 45.1

Diagnosis: alopecia due to HSV infection

Prescriptions:

Valacyclovir 1 tablets daily after dinner for 95 days.

Anti-allergic agent for 15 days

Acyclovir ointment for 6 weeks

Figure 64A:
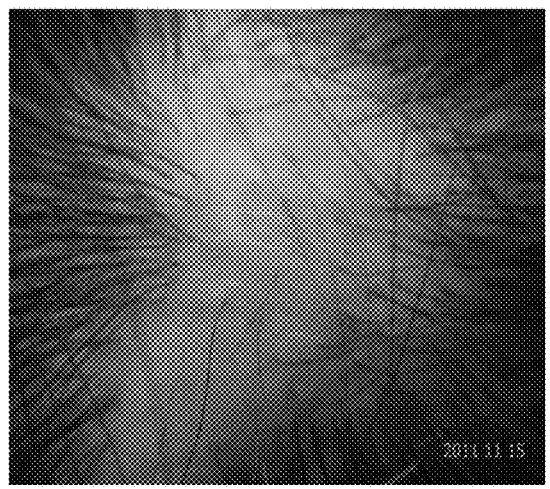
FIG. 64a-FIG. 64c are pictures showing the 2$^{nd}$ clinical case of alopecia after treatment.
Figure 64B:
Figure 64C:

After the treatment: FIG. 64*a* is an affected part of the patient after the treatment. The pustule disappeared a week later. There is nearly no change on the atrophic plague 2 weeks later. FIG. 64*b*, hair increased obviously on the right side and posterior aspect 4 weeks later. FIG. 64*c*, New black hairs (circle) were observed and no more alopecia on the right side 16 weeks later.

Alopecia (areata, universalis, cicatrica) is known as an autoimmune disease till now. Spontaneous recovery can be expected within a few months to a year in minor disease. Both of the patients suffered from alopecia have another disease acne-like eruption ($1^{st}$ case); vesicles around pelvic area ($2^{nd}$ case) caused by HSV.

Alopecia is usually presented as a hair loss area. The vesicopapule and pustule in the lesion provided a good chance for approaching the pathogenesis of alopecia. QTT from the vesicopapule and pustule confirmed that hair loss is due to the HSV infection of the Schwann cells in the DNFs. The degenerated nerve fibers were surrounded by the BCs and severe inflammatory infiltration. It is possible that the traditional histiopathologic study only revealed the severe inflammatory infiltration and failed in disclosing the HSV-infected cells.

The patient in $2^{nd}$ case had a fibrotic alopecic plague for 4 years. Pustules appeared after the antiviral therapy suggested that the HSV infected cells were deeper in the dermis than that in the 1st case. The pustule is the result of the reaction after antiviral therapy. It took 4 months, but two patients had satisfactory recovery.

Alopecia is also included in the diagnostic criteria of the SLE besides chilblain, glomerulonephritis, arthritis, anemia, cytopenia. It is also common in autoimmune diseases such as acquired thyroid disease, vitiligo, diabetes and collagen diseases. There is a great chance that the inflammatory reaction toward changed self in these diseases may as in the alopecia aroused by the HSV infected Schwann cells in various organs and systems.

Other diseases are related to latent infection of the HSV in Peripheral nerve fibers (PNFs), dermal nerve fibers (DNFs) and free nerve endings (FNEs) besides above diseases. QTT enables cytology observation of the pathologic changes for the following diseases occurring in DNFs and FNEs of the epidermis and dermal nerve networks. The above mentioned anti-HSV agent or the combination thereof can be used for the treatment of the following other diseases, which are named as below:

1. Asteatotic dermatitis
2. Ichthyosis
3. Lichen simplex chronicus (Neurodermatitis, Prurigo)
4. Seborrhoeic dermatitis
5. Rosacea
6. Perioral dermatitis
7. Epidermal cyst
8. Ulcerative colitis
9. Crohn's disease
10. Myelodysplasia, multiple myeloma
11. Wound, ulcer
12. Discoid lupus erythematosus
13. Vitiligo
14. Chilbrain
15. Demyelinating disease
16. Parkinson's disease This invention discloses these QTT-positive patients show remarkable response to antiviral agent. They could and should be treated promptly in order to prevent the latent state and being an infectious source.

Those described above are the embodiments to exemplify the present disclosure to enable the person skilled in the art to understand, make and use embodiments of the present disclosure. This description, however, is not intended to limit the scope of the present disclosure. Any equivalent modification and variation according to the spirit of the present disclosure is to be also included within the scope of the claims stated below.

The components, steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, benefits and advantages. These also include embodiments in which the components and/or steps are arranged and/or ordered differently.

In reading the present disclosure, one skilled in the art will appreciate that embodiments of the present disclosure can be implemented in hardware, software, firmware, or any combinations of such, and over one or more networks. Suitable software can include computer-readable or machine-readable instructions for performing methods and techniques (and portions thereof) of designing and/or controlling the fabrication and design of integrated circuit chips according to the present disclosure. Any suitable software language (machine-dependent or machine-independent) may be utilized.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. The scope of protection is limited solely by the claims. That scope is intended and should be interpreted to be as broad as is consistent with the ordinary meaning of the language that is used in the claims when interpreted in light of this specification and the prosecution history that follows and to encompass all structural and functional equivalents.

Those skilled in the art will readily observe that numerous modifications and alterations of the device and method may be made while retaining the teachings of the invention. Accordingly, the above disclosure should be construed as limited only by the metes and bounds of the appended claims.

REFERENCES

1. Lily H. Herpes simplex virus-associated dermatitis with either high or normal IgE responded well to antiviral therapy: A study of 787 quick Tzanck test positive Patients.
2. Hsiao L, Gieh S H. The 2-minute quick Tzanck test to diagnose herpes simplex viral infection: cytologic and clinical atlas of skin diseases including atopic dermatitis. HO-CHI publication. 2011; August
3. Hsiao L. Considerable Remission after Continuous Oral Antiviral Therapy in Darier's Disease: Two Sisters. WebmedCentral VIROLOGY 2012; 3(12): WMC003883
4. Tzanck A. Le Cyto-diagnostic immediate en dermatologie. Ann Dermatol Venereol. 1947; 7: 68-70
5. Ozcan A, Senol M, Saglam H, et al. Comparison of the Tzanck test and polymerase chain reaction in the diagnosis of cutaneous herpes simplex and varicella zoster virus infection. Int J Dermatol 2007; 46: 1177-1179
6. Ruocco E, Brunetti G, Vecchio M D, and Ruocco V. The practical use of cytology for diagnosis in dermatology. J Eur Acad Dermatol Venereol. 2011 February; 25(2):125-9.
7. Durdu M, Seçkin D, Baba M. The Tzanck smear test: rediscovery of a practical diagnostic tool. SKINmed 2011; 9: 23-32.
8. Whitley R J, Nahmias A J, Visintine A M, et al. The natural history of herpes simplex virus infection of mother and newborn. Pediatrics. 1980: 66: 489-494.
9. Serdar H U, Thomas C C P. Genital herpes in pregnancy. Med Scape Reference. Jan. 23, 2013
10. Cesario T C, Poland J D, Wulff H. et al. Six years experience with herpes simplex virus in a children's home. American J Epidermol. 1969; 90: 416
11. Anderson S G, and Hamilton J. The epidemiology of primary herpes simplex infection. Med. J Australia. 1949; 1:308-311.
12. Hale B D, Rendtorff R C, Walker L C and Robert A N. Epidemic herpetic stomatitis in an orphanage nursery. JAMA. 1963; 183: 1068-1072.
13. Birek C and Ficarra G. The diagnosis and management of oral herpes simplex infection. Current infectious disease reports 2006; 8: 181-188.
14. Harel L, Smetane Z, Prais D, et al Presence of viremia in patients with primary herpetic gingivostomatitis. Clin Infect Dis 2004, 39: 636-640.
15. Brice S L, Stockert S S, Jester J D, et al. Detection of herpes simplex virus DNA in the peripheral blood during acute recurrent herpes labialis. J Am Acad Dermatol. 1992; 26:594-598
16. Youssef R, Shaker O, Sobeih S, et al. Detection of herpes simplex virus DNA in Serum and Oral secretions during acute recurrent herpes labialis. J of Dermatol. 2002; 29:404-410.
17. Amatsu A, Yoshida M. Detection of herpes simplex virus in non-herpetic areas of patients with eczema herpeticum. Dermatology 2000; 200: 104-7.
18. Miura S, Smith C C, Burnett J W, Aurelian L. Detection of viral DNA with in skin of healed recurrent herpes simplex infection and erythema multiforme lesions. J Invest Dermatol. 1992; 98: 68-72.
19. Syrjanene S, Mikola H, Nykanen M, Hukkanen V. In vitro establishment of lytic and nonproductive infection by herpes simplex virus type 1 in three-dimensional keratinocytes culture. J virol. 1996; 70: 6524-8.
20. Burkhart C N, Burkhart C G. The bimodal temporal distribution of herpetic reactivation. Mayo Clinic Proceed. 2005; 80: 287-8.
21. Rothe M J, Grant-Kels J M. Diagnostic criteria for atopic dermatitis. Lancet. 1996; 348: 769-770.
22. Wollenberg A, Zoch C, Wetzel S, Plewig G, Przybilla B. Predisposing factors and clinical feature of eczema herpeticum: a retrospective analysis of 100 cases. J Am Acad Dermatol. 2003; 49(2): 198-205.
23. Kotani H, Masuda K, Tamagawa-Mineoka R, et al. Increased plasma LIGHT levels in patients with atopic dermatitis. Clin Exp Immunol. 2012; 168(3):318-24.
24. Samoylikov P, Gervazieva V, Kozhevnikov S. Association between autoimmune reactions and severity of atopic dermatitis in children with herpes virus infection. World Allergy Organ J. 2013; 6(1):8. doi: 10.1186/1939-4551
25. Hinz T, Zaccaro D, Byron M, Brendes K, et al. Atopic derma-respiratory syndrome in a correlate of eczema herpetium. Allergy. 2011; 66(7):925-33.
26. Kimura H, Futamura M, Kito H, et al. Detection of viral DNA in neonatal herpes simplex infections: frequent and prolonged presence in serum and cerebrospinal fluid. J infectious dis. 1991; 164: 289-293.
27. Corey L, Wald A. Maternal and neonatal HSV infections. N Engl Med. 2009; 361 (14):1376-1385.
28. Robinson J L, Vaudry W L, Forgie S E, Lee B E. Prevention, recognition and management of neonatal HSV infections. Expert Rev Anti Infec Ther. 2012; 10 (6): 675-685
29. Hsiao L Takeya M, Arao T, and Takahashi K. An immunohistochemical and immunoelectron microscopic study of the ontogeny of rat Langerhans cell lineage with anti-microphage and anti-Ia monoclonal antibodies. J Invest Dermatol. 1989; 93: 780-786.
30. Kohl S. A hypothesisi on the pathophysiology of neonatal herpes simplex virus encephalitis: clinical recurrence after asyptomatic primary infection. Pediatric Infect Dis. 1990; 9: 307-308.
31. Stanberry L R, Folyd-reising S A, Connerally B L. Herpes simplex viremia: reports of eight pediatric cases and review of literature. Clin Infect Dis 1994; 28: 401-7.
32. Grose C. Acute retinal necrosis caused by herpes simplex virus type 2 in children: reactivation of an undiagnosed latent neonatal herpes infection. Semin Pediatr Neurol. 2012; 19: 115-118.
33. Mori I, Nishiyama Y, Yokoji T and Kimura Y. Olfactory transmission of neurotropic viruses. J of NeuroVirology. 2005; 11:129-137.
34. Becker Y. HSV-1 Brain infection by the olfactory nerve route and virus latency and reactivation may cause learning and behavioral deficiencies and violence in children and adults: a point of view. Virus genes. 1995; 10: 217-226.
35. Hussain I, Smith J. Evidence for the transmissibility of atopy: hypothesis. Chest. 2003; 124(5): 1968-74.
36. Lagacé-Simard J, Portnoy J D, Wainberg M A. *High levels of IgE in patients suffering from frequent recurrent herpes simplex lesions*. J Allergy Clin Immunol. 1986 April; 77(4):582-5.
37. Ida S, Siraganian R P, Notkins A L. Cell-bound and circulating IgE antibody to herpes simplex virus. J Gen Virol. 1983; 64: 533-537.

What is claimed is:

1. A method for treating a symptom of redness, red swollen, itching, blisters, and inflammation on a skin of a human, caused by continued exposure to cold and dampness, comprising:
   testing whether said human is infected with Herpes simplex virus (HSV); and
   after said testing whether said human is infected with Herpes simplex virus (HSV), orally administering to said human an agent comprising
   2-[(2-amino-6-oxo-6,9-dihydro-3H-purin-9-yl)methoxy]ethyl-2-amino-3-methylbutanoate or a pharmaceutically acceptable salt thereof for treating said symptom.

2. The method of claim 1, wherein said salt comprises an acid addition salt.

3. The method of claim 1, wherein said testing whether said human is infected with HSV comprises performing a Quick Tzanck Test (QTT) on a sample taken from said skin of said human.

4. The method of claim 1 further comprising administering topical corticosteroids ointment or cream over said skin of said human.

5. The method of claim 1, wherein said testing whether said human is infected with HSV comprises detecting a Herpes simplex virus (HSV) immunoglobulin G titer of said human.

6. A method for treating a symptom of redness, red swollen, itching, blisters, and inflammation on a skin of a human, caused by continued exposure to cold and dampness, comprising:
   testing whether said human is infected with Herpes simplex virus (HSV); and
   after said testing whether said human is infected with Herpes simplex virus (HSV), orally administering to said human an agent comprising
   2-Amino-1,9-dihydro-9-((2-hydroxyethoxy)methyl)-6H-purin-6-one or a pharmaceutically acceptable salt thereof for treating said symptom.

7. The method of claim 6, wherein said salt comprises an acid addition salt.

8. The method of claim 6, wherein said testing whether said human is infected with HSV comprises performing a Quick Tzanck Test (QTT) on a sample taken from said skin of said human.

9. The method of claim 6, further comprising administering topical corticosteroids ointment or cream over said skin of said human.

10. The method of claim 6, wherein said testing whether said human is infected with HSV comprises detecting a Herpes simplex virus (HSV) immunoglobulin G titer of said human.

* * * * *